US008697848B2

(12) United States Patent
Seefeldt et al.

(10) Patent No.: US 8,697,848 B2
(45) Date of Patent: Apr. 15, 2014

(54) METHOD FOR REDUCING IMMUNOGENICITY OF THERAPEUTIC PROTEIN COMPOSITIONS

(75) Inventors: Matthew Seefeldt, Denver, CO (US); Theodore W. Randolph, Niwot, CO (US); Amber Haynes Fradkin, Golden, CO (US); John Carpenter, Denver, CO (US)

(73) Assignees: The Regents of the University of Colorado, Denver, CO (US); Barofold, Inc., Aurora, CO (US)

( * ) Notice: Subject to any disclaimer, the term of this patent is extended or adjusted under 35 U.S.C. 154(b) by 2 days.

(21) Appl. No.: 13/186,169

(22) Filed: Jul. 19, 2011

(65) Prior Publication Data

US 2012/0070406 A1    Mar. 22, 2012

Related U.S. Application Data

(60) Provisional application No. 61/365,728, filed on Jul. 19, 2010.

(51) Int. Cl.
*C07K 14/00* (2006.01)
*C07K 1/00* (2006.01)
*C07K 16/00* (2006.01)
*A61K 38/00* (2006.01)
*A61K 39/00* (2006.01)

(52) U.S. Cl.
USPC ......... 530/427; 530/350; 514/1.1; 424/130.1; 424/184.1; 424/192.1

(58) Field of Classification Search
None
See application file for complete search history.

(56) References Cited

U.S. PATENT DOCUMENTS

| 6,489,450 B2 | 12/2002 | Randolph et al. |
| 7,064,192 B2 | 6/2006 | Randolph et al. |
| 7,538,198 B2 | 5/2009 | Randolph et al. |
| 7,767,795 B2 | 8/2010 | Randolph et al. |
| 7,829,681 B2 | 11/2010 | Seefeldt et al. |
| 2007/0099926 A1 | 5/2007 | Rodger et al. |
| 2008/0161242 A1 | 7/2008 | Randolph et al. |
| 2008/0249286 A1 | 10/2008 | Seefeldt et al. |
| 2009/0076247 A1 | 3/2009 | Seefeldt et al. |
| 2009/0215998 A1 | 8/2009 | Antman et al. |
| 2010/0075399 A1 | 3/2010 | Randolph et al. |
| 2010/0255536 A1 | 10/2010 | Randolph et al. |
| 2011/0046357 A1 | 2/2011 | Randolph et al. |
| 2011/0070219 A1 | 3/2011 | Seefeldt et al. |

FOREIGN PATENT DOCUMENTS

| WO | WO 00/02901 | 1/2000 |
| WO | WO 02/062827 | 8/2002 |
| WO | WO 2007/062174 | 5/2007 |
| WO | WO 2008/033555 | 3/2008 |
| WO | WO 2008/033556 | 3/2008 |
| WO | WO 2008/124134 | 10/2008 |
| WO | WO 2008/124139 | 10/2008 |
| WO | WO 2009/035617 | 3/2009 |
| WO | WO 2009/045553 | 4/2009 |

OTHER PUBLICATIONS

Carpenter, et al. "Overlooking Subvisible Particles in Therapeutic Protein Products: Gaps That May Compromise Product Quality," Journal of Pharmaceutical Sciences, Aug. 14, 2008, vol. 98(4), pp. 1201-1205.
Narhi, et al., "Critical Review of Analytical Methods for Subvisible and Visible Particles," Current Pharmaceutical Biotechnology, 2009, vol. 10(4), pp. 373-381.
International Search Report and Written Opinion mailed Jan. 12, 2012 in related International application No. PCT/US11/44485, 13 pages.
Fradkin, Amber Haynes, et al , "Immunogenicity of aggregates of recombinant human growth hormone in mouse models," Journal of Pharmaceutical Sciences, 96(9): 3247-3264, Sep. 1, 2009.
Braun A, et al., "Protein aggregates seem to play a key role among the parameters influencing the antigenicity of interferon alpha (IFN-alpha) in normal and transgenic mice," Pharmaceutical Research, 14(10):1472-1478, Oct. 1, 1997.
Gorovits & M Horowitz BM, "High hydrostatic pressure can reverse aggregation of protein folding intermediates and facilitate acquisition of natice structure," Journal of Biological Chemistry, 270(5):2061-2066, Feb. 3, 1995.
Phelps, David J., et al., "Protein disaggregation and refolding using high hydrostatic pressure," Journal of Chemical Technology and Biotechnology, 82(7):610-613, Jul. 1, 2007.
Seefeldt, Matthew B., et al., "High-pressure refolding of bikunin: Efficacy and thermodynamics," Protein Science, 13(10):2639-2650, Oct. 1, 2004.
St. John, R.J., et al., "High pressure fosters protein refolding from aggregates at high concentrations," Proceedings of the National Academy of Sciences, 96(23):13029-13033, Jan. 9, 1999.
Babiuk, Shawn, et al., "Aggregate content influences the Th1/Th2 immune response to influenza vaccine: Evidence from a mouse model," Journal of Medical Virology, 72(1):138-142, Jan. 1, 2004.

*Primary Examiner* — Robert Landsman
*Assistant Examiner* — Bruce D Hissong
(74) *Attorney, Agent, or Firm* — Cooley LLP

(57) ABSTRACT

The present invention provides methods for reducing and/or evaluating the immunogenic potential of a therapeutic protein preparation. The present invention further provides pharmaceutical compositions of therapeutic proteins and methods of treatment with the same, the compositions having low immunogenic potential and/or improved efficacy. The invention achieves these goals by evaluating therapeutic protein preparations for subvisible protein particulates, which can contribute significantly to the overall immunogenic potential of the protein preparation. Further, by maintaining the content of such subvisible protein particulates to below an immunogenic threshold level, the resulting pharmaceutical composition is less likely to result in a loss of tolerance (e.g., upon repeated administration), thereby improving both the safety and efficacy profile of the therapeutic.

17 Claims, 23 Drawing Sheets

FIG.2
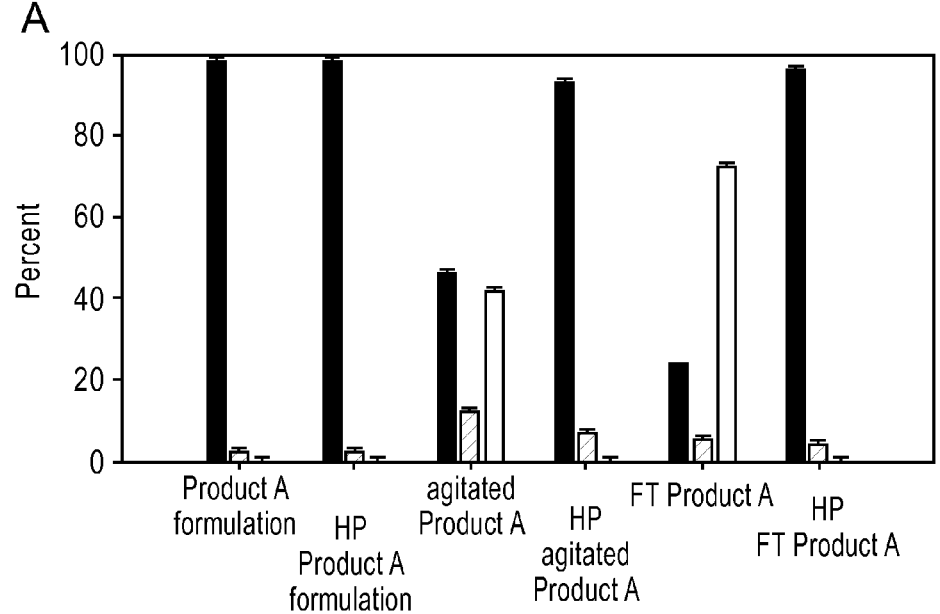
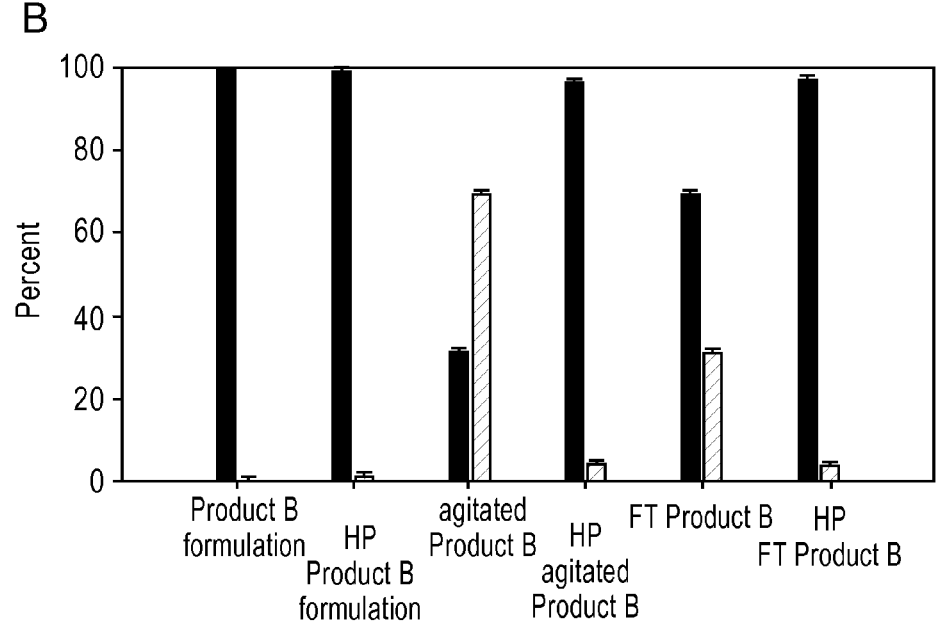

| Total Particle Counts | |
|---|---|
| Condition | #/ml |
| Atm 1 | 92700 |
| Atm 2 | 83225 |
| 1000 bar | 67225 |
| 1500 bar | 74025 |
| 2000 bar | 61975 |
| 2500 bar | 70200 |
| 3250 bar | 290800 |
| Formulation Buffer | 266 |

ND FOR REDUCING
METHOD FOR REDUCING IMMUNOGENICITY OF THERAPEUTIC PROTEIN COMPOSITIONS

PRIORITY

This application claims the benefit of U.S. Provisional Application No. 61/365,728, filed Jul. 19, 2010, which is hereby incorporated by reference in its entirety.

STATEMENT OF GOVERNMENT SUPPORT

This invention was made with government support under grant number R01-EB006006 awarded by the National Institutes of Health. The government has certain rights in the invention.

BACKGROUND

Recombinant therapeutic proteins have had a significant impact on the clinical treatment of diseases, including cancer, over the past few decades. There are over 630 recombinant proteins and peptides in commercial development, and protein-derived therapeutics continue to grow rapidly relative to small molecule therapeutics. As more recombinant proteins enter the pharmaceutical market, the potential risks associated with these products are becoming more of a concern. In particular, therapeutic proteins, unlike small molecules, may be unstable and prone to aggregation (Chi et al., *Physical stability of proteins in aqueous solution: Mechanism and driving forces in nonnative protein aggregation, Pharmaceutical Research* 20(9):1325-1336 (2003). Protein aggregation can compromise the safety and effectiveness of the product.

Even though industry and regulatory agencies are aware of aggregation and have policies and guidelines for their detection in therapeutic protein compositions, some aggregates still go undetected, in-part due to limitations of the conventionally accepted analytical techniques. For instance, the USP currently has no guidelines for detection of particles 0.1 to 10 microns in size. Protein aggregates less than 0.1 micron are detected by analytical methods such as size exclusion chromatography, and particles greater than 10 microns are detected by the USP light obscuration <788> technique. There are no clear recommendations for detection of particles greater than about 0.1 micron but less than about 10 microns, and the significance of these particles to the immunogenic potential of the product has not been demonstrated. This gap in subvisible particle detection leaves an opportunity for protein aggregates to exist in approved commercial products and current biologics undergoing development.

Protein aggregation occurs due to colloidal or conformation instability allowing proteins to assemble with concomitant loss of native structure and activity. Stresses such as freeze-thawing, agitation (e.g. air-water interface), and UV light exposure, are commonly encountered during processing, shipping, and storage of a therapeutic product and are known to aggregate proteins (Chi et al. 2003). Aggregates may also be generated during protein purification as the protein moves through a variety of solution exchanges at high protein concentrations on column surfaces. Protein aggregation may proceed through specific pathways that are initiated by instability of the native protein conformation or colloid instability associated with protein-protein interactions. Conditions such as temperature, solution pH, ligands and cosolutes, salt type and concentration, preservatives, and surfactants all modulate protein structure and protein-protein interactions, and thus aggregation propensity.

Aggregates produced as a result of different stresses may exhibit different size distributions and their component proteins may contain different secondary and tertiary structures, which presumably expose different epitopes, potentially provoking immune responses (Seefeldt et al., *High-pressure studies of aggregation of recombinant human interleukin*-1 *receptor antagonist: thermodynamics, kinetics, and application to accelerated formulation studies, Protein Sci.* 14(9): 2258-66 (2005)).

Protein aggregates present in therapeutic protein compositions may not be recognized as "natural" by the immune system. This might be due to exposure of a new epitope in the aggregated protein that is not exposed in the non-aggregated protein, or by formation in the aggregate of a new epitope, with the result that the immune system is sensitized to the administered recombinant protein aggregate. While in some instances the immune system produces antibodies to the aggregates that do not neutralize the therapeutic effect of the protein, in other cases, antibodies are produced that bind to the recombinant protein and interfere with the therapeutic activity, thereby resulting in declining efficacy of the therapy.

Repeated administration of a recombinant protein can cause acute and chronic immunologic reactions (Schellekens, H., *Nephrol. Dial. Transplant.* 18:1257 (2003); Schellekens, H., *Nephrol. Dial. Transplant.* 20 [Suppl 6]:vi3-vi9 (2005); Purohit et al. *J. Pharm. Sci.* 95:358 (2006)). This loss or "breaking" of tolerance can have serious effects including the development of autoimmune diseases. For example, upon repeated administration of a recombinant protein, tolerance can be broken, and an immune response produced against the recombinant protein may cross-react with the individual's endogenous protein. A mechanism for breaking self-tolerance was demonstrated in transgenic mice immune tolerant for human interferon-alpha 2. When preparations containing aggregates of recombinant human interferon-alpha 2b were administered to the mice, the mice lost tolerance for interferon-alpha 2 in a dose-dependent manner (see Hermeling et al., *J Pharm Sci.* 95:1084 (2006)).

A loss of tolerance to an endogenously produced protein was observed in patients using a preparation of recombinant erythropoietin. Certain preparations of erythropoietin sold under the trademark EPREX (Johnson & Johnson, New Brunswick, N.J.) in Europe were found to break the immune tolerance of patients for their own endogenous erythropoietin, leading to antibody-mediated pure red cell aplasia (PRCA). The exogenous erythropoietin preparation, which was administered to correct a deficiency in red blood cell production, elicited the patient's immune system to produce antibodies that neutralized endogenously produced erythropoietin, causing a complete block in differentiation of red blood cells. The cause of the immune response has been attributed to leachates in the preparation which formed adjuvants with erythropoietin (Boven et al., *Nephrol. Dial. Transplant.* 20 Suppl 3:iii33 (2005)), although other factors, such as aggregates, may also be involved (Schellekens and Jiskoot, *Nature Biotech.* 24:613 (2006)).

Accordingly, new protein engineering and manufacturing strategies are needed to minimize immunogenicity of protein therapeutics and improve the effectiveness of therapy.

SUMMARY OF THE INVENTION

The present invention provides methods for reducing and/or evaluating the immunogenic potential of a therapeutic protein preparation. The present invention further provides pharmaceutical compositions of therapeutic proteins and methods of treatment with the same, the compositions having low immunogenic potential and/or improved efficacy. The invention achieves these goals by evaluating therapeutic protein preparations for subvisible particulates, which can contribute significantly to the overall immunogenic potential of the protein preparation. Further, by maintaining the content of such subvisible particulates below an immunogenic level, the resulting pharmaceutical composition is less likely to result in a loss of tolerance (e.g., upon repeated administration), thereby improving both the safety and efficacy profile of the therapeutic.

Thus, in one aspect, the invention provides a method for evaluating a therapeutic protein preparation for its immunogenic potential. The invention comprises the use of microflow imaging (MFI), or other methodology such as laser diffraction and/or coulter counter, to evaluate particle numbers, sizes, and/or shape in protein samples, and particularly in the subvisible range (e.g., about 0.1 to about 50 microns, or 0.1 to about 10 microns in size). The presence and/or level of such subvisible particles is indicative of an immunogenic preparation.

In accordance with the invention, the therapeutic may be a recombinant protein preparation, and may comprise a monoclonal antibody (which may be chimeric or humanized), an antigen binding domain or single chain antibody, an Fc-domain containing protein (e.g., ENBREL), or other therapeutic protein. Exemplary therapeutic proteins are described herein, and include an interleukin or interferon (e.g., an interferon-alpha, interferon-beta, or interferon-gamma), protein or peptide hormone or growth factor (e.g., insulin, GLP, erythropoietin, GM-CSF, or human growth hormone), clotting factor (e.g., Factor VII, Factor VIII), or enzyme for replacement therapy (e.g., uricase, MYOZYME, phenylalanine hydroxylase, or phenylalanine ammonia lyase). The protein may be produced recombinantly in E. coli, yeast, or mammalian expression system (e.g., CHO cells), and at laboratory scale or manufacturing scale. The protein may be recovered from cells in soluble form, or recovered in insoluble form (e.g., inclusion bodies) and solubilized for evaluation.

The protein preparation, e.g., prior to evaluation and/or treatment to reduce immunogenicity as described herein, may be substantially free of visible aggregates as determined by light obscuration for example, and/or may be substantially free of small subvisible particulates of less than about 0.1 microns in size as determined by, for example, size exclusion chromatography. The protein preparation may be greater than about 90%, or about 95%, or about 99% monomeric protein. In some embodiments, the protein preparation is substantially chromatographically pure. In this context, "substantially chromatographically pure" means that the protein preparation does not contain detectable aggregates by SEC analysis, or contains less than 1% aggregates by weight of protein by SEC analysis.

In another aspect, the invention provides a method for reducing the immunogenicity of a protein therapeutic, and/or formulating a protein therapeutic so as to have low immunogenic potential. The method comprises reducing the amount of particulates in a subvisible range (e.g., about 0.1 to about 50 microns, or about 0.1 to about 10 microns in size). In certain embodiments, the level of such particulates is reduced by high pressure treatment of the protein preparation as described in detail herein. The conditions and/or parameters for high pressure treatment may be selected and/or guided by MFI as well as other techniques disclosed herein, so as to effectively reduce or eliminate the subvisible particulates from the preparation, while favoring properly folded monomeric protein. As disclosed herein, MFI analysis showed particulate aggregates in commercial formulations that were not detectable by SEC or visual inspection, and these solutions were found to be immunogenic in mice. Particulate aggregate doses as low as 1.6 ng/dose broke tolerance in mice and induced immune responses to monomeric protein. When the preparation was treated with high hydrostatic pressure the particulates were reduced to a dose level of 0.02 ng/dose and the immunogenicity was eliminated.

As disclosed herein, a chromatographically pure mGH preparation, which would conventionally be considered aggregate free (and consequently the immunogenicity of the product would conventionally be associated with something other than aggregation), has aggregates present that cannot be detected by chromatography, but are detectable by MFI. As shown herein, these subvisible particulates are immunogenic since, by using high pressure (for example), the subvisible particle content can be decreased along with immunogenicity.

Further, and as disclosed herein, if conventional pressure-treatment (e.g., as guided by SEC analysis) as described in the art is applied to a therapeutic protein preparation such as Enbrel, no change in aggregate level would be detected from the treatment. However, by employing MFI, a different class of aggregates is observed, subvisible particles, that may be reduced via pressure, in a specific pressure window.

Further still, as shown herein, Betaseron also contains subvisible particulates, which was previously unknown.

Thus, in still other aspects, the invention provides pharmaceutical compositions and formulations comprising a therapeutic protein, as well as methods of treatment with the same. The composition contains subvisible (e.g., protein) particulates (e.g., in the range of 0.1 to about 10 microns in size) at below an immunogenic dose. The pharmaceutical composition may be formulated for administration in a manner that, conventionally, has a tendency to induce immune reactions to the therapeutic agent, such as intra-muscular, subcutaneous, or intravenous administration. The pharmaceutical composition in accordance with the invention has low immunogenic potential (even for repeated and/or chronic treatment regimens), may have a better safety and efficacy profile, as well as better shelf stability.

Other objects and aspects of the invention will be apparent from the following detailed description and the appended claims.

DESCRIPTION OF THE FIGURES

FIG. 2 shows an increase in monomer content of Product A and Product B formulations after high pressure treatment.

DETAILED DESCRIPTION OF THE INVENTION

Figure 1:
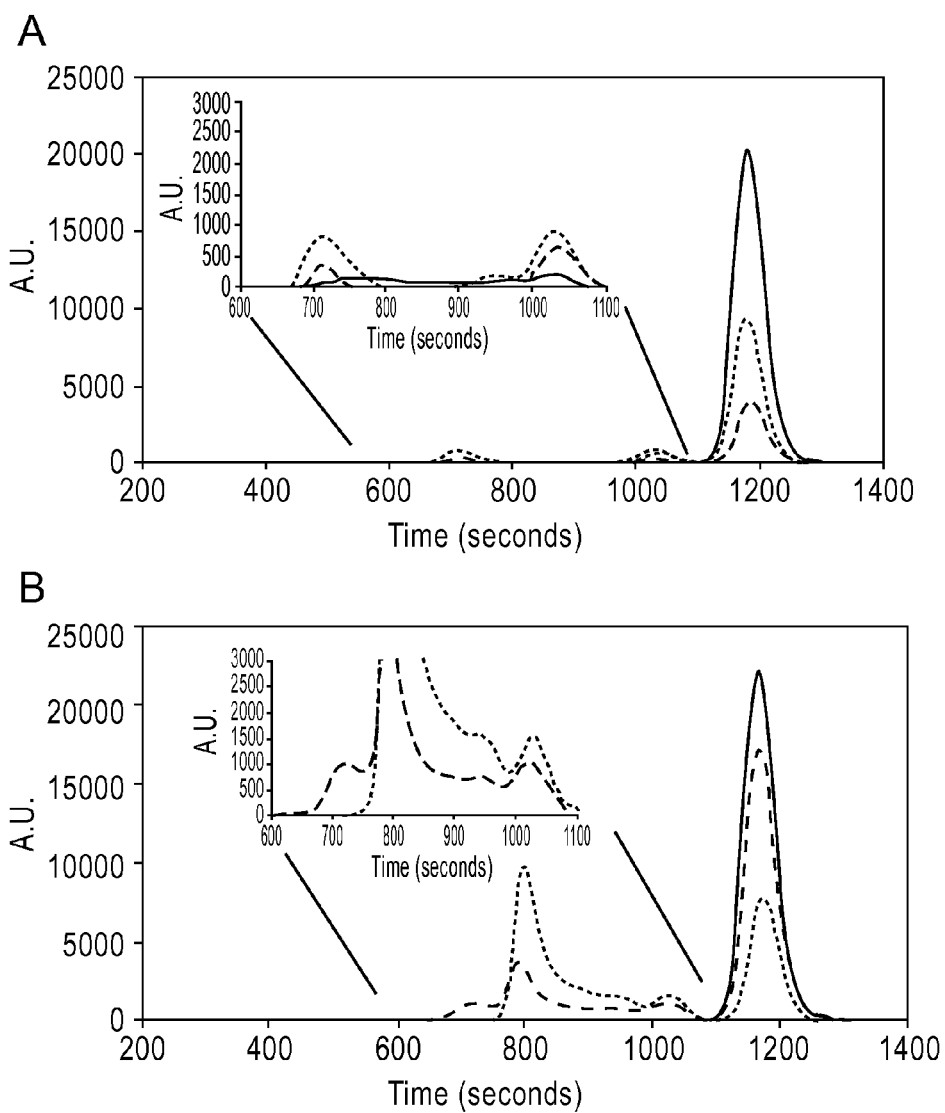
FIG. 1 shows detection of aggregates in Product A and Product B formulations, including after freeze-thaw (FT) and agitation stresses.

The present invention provides methods for reducing and/or evaluating the immunogenic potential of a therapeutic protein preparation. The present invention further provides pharmaceutical compositions and formulations of therapeutic proteins, and methods of treatment with the same, the compositions and formulations having low immunogenic potential and/or improved efficacy.

A "therapeutic protein preparation" is any composition comprising a protein for human or veterinary therapy. The preparation is generally a liquid composition comprising soluble protein, and thus may also comprise one or more pharmaceutically acceptable diluents and/or excipients, such as water, buffer, a pharmaceutically acceptable carrier, and/or a denaturant solution. Components that are not pharmaceutically acceptable, but which are useful in the manufacturing and purification of recombinant protein, may also be present. Such components are removed from the commercial formulation.

The therapeutic protein may be intended for acute or chronic administration, such as, for example, approximately daily, weekly, or monthly administration for a period of months (e.g., at least 6 months) or even years (e.g., 1, 2, or 3 or more years). For example, the therapeutic protein may be indicated for treatment of a chronic disease, such as diabetes mellitus, chronic viral infection (e.g., hepatitis), asthma, COPD, or an autoimmune disorder, such as multiple sclerosis (or other demyelinating disorder) or rheumatoid arthritis, or clotting or enzyme deficiency. The therapeutic protein may be indicated for the treatment of cancer. By providing therapeutic protein compositions having low immunogenic potential, the invention allows prolonged therapy without breaking tolerance and/or without diminishing therapeutic effect.

The protein preparation may be a laboratory sample, bulk pharmaceutical preparation, or individual dosage unit. In some embodiments, the protein preparation is supplied in a formulation suitable for administration, to evaluate its immunogenic potential and/or to further reduce its immunogenic potential as described herein. Alternatively, the therapeutic protein preparation may be at a larger laboratory scale or manufacturing scale (e.g., 10 L, 100 L, 1000 L, 10,000 L, 20,000 L or more), for reduction in its immunogenic potential by removal (or monomerization) of soluble protein aggregates of visible and subvisible sizes (e.g., including subvisible particulates in the 0.1 to 10 micron range), and/or other non-native proteins. The therapeutic protein preparation can then be adjusted to comprise a formulation suitable for administration as a drug with low immunogenic potential.

The protein may be a recombinant protein therapeutic, such as an immunoglobulin (e.g, a monoclonal antibody, which may be chimeric or humanized), an antigen-binding domain or single chain antibody, an Fc-domain containing protein (e.g., ENBREL), or other therapeutic protein. Where the protein comprises an antibody or antibody domain, the antibody or domain may be of any human isotype, such as an IgG isotype. Exemplary therapeutic proteins include a an interleukin or interferon (e.g., an interferon-alpha, interferon-beta, or interferon-gamma), protein or peptide hormone or growth factor (e.g., insulin, GLP, erythropoietin, GM-CSF, or human growth hormone), clotting factor (e.g., Factor VII, Factor VIII), or enzyme for replacement therapy (e.g., uricase, MYOZYME, phenylalanine hydroxylase, phenylalanine ammonia lyase). The therapeutic protein may comprise full length proteins, or functional portions thereof, and may contain modifications known in the art for enhancing activity and/or stability of the molecule.

The recombinant therapeutic protein may be a large protein of one or more than one subunit. For example, the protein may have a size greater than about 500 kDa, 400 kDa, 200 kDa, 100 kDa, 75 kDa, 50 kDa, 40 kDa, 30 kDa, 20 kDa, 10 kDa, 5 kDa, 2 kDa, or 0.25 kDa. In certain embodiments, the recombinant protein comprises a plurality of polypeptide chains, which may optionally be connected by one or more disulfide bonds.

Exemplary therapeutic proteins include interferon-alpha; interferon-alpha 2a (Roferon-A; Pegasys); interferon-beta Ib (Betaseron); interferon-beta Ia (Avonex); insulin (e.g., Humulin-R, Humalog); DNAase (Pulmozyme); Neupogen; Epogen; Procrit (Epotein Alpha); Aranesp (2nd Generation Procrit); Intron A (interferon-alpha 2b); Rituxan (Rituximab anti-CD20); IL-2 (Proleukin); IL-I ra (Kineret); BMP-7 (Osteogenin); TNF-alpha Ia (Beromun); HUMIRA (anti-TNF-alpha MAB); tPA (Tenecteplase); PDGF (Regranex); interferon-gamma Ib (Actimmune); uPA; GMCSF; Factor VII, Factor VIII; Remicade (infliximab); Enbrel (Etanercapt); Betaferon (interferon beta-Ia); Saizen (somatotropin); Erbitux (cetuximab); Norditropin (somatropin); Nutropin (somatropin); Genotropin (somatropin); Humatrope (somatropin); Rebif (interferon beta Ia); Herceptin (trastuzumab); abatacept (Orencia) and Humira (adalimumab); Xolair (omalizumab); Avastin (bevacizumab); Neulasta (pegfilgrastin); Cerezyme (lmiglucerase); and motavizumab. The amino acid sequence and/or structure of such therapeutic proteins are known in the art, and such sequences/structures are hereby incorporated by reference.

The therapeutic protein may contain one or a plurality of glycosylations, or may comprise one or a plurality of PEG strands covalently attached. In other embodiments, the protein therapeutic is a recombinant fusion protein with a half-life extending fusion partner (e.g., albumin or antibody Fc domain).

The protein may be produced recombinantly in an *E. coli*, yeast (e.g., *Pichia*), mammalian cell system (e.g., CHO cells) or other system, and at a manufacturing scale as described. The protein may be recovered in soluble form to evaluate and/or reduce its immunogenic potential as described herein. In other embodiments, the protein preparation is recovered from cells in an insoluble form (e.g., inclusion bodies or precipitate), and subsequently solubilized for evaluating and/ or reducing immunogenic potential as described herein.

The protein preparation, prior to evaluation or treatment to reduce immunogenic potential, may be substantially free of visible aggregates as determined by, for example, light obscuration techniques. Such visible aggregates may be of the size of about 50 microns or larger. The protein preparation may further be substantially free of small soluble protein aggregates (e.g., subvisible aggregates) of less than about 0.2 or about 0.1 microns in size, as determined, for example, by size exclusion chromatography. In other embodiments, the preparation further contains significant amounts of visible aggregates and/or small soluble aggregates, whose level or concentration may be further reduced in accordance with the invention. The protein preparation may be greater than 90%, or 95%, or 97%, or 98%, or 99% monomeric protein, or in some embodiments may be substantially chromatographically pure as determined by SEC.

The protein preparation may contain an immunogenic amount of subvisible particles in the 0.1 to 10 micron range, such as greater than 2 ng/ml, greater than about 5 ng/ml, greater than about 10 ng/ml, greater than about 50 ng/ml, greater than about 100 ng/ml, greater than about 200 ng/ml, or greater than about 500 ng/ml of such subvisible particulates. The immunogenic potential of the preparation may be determined and/or quantified by a method described herein, including the ability of the protein preparation to elicit antibodies in a suitable animal model and/or human population.

In some embodiments, the protein preparation has been resolubilized using chaotrope treatment. Proteins produced in microbial systems are usually insoluble and thus require chaotrope treatment for solubilization and renaturation. Typically, high concentrations of chemicals (e.g., 6M GdnHCl or 8M urea) are required to dissolve the aggregates. After protein dissolution, the chaotrope is diluted to both decrease the protein concentration and allow the protein molecules to return to their native conformation. This process requires denaturation prior to refolding. Because proteins tend to (re) aggregate during refolding, yields of properly folded protein are never 100% in chaotrope-based processes. Accordingly, the invention in certain embodiments, avoids the use of chaotrope treatment.

In order to evaluate the protein preparation for immunogenic potential, the invention employs micro-flow imaging (MFI) to evaluate particle numbers and particle sizes of protein samples, and particularly in the subvisible range (e.g., about 0.1 to about 10 microns in size). The presence and/or level of such subvisible particles is indicative of an immunogenic preparation.

Alternatively, particles in the subvisible range may be detected and/or quantified by laser diffraction or Coulter Counter. The protein preparation may be evaluated by a coulter counter, which can determine particle counts in the 400 nm to 1.7 μm range and is limited by the conductivity of the protein solution. Static light scattering (laser diffraction) can be used to evaluate particle content in 40 nm to 8 mm range, however this technique is generally not considered quantitative and cannot count the number of particles present or the size distribution of the particles.

Even though industry and regulatory agencies are aware of aggregation and have policies and guidelines for their detection in therapeutic protein compositions, some aggregates still go undetected, in-part due to the conventionally accepted analytical techniques. For instance, the USP currently has no guidelines for detection of particles 0.1 to 10 microns in size. Protein aggregates less than 0.1 micron are detected by analytical methods such as size exclusion chromatography, and particles greater than 10 microns are detected by the USP light obscuration <788> technique. There are no clear recommendations for detection of particles greater than about 0.1 micron but less than about 10 microns. This gap in subvisible particle detection leaves an opportunity for protein aggregates to exist in approved commercial products.

More specifically, characterization of aggregates and particulates in final formulations has previously been difficult (Carpenter et al., *Overlooking Subvisible Particles in Therapeutic Protein Products: Gaps That May Compromise Product Quality, J. Pharmaceutical Sciences* 98:4 (2009). SEC-HPLC is the industry standard due to its high throughput and relative robustness. However, particles and aggregates greater than about 0.1 microns can be filtered on the column head, preventing an accurate assessment of all of the aggregates that are present in the solution. More sophisticated methods such as analytical ultracentrifugation can monitor aggregate content and size without a column, however large particles settle too quickly and cannot be quantified. The recent development of micro-flow imaging provides a new technology for visibly measuring the particle content of a solution, and can assess aggregates that previously have not been identified or characterized. During micro-flow imaging, digital microscopy images of a protein solution are taken relative to a blank, and aggregate content is measured by quantifying the size and number of particles present. An apparatus for micro-flow imaging is commercially available from Brightwell Technologies, Inc.

Protein preparations may further be characterized for aggregate or particulate content by one or a plurality of additional analytical techniques selected from the following.

The protein preparation may be evaluated by analytical ultracentrifugation. The use of analytical ultracentrifugation for characterization of aggregation of protein therapeutics is discussed in Philo, J. S., American Biotechnology Laboratory, page 22, October 2003. Experiments that can be performed using analytical ultracentrifugation include sedimentation velocity and sedimentation equilibrium experiments, which can be performed to determine whether multiple solutes exist in a solution (e.g., monomer, dimer, trimer, etc.) and provide an estimate of molecular weights for the solutes.

The protein preparation may be evaluated by size-exclusion chromatography and gel permeation chromatography, which can estimate molecular weights and aggregation numbers of proteins. Such techniques also separate out various protein aggregates. See Wu, C-S. (editor), Handbook of Size Exclusion Chromatography and Related Techniques, Second Edition (Chromatographic Science), Marcel Dekker: New York, 2004 (particularly chapter 15 at pages 439-462 by Baker et al., "Size Exclusion Chromatography of Proteins") and Wu, C-S. (editor), Column Handbook for Size Exclusion Chromatography, San Diego: Academic Press, 1999 (particularly Chapters 2 and 18).

The protein preparation may be evaluated by field flow fractionation, which relies on a field perpendicular to a liquid stream of molecules. Field flow fractionation can be used to analyze and separate aggregated proteins such as protein monomers, dimers, trimers, etc. See Zhu et al., Anal. Chem. 77:4581 (2005); Litzen et al., Anal. Biochem. 212:469 (1993); and Reschiglian et al., Trends Biotechnol. 23:475 (2005).

The protein preparation may be evaluated by light scattering methods, such as methods using laser light scattering (often in conjunction with size-exclusion chromatography or other methods). Light scattering methods can also be used to estimate the molecular weight of proteins, including protein aggregates; see, for example, Mogridge, J., Methods Mol Biol. 261:113 (2004) and Ye, H., Analytical Biochem. 356:76 (2006). Dynamic light scattering techniques are discussed in Pecora, R., ed., Dynamic Light Scattering: Applications of Photon Correlation Spectroscopy, New York: Springer Verlag, 2003 and Berne, B J. and Pecora, R., Dynamic Light Scattering: With Applications to Chemistry, Biology, and Physics, Mineola, N.Y.: Dover Publications, 2000. Laser light scattering is discussed in Johnson, C S. and Gabriel, D. A., Laser Light Scattering, Mineola, N.Y.: Dover Publications, 1995, and other light scattering techniques which can be applied to determine protein aggregation are discussed in Kratochvil, P., Classical Light Scattering from Polymer Solutions, Amsterdam: Elsevier, 1987.

Light obscuration can also be used to measure protein aggregation of the preparation; see Seefeldt et al., Protein Sci. 14:2258 (2005); Kim et al., J. Biol. Chem. 276: 1626 (2001); and Kim et al., J. Biol. Chem. 277: 27240 (2002).

The protein preparation may be evaluated by fluorescence spectroscopy, such as fluorescence anisotropy spectroscopy, which can be used to determine the presence of protein aggregates. Fluorescence probes (dyes) can be covalently or non-covalently bound to the aggregate to aid in analysis of aggregates (see, e.g., Lindgren et al., Biophys. J. 88: 4200 (2005)), US Patent Application Publication 2003/0203403), or Royer, C. A., Methods Mol. Biol. 40:65 (1995). Internal tryptophan residues can also be used to detect protein aggregation by fluorescence; see, e.g., Dusa et al., Biochemistry 45:2752 (2006).

Many methods of gel electrophoresis (e.g., denaturing or non-denaturing PAGE) can be employed to analyze proteins and protein aggregation. Native PAGE (non-denaturing PAGE) can be used to study non-covalently linked aggregates. See, e.g., Hermeling et al. J. Phar. Sci. 95:1084-1096 (2006); Kilic et al., Protein Sci. 12:1663 (2003); Westermeier, R., Electrophoresis in Practice: A Guide to Methods and Applications of DNA and Protein Separations 4th edition, New York: John Wiley & Sons, 2005; and Hames, B. D. (Ed.), Gel Electrophoresis of Proteins: A Practical Approach, 3rd edition, New York: Oxford University Press, USA, 1998.

The protein preparation may be evaluated by gas-phase electrophoretic mobility molecular analysis (GEMMA) (see Bacher et al., J. Mass Spectrom. 36:1038 (2001). A combination of electrophoresis in the gas phase and mass spectrometry provides another method of analyzing protein complexes and aggregates.

Nuclear magnetic resonance spectroscopic techniques can be used to estimate hydrodynamic parameters related to protein aggregation. See, for example, James, T. L. (ed.), Nuclear Magnetic Resonance of Biological Macromolecules, Part C, Volume 394: Methods in Enzymology, San Diego: Academic Press, 2005; James, T. L., Dotsch, V. and Schmitz, U. (eds.), Nuclear Magnetic Resonance of Biological Macromolecules, Part A (Methods in Enzymology, Volume 338) and Nuclear Magnetic Resonance of Biological Macromolecules, Part B (Methods in Enzymology, Volume 339), San Diego: Academic Press, 2001, and Mansfield, S. L. et al., J. Phys. Chem. B, 103:2262 (1999). Linewidths, correlation times, and relaxation times are among the parameters that can be measured to estimate tumbling time in solution, which can then be correlated with the state of protein aggregation. Electron paramagnetic resonance (EPR or ESR) can also be used to determine aggregation states; see, e.g., Squier et al., J. Biol. Chem. 263:9162 (1988).

As disclosed herein, subvisible protein particulates at levels undetectable by standard analytical methods such as size exclusion chromatography and light obscuration can induce immune responses to a self protein or epitope. Specifically, aggregates detected by MFI, which could not previously be detected by SEC-HPLC as they were below the limit of detection, can have significant immunogenic potential.

The present invention provides methods for evaluating protein aggregation, including the level and concentration of subvisible protein particulates in protein preparations. As used herein, a "protein aggregate" or "protein particulate" is defined as being composed of a multiplicity of protein molecules wherein non-native noncovalent interactions and/or non-native covalent bonds (such as non-native intermolecular disulfide bonds) hold the protein molecules together. The aggregates may be soluble or insoluble. Protein aggregates include, but are not limited to, inclusion bodies, soluble and insoluble precipitates, soluble non-native oligomers, gels, fibrils, films, filaments, protofibrils, amyloid deposits, plaques, and dispersed non-native intracellular oligomers.

The protein preparation, which may contain aggregates or protein particulates, may be of high monomer content (for example, at least 80% monomer; at least about 90% monomer; at least about 95% monomer; at least about 97% monomer, at least about 98% monomer, or at least about 99% monomer). Such preparations of high monomer content may still retain significant immunogenic potential due to the presence of even relatively low amounts of subvisible particulates in the range of about 0.1 to 10 microns. In some embodiments, such subvisible particulates are greater than about 0.2 microns, greater than about 0.3 microns, or greater than about 0.4 or 0.5 microns. Such subvisible particulates may be less than about 8 microns, less than about 5 microns, or less than about 3 or 2 microns.

Where such subvisible particulates, or other aggregate content, is detectable via the techniques described herein, the invention provides methods of reducing such particulate or aggregate content.

Aggregates and particulates in some embodiments might be removed by filtration, purification, and refolding. All protein therapeutics are sterile-filtered prior to final formulation (Carpenter, Randolph et al. 2009). However, membrane filtration is not a benign process and exposes proteins to large amounts of surface area (Maa and Hsu 1998). Many proteins are highly surface active, and adsorption to interfaces can lead to protein aggregation. Accordingly, filtration does not always provide a viable option for aggregate removal. Further, with a filtration cutoff of about 0.2 microns or greater, some particulates will escape filtration.

Column-based protein purification processes are commonly employed for aggregate and particulate removal. Unfortunately, yields of process chromatography steps such as size exclusion-, anionic-, or hydrophobic interaction chromatography are rarely 100% as aggregated proteins will typically elute near the native protein. Consequently, the manufacturer typically faces the choice between having a suitable yield or low aggregate burden.

In some embodiments, particulate and/or aggregate content is reduced in the preparation by subjecting the preparation to high-pressure conditions. Generally, the high pressure conditions are selected to not induce aggregation, where the conditions include magnitude of high pressure, duration of high-pressure treatment, protein concentration, temperature, pH, ionic strength, chaotrope concentration, surfactant concentration, buffer concentration, preferential excluding compounds concentration, or other solution parameters as described herein. See WO 2008/033556, which is hereby incorporated by reference in its entirety.

In some embodiments, particulate and/or aggregate content is reduced with high pressure after purification of the protein is completed, that is, after the protein is at the desired purity level for use as a therapeutic (where purity refers to undesired components besides the protein of interest, but not to aggregates or particulate of the protein of interest).

For example, high pressure conditions may be selected to favor properly folded monomeric protein, and to reduce protein particulates (e.g., subvisible particulates) by at least 2 fold, 5 fold, 10 fold, 50 fold, 100 fold, or more. In some embodiments, subvisible particulates are reduced to below a detectable level as determined by MFI.

As used herein, the term "high pressure" means a pressure of at least about 250 bar. The high pressure treatment in accordance with embodiments of the invention may be at least about 250 bar of pressure, at least about 400 bar of pressure, at least about 500 bar of pressure, at least about 1 kbar of pressure, at least about 2 kbar of pressure, at least about 3 kbar of pressure, at least about 5 kbar of pressure, or at least about 10 kbar of pressure. "Atmospheric," "ambient," or "standard" pressure is defined as approximately 15 pounds per square inch (psi) or approximately 1 bar or approximately 100,000 Pascals.

Use of high pressure treatment to reduce subvisible particulate and/or aggregate content in therapeutic protein preparations may extend the shelf life of such preparations, such that the immunogenic potential is reduced or eliminated for a period of time. Thus, in accordance with certain embodiments, high pressure treatment is performed at any time prior to use of the pharmaceutical for human therapy, for example, at least about 3 years before the protein composition is intended to be administered to a individual, at least about 2 years, at least about 1 year, at least about 6 months, at least about 3 months, at least about 1 month, or at least about 2 weeks before the protein composition is intended to be administered to a individual.

Conditions favorable to reduction or elimination of the particulates and/or aggregates in a protein preparation with high monomer content may not be the same or similar to the conditions favorable to maximum yield of protein recovery from a highly aggregated solution. This distinction arises from the common observation that pressure treatment in many solution conditions can induce aggregation and particulate formation of monomeric species (Ferrao-Gonzales, et al. (2000), PNAS 97(12):6445-6450; Kim, et al. (2002), Journal of Biological Chemistry 277(30):27240-27246; Seefeldt, et al. (2005), Protein Science 14(9): 2258-2266; Dzwolak, W. (2006), Biochimica Et Biophysica Acta-Proteins And Proteomics 1764(3): 470-480; Grudzielanek, et al. (2006), Journal Of Molecular Biology 356(2): 497-509; Kim, et al. (2006), High-pressure studies on protein aggregates and amyloid fibrils. Amyloid, Prions, And Other Protein Aggregates, Pt C. 413: 237-253). The selection of such conditions for high pressure should thus be guided by MFI, as well as other techniques, including SE chromatography, light scattering, and/or CD spectroscopy, among others.

High pressure treatment provides an effective process for the removal of protein particulates (including subvisible particulates) and aggregates because it does not involve filtration or purification, which tend to induce aggregation. However, conditions must be identified that do not induce aggregation of the monomer (in any form) while still dissociating aggregates and particulates. High pressure refolding has been identified to occur at conditions within a "pressure-window" that generally favors the native protein conformation. For example, as shown herein, in some embodiments the pressure window for reduction of subvisible particulates may be from about 1000 bar to about 2500 bar, or about 1000 bar to about 2000 bar. In other embodiments, the window may be about 1250 bar to about 2250 bar, or about 1500 bar to about 2000 bar.

In some embodiments, high-pressure treatment is conducted after filtration. While filtration may remove large protein aggregates, as well as particulates above about 0.2 or 0.5 microns in size, subsequent high pressure treatment can reduce the level of particles in the subvisible range that may be induced by the filtration process itself, or which may escape filtration.

Several conditions can be adjusted for optimal treatment of the protein preparation to reduce particulates and aggregates that may result in immunogenicity. Proteins can be treated by high pressure by placing them in a vessel (which can be a high-pressure variable-volume loading device) and then placing the vessel in a high-pressure generator, such as those available from High Pressure Equipment Co., Erie, Pa. High-pressure techniques are described in U.S. Pat. Nos. 6,489,450 and 7,064,192, U.S. Patent Application Publication No. 2004/0038333, and International Patent Application WO 02/062827; the methods for generating high pressure described therein are hereby incorporated by reference herein in their entirety. Certain devices have also been developed which are particularly suitable for refolding of proteins under high pressure; see International Patent Application Publication No. WO 2007/062174, which is hereby incorporated by reference in its entirety. Condition parameters to be adjusted for favorable high pressure treatment are described below.

The concentration of protein may be adjusted for optimal reduction of subvisible particulates. Protein concentrations of at least about 0.1 mg/ml, at least about 1.0 mg/ml, at least about 5.0 mg/ml, at least about 10 mg/ml, or at least about 20 mg/ml may be used. Generally, the protein will be present in a concentration of from about 0.01 or about 0.1 mg/ml to about 50, 250, or 400 mg/ml.

The duration of high pressure treatment may be selected for reduction of subvisible particulates. Generally, high pressure treatment may be conducted for about 15 minutes to about 50 hours, or possibly longer. In some embodiments, the duration of high pressure treatment is up to about 1 week, about 5 days, about 4 days, about 3 days, etc.). Thus, in some embodiments, the duration sufficient to reduce the level of subvisible particulates is from about 2 to about 30 hours, from about 2 to about 24 hours, from about 2 to about 18 hours, or from about 1 to about 10 hours.

The protein preparation may be in aqueous solution conditions to favor properly folder monomeric protein, and to reduce subvisible particulates by high pressure. The solution components may be one or more agents selected from one or more stabilizing agents, one or more buffering agents, one or more surfactants, one or more disulfide shuffling agent pairs, one or more salts, one or more chaotropes, or combinations of two or more of the foregoing. Where such component(s) are not pharmaceutically acceptable, the added component(s) should be removable from the protein preparation prior to administration as a pharmaceutical. Such components may be removed by dialysis.

Exemplary agents include, but are not limited to, buffers (examples include, but are not limited to, phosphate buffer, borate buffer, carbonate buffer, citrate buffer, HEPES, MEPS), salts (examples include, but are not limited to, the chloride, sulfate, and carbonate salts of sodium, zinc, calcium, ammonium and potassium), chaotropes (examples include, but are not limited to, urea, guanidine hydrochloride, guanidine sulfate and sarcosine), and stabilizing agents (e.g., preferential excluding compounds, etc.).

Non-specific protein stabilizing agents act to favor the most compact conformation of a protein. Such agents include, but are not limited to, one or more free amino acids, one or more preferentially excluding compounds, trimethylamine oxide, cyclodextrans, molecular chaperones, and combinations of two or more of the foregoing.

Amino acids can be used to prevent reaggregation and facilitate the dissociation of hydrogen bonds. Typical amino acids that can be used, without limitation, are arginine, lysine, proline, glycine, histidine, and glutamine or combinations of two or more of the foregoing. In some embodiments, the free amino acid(s) is present in a concentration of about 0.1 mM to about the solubility limit of the amino acid, and in some variations from about 0.1 mM to about 2 M. The optimal concentration is a function of the desired protein and should favor the native conformation.

Preferentially excluding compounds can be used to stabilize the native conformation of the protein of interest. Possible preferentially excluding compounds include, but are not limited to, sucrose, hexylene glycol, sugars (e.g., sucrose, trehalose, dextrose, mannose), and glycerol. The range of concentrations that can be use are from 0.1 mM to the maximum concentration at the solubility limit of the specific compound. Exemplary concentrations include those that are consistent with physiological osmolality. The optimum preferential excluding concentration is a function of the protein of interest.

In some embodiments, a stabilizing agent is employed, such as one or more of sucrose, trehalose, glycerol, betaine, amino acid(s), or trimethylamine oxide. In certain embodiments, the stabilizing agent is a cyclodextran. In some embodiments, the cyclodextran is present in a concentration of about 0.1 mM to about the solubility limit of the cyclodextran. In certain embodiments, the stabilizing agent is a molecular chaperone.

A single stabilizing agent maybe be used or a combination of two or more stabilizing agents (e.g., at least two, at least three, or 2 or 3 or 4 stabilizing agents). Where more than one stabilizing agent is used, the stabilizing agents may be of different types, for example, at least one preferentially excluding compound and at least one free amino acid, at least one preferentially excluding compound and betaine, etc.

Buffering agents may be present to maintain a desired pH value or pH range. Numerous suitable buffering agents are known to the skilled artisan and should be selected based on the pH that favors (or at least does not disfavor) the native (monomeric) conformation of the protein of interest. Either inorganic or organic buffering agents may be used.

Thus, in some embodiments, at least one inorganic buffering agent is used (e.g., phosphate, carbonate, etc.). In certain embodiments, at least one organic buffering agent is used (e.g., citrate, acetate, Tris, MOPS, MES, HEPES, etc.). Additional organic and inorganic buffering agents are well known to the art.

A surfactant, a surface active compound, may also be employed to reduce the surface tension of the water. Surfactants may also improve the solubility of the protein of interest. Surfactants may be used at concentrations above or below their critical micelle concentration (CMC), for example, from about 5% to about 20% above or below the CMC. However, these values will vary dependent upon the surfactant chosen, for example, surfactants such as, beta-octylgluco-pyranoside may be effective at lower concentrations than, for example, surfactants such as TWEEN-20 (polysorbate 20). The optimal concentration is a function of each surfactant, which has its own CMC.

Useful surfactants include nonionic (including, but not limited to, t-octylphenoxypolyethoxy-ethanol and polyoxyethylene sorbitan), anionic (e.g., sodium dodecyl sulfate) and cationic (e.g., cetylpyridinium chloride) and amphoteric agents. Suitable surfactants include, but are not limited to deoxycholate, sodium octyl sulfate, sodium tetradecyl sulfate, polyoxyethylene ethers, sodium cholate, octylthioglucopyranoside, n-octylglucopyranoside, alkyltrimethylanmonium bromides, alkyltrimethyl ammonium chlorides, non-detergent sulfobetaines, and sodium bis (2 ethylhexyl) sulfosuccinate. In some embodiments the surfactant may be polysorbate 80, polysorbate 20, sarcosyl, Triton X-100, β-octyl-gluco-pyranoside, or Brij 35.

Where the desired protein contains disulfide bonds in the native conformation it is generally advantageous to include at least one disulfide shuffling agent pair in the mixture. The disulfide shuffling agent pair facilitates the breakage of strained non-native disulfide bonds and the reformation of native-disulfide bonds. Disulfide shuffling agents can be removed by dialysis.

In general, the disulfide shuffling agent pair includes a reducing agent and an oxidizing agent. Exemplary oxidizing agents oxidized glutathione, cystine, cystamine, molecular oxygen, iodosobenzoic acid, sulfitolysis and peroxides. Exemplary reducing agents include glutathione, cysteine, cysteamine, diothiothreitol, dithioerythritol, tris(2-carboxyethyl)phosphine hydrochloride, or β-mercaptoethanol.

Exemplary disulfide shuffling agent pairs include oxidized/reduced glutathione, cystamine/cysteamine, and cysteine/cysteine. Additional disulfide shuffling agent pairs are described by Gilbert H F, (1990) "Molecular and Cellular Aspects of Thiol Disulfide Exchange." Advances in Enzymology and Related Areas of Molecular Biology 63:69-172; and Gilbert H F, (1995) "Thiol/Disulfide Exchange Equilibria and Disulfide Bond Stability," Biothiols, Pt A. p 8-28, which are hereby incorporated by reference in their entirety.

The selection and concentration of the disulfide shuffling agent pair will depend upon the characteristics of the desired protein. Typically the concentration of the disulfide shuffling agent pair taken together (including both oxidizing and reducing agent) is from about 0.1 mM to about 100 mM of the equivalent oxidized thiol, however, the concentration of the disulfide shuffling agent pair should be adjusted such that the presence of the pair is not the rate limiting step in disulfide bond rearrangement.

Chaotropic agents (also referred to as a "chaotrope") are compounds, including, without limitation, guanidine, guanidine hydrochloride (guanidinium hydrochloride, GdmHCl), guanidine sulfate, urea, sodium thiocyanate, and/or other compounds which disrupt the noncovalent intermolecular bonding within the protein, permitting the polypeptide chain to assume a substantially random conformation.

Chaotropic agents may be used in concentration of from about 10 mM to about 8 M. The optimal concentration of the chaotropic agent will depend on the desired protein as well as on the particular chaotropes selected. The choice of particular chaotropic agent and determination of optimal concentration can be optimized by the skilled artisan in view of the teachings provided herein. Chaotropes can be removed from protein preparations by, for example, dialysis before using the protein preparation as a pharmaceutical.

When used in the present methods, it is often advantageous to use chaotropic agents in non-denaturing concentrations to facilitate the dissociation of hydrogen bonds. While a non-denaturing concentration will vary depending on the desired protein, the range of non-denaturing concentrations is typically from about 0.1 to about 4 M. In some embodiments the concentration is from about 0.1 M to about 2 M.

In certain embodiments, guanidine hydrochloride or urea are the chaotropic agents. A single chaotropic agent maybe be used or a combination of two or more chaotropic agents (e.g., at least two, at least 3, or 2 or 3 or 4 chaotropic agents).

Protein solutions can be agitated before and/or during refolding. Agitation can be performed by methods including, but not limited to, ultrasound energy (sonication), mechanical stirring, mechanical shaking, pumping through mixers, or via cascading solutions.

The methods described herein can be performed at a range of temperature values, depending on the particular protein of interest, in order reduce the subvisible particulates (e.g., in the 0.1 to 10 micron range). For example, the protein can be refolded (e.g., disaggregated) at various temperatures, including at about room temperature, about 25° C., about 30° C., about 37° C., about 50° C., about 75° C., about 100° C., or about 125° C. Generally, the temperature will range from about 0 to about 50° C., about 10 to about 37° C., or about 20 to about 30° C.

In some embodiments, the temperature can range from about 20° C. to about 100° C. without adversely affecting the protein of interest, provided that prior to return to room temperature, the mixture is brought to a temperature at which it will not freeze.

Although increased temperatures are often used to cause aggregation of proteins, when coupled with increased hydrostatic pressure increased temperatures can enhance refolding recoveries effected by high pressure treatment, provided that the temperatures are not so high as to cause irreversible denaturation. Generally, the increased temperature for refolding should be about 20° C. lower than the temperatures at which irreversible loss of activity occurs. Relatively high temperatures (for example, about 60° C. to about 125° C., may be used while the solution is under pressure, as long as the temperature is reduced to a suitably low temperature before depressurizing. Such a suitably low temperature is defined as one below which thermally-induced denaturation or aggregation occurs at atmospheric conditions.

Where the reduction in pressure is performed in a continuous manner, the rate of pressure reduction can be constant or can be increased or decreased during the period in which the pressure is reduced. In some variations, the rate of pressure reduction is from about 5000 to 2000 bar/1 sec to about 5000 to 2000 bar/4 days (or about 3 days, about 2 days, about 1 day). In some embodiments, the pressure reduction may be approximately instantaneous, as in where pressure is released by simply opening the device in which the sample is contained and immediately releasing the pressure.

Where the reduction in pressure is performed in a stepwise manner, the process comprises dropping the pressure from the highest pressure used to at least a secondary level that is intermediate between the highest level and atmospheric pressure. The goal is to provide an incubation or hold period at or about this intermediate pressure zone that permits a protein to adopt a desired conformation.

In some embodiments, where there are at least two stepwise pressure reductions there may be a hold period at a constant pressure between intervening steps. The hold period may be from about 10 minutes to about 50 hours (or longer, depending on the nature of the protein of interest). In some embodiments, the hold period may be from about 2 to about 24 hours, from about 2 to about 18 hours, or from about 1 to about 10 hours.

In particular embodiments, constant pressure after the stepwise reduction is from about four-fifths of the pressure immediately prior to the stepwise pressure reduction to about one-tenth of prior to the stepwise pressure reduction. For example, constant pressure is at a pressure of from about four-fifths to about one-fifth, from about two-thirds to about one-tenth, from about two-thirds to about one-fifth of the pressure immediately prior to the stepwise pressure reduction. Where there is more than one stepwise pressure reduction step, the pressure referred to is the pressure immediately before the last pressure reduction {e.g., where 2000 bar is reduced to 1000 bar is reduced to 500 bar, the pressure of 500 bar is one-half of the pressure immediately preceding the previous reduction (1000 bar)).

Where the pressure is reduced in a stepwise manner, the rate of pressure reduction (e.g., the period of pressure reduction prior to and after the hold period) may be in the same range as that rate of pressure reduction described for continuous reduction (e.g., in a non-stepwise manner). In essence, stepwise pressure reduction is the reduction of pressure in a continuous manner to an intermediate constant pressure, followed by a hold period and then a further reduction of pressure in a continuous manner. The periods of continuous pressure reduction prior to and after each hold period may be the same continuous rate for each period of continuous pressure reduction or each period may have a different reduction rate. In some embodiments, there are two periods of continuous pressure reduction and a hold period.

In certain embodiments, each continuous pressure reduction period has the same rate of pressure reduction. In other embodiments, each period has a different rate of pressure reduction. In particular embodiments, the hold period is from about 8 to about 24 hours. In some embodiments, the hold period is from about 12 to about 18 hours.

Commercially available high pressure devices and reaction vessels, such as those described in the examples, may be used to achieve the hydrostatic pressures in accordance with the methods described herein (see BaroFold Inc., Boulder Co.).

Multiple-well sample holders may be used and can be conveniently sealed using self-adhesive plastic covers. The containers, or the entire multiple-well sample holder, may then be placed in a pressure vessel, such as those commercially available from the Flow International Corp. or High Pressure Equipment Co. The remainder of the interior volume of the high-pressure vessel may than be filled with water or other pressure transmitting fluid.

Mechanically, there are two primary methods of high-pressure processing: batch and continuous, each of which may be used in accordance with the invention. Batch processes simply involve filling a specified chamber, pressurizing the chamber for a period of time, and repressurizing the batch. In contrast, continuous processes constantly feed aggregates into a pressure chamber and soluble, refolded proteins move out of the pressure chamber. In both set ups, good temperature and pressure control is essential, as fluctuations in these parameters can cause inconsistencies in yields. Both temperature and pressure should be measured inside the pressure chamber and properly controlled.

There are many methods for handling batch samples depending upon the specific stability issues of each target protein. Samples can be loaded directly into a pressure chamber, in which case the aqueous solution and/or suspension would be used as the pressure medium.

Alternately, samples can be loaded into any variety of sealed, flexible containers, including those described herein. This allows for greater flexibility in the pressure medium, as well as the surfaces to which the mixture is exposed. Sample vessels could conceivably even act to protect the desired protein from chemical degradation (e.g., oxygen scavenging plastics are available).

With continuous processing, small volumes under pressure can be used to refold large volumes the sample mixture. In addition, using an appropriate filter on the outlet of a continuous process will selectively release soluble desired protein from the chamber while retaining both soluble and insoluble aggregates.

Degassing is the removal of gases dissolved in solutions and may be advantageous. Gas is much more soluble in liquids at high pressure as compared to atmospheric pressure and, consequently, any gas headspace in a sample will be driven into solution upon pressurization. The consequences are two-fold: the additional oxygen in solution may chemically degrade the protein product, and gas exiting solution upon repressurization may cause additional aggregation. Thus, samples may be prepared with degassed solutions and all headspace should be filled with liquid prior to pressurization.

In certain aspects, the invention provides pharmaceutical compositions and methods of administration to patients. The compositions, which may be prepared and/or evaluated by the methods of the invention, have low immunogenic potential. Immunogenic potential may be determined by any means known in the art including antibody titers, relative or absolute amount of antibodies present, clinical immune reactions such as inflammation and reactions associated with anaphylaxis (weakness, itching, swelling, hives, cramps, diarrhea, vomiting, difficulty breathing, tightness in the chest, lowered blood pressure, loss of consciousness, and shock), amount of time required for a preparation to provoke detectable antibodies, amount of time required for a preparation to provoke a specified antibody titer, and amount of time required for a preparation to provoke a certain concentration level of antibody. Antibody titers may be measured by any binding or neutralization assay known in the art.

In some embodiments, administration of the pharmaceutical composition does not result in a loss of immune tolerance to repeated administrations or endogenous protein. "Tolerance" or "immune tolerant" as used herein, refers to the absence of an immune response to a specific antigen (e.g., the therapeutic protein) in the setting of an otherwise substantially normal immune system. Tolerance is distinct from generalized immunosuppression, in which all, or part of, immune responses are diminished.

The pharmaceutical compositions in accordance with the invention are formulated so as to have low immunogenic potential. For example, the amount of protein particulates in a subvisible range (e.g., about 0.1 to about 50 microns, or about 0.1 to about 10 microns in size) is below a threshold immunogenic dose as determined, for example, by MFI. As disclosed herein, MFI analysis showed particulate aggregates in commercial formulations that were not detectable by SEC or visual inspection, and these solutions were found to be immunogenic in mice. Particulate doses as low as 1.6 ng/dose broke tolerance in mice and induced immune responses to monomeric protein. When the preparation was treated with high hydrostatic pressure the particulates were reduced to a dose level of 0.02 ng/dose and the immunogenicity was eliminated.

Thus, the invention provides pharmaceutical compositions and formulations comprising a therapeutic protein, as well as methods of treatment with the same. The composition contains subvisible particulates (e.g., in the range of 0.1 to about 10 microns in size) at below about 100 ng/dose, below about 50 ng/dose, below about 10 ng/dose, or below about 2.0 ng/dose. In certain embodiments, the subvisible particulates are below about 1.5 ng/dose, below about 1.0 ng/dose, below about 0.5 ng/dose, below about 0.2 ng/dose, below about 0.1 ng/dose, or below about 0.05 ng/dose. The dose may be of any acceptable volume, such as 1 ml in certain embodiments. Generally, the subvisible particulates are present below an immunogenic threshold so as not to break tolerance, or so as to have a low immunogenic potential upon repeated administration.

The pharmaceutical composition may be formulated for administration in a manner that, conventionally, has a tendency to induce immune reactions to the therapeutic agent, such as intra-muscular, subcutaneous, or intravenous administration. The pharmaceutical composition in accordance with the invention has low immunogenic potential (even for repeated and/or chronic treatment regimens).

The therapeutic composition may be indicated for acute or chronic administration, such as, for example, approximately daily, weekly, or monthly administration for a period of months or even years (e.g., from 2 to 20 years). The protein composition may therefore be administered a plurality of times, including at least three administrations, at least 5 administrations, at least 10 administrations, at least 20 administrations, at least 50 administrations, at least 100 administrations, or more.

The therapeutic protein may be indicated for treatment of a chronic disease, such as diabetes mellitus (e.g., type 1 or type 2), chronic viral infection (e.g., hepatitis A, B, and/or C), or an autoimmune disorder, such as multiple sclerosis or rheumatoid arthritis, clotting deficiency, or enzyme deficiency (e.g., PKU). Other diseases include cancer (e.g., breast cancer, lung cancer, colon cancer), COPD, and asthma. Exemplary protein compositions for use in such indications, which may be evaluated for and/or reduced in their immunogenicity in accordance with the invention, have been described. By providing therapeutic protein compositions having low immunogenic potential, the invention allows prolonged therapy without breaking tolerance and/or without diminishing therapeutic effect.

EXAMPLES

Example 1

Immunogenicity of Aggregates of Recombinant Human Growth Hormone in Mouse Models Summary Aggregation of recombinant therapeutic protein products is a concern due to their potential to induce immune responses. In this example, the immunogenicity of protein aggregates was examined in commercial formulations of recombinant human growth hormone produced by freeze-thawing or agitation, two stresses commonly encountered during manufacturing, shipping and handling of therapeutic protein products. In addition, each preparation was subjected to high-pressure treatment to reduce the size and concentration of aggregates present in the samples. Aggregates existing in a commercial formulation, as well as aggregates induced by freeze-thawing and agitation stresses enhanced immunogenicity in one or more mouse models. The use of high-pressure treatment to reduce size and concentrations of aggregates within recombinant human growth hormone formulations reduced their overall immunogenicity in agreement with the "immunon" hypothesis.

Introduction

Therapeutic proteins are susceptible to aggregation in response to a wide variety of stresses encountered during their manufacture, storage and delivery to patients (1). In turn, aggregates of therapeutic proteins may compromise their safety and efficacy (2-5). The primary safety concern is that aggregates in therapeutic protein products may induce immune responses (6,7), which can have consequences ranging from reduction of product efficacy to patient fatality (8). In extreme cases, parenterally-administered aggregates can induce a severe allergic reaction resulting in anaphylactic shock (9,10). Also, antibodies formed against aggregated protein molecules have the potential to cross-react with the native protein as well (5). This cross-reaction with the native protein may reduce the efficacy of the therapeutic due to a faster clearance of the protein or neutralization of the protein. In addition to the neutralization of the exogenous native therapeutic protein, cases have shown that antibodies raised against recombinant therapeutic human proteins can potentially recognize endogenous human proteins (11-13).

Stresses that frequently provoke protein aggregation such as agitation (14) or freezing (15) are common in the manufacturing and shipping of therapeutic proteins. Agitation (and the resulting exposure of proteins to interfaces such as the air-liquid interface) can result in aggregation during manufacturing, shipping and handling of the product (16). Likewise, protein bulk drug substance is commonly frozen as a storage step in manufacturing process. Additionally, accidental freezing is a risk, particularly during refrigerated storage of therapeutic formulations intended for home use (17). Aggregates produced as a result of different stresses may exhibit different size distributions and their component proteins may contain different secondary and tertiary structures (18), which presumably expose different epitopes and thus potentially provoke different immune responses (19). Previous studies reported the immunogenicity of aggregates formed in interferon α2 formulations (20,21). In the previous study, aggregates were generated by oxidation with hydrogen peroxide, metal-catalyzed oxidization, cross-linking with glutaraldehyde, or exposure to extreme pH. Conditions that result in aggregation via oxidation or exposure to extreme pH may be encountered in industrial processes, but aggregation of therapeutic proteins is more frequently the result of stresses incurred during freeze-thawing and agitation. Thus, the current study focuses on aggregates formed during agitation and freeze-thawing of recombinant human growth hormone (rhGH) and their potential impacts on the immunogenicity of the protein. This example also demonstrates the use of high (~2 kbar) hydrostatic pressures as a method to disaggregate the protein (22,23) with a resultant decrease in immune response.

Due to a lack of sophisticated models and a need for greater understanding of human immune function, pre-clinical predictability of immunogenicity to recombinant human therapeutic proteins is problematic (24). Preclinical immunogenicity studies frequently rely on murine models, in part because mice are relatively inexpensive and low maintenance and are readily available. Naïve mice inherently develop immune responses to foreign proteins (such as therapeutic human proteins). However, murine models may demonstrate enhanced immune responses to more immunogenic samples, and provide a means by which to assess relative immunogenicity of various types of aggregates of a given protein (25). Alternatively, Hermeling et al. (26) recently developed a transgenic mouse model in which the mice were genetically altered to produce a human protein in order to eliminate the innate immune response to that protein, but the relevance of these models to prediction of responses in humans is also still uncertain.

In this study we used three murine models to measure the immunogenic response to protein aggregates produced by agitation or freeze-thawing stresses in two commercial formulations of rhGH. Aggregates were characterized for size and conformation of the component protein molecules. Two murine models used, naïve adult and transgenic, are similar to models used in previous work (25,26). The third murine model is a neonatally-primed model in which mice are sensitized to the rhGH in the neonatal stage (27-29). The neonatally-primed model was chosen to mimic the effect of low concentration pre-existing antibodies to a therapeutic protein. It has been reported that antibodies formed during treatment with a protein therapeutic can be found in the patient in some cases as long as 59 months after discontinuing treatment with that therapeutic (30-32). The presence of antibodies to a therapeutic in a patient after cessation of therapy could pose unknown risks if the patient were to relapse and need additional treatment with that therapeutic.

Materials and Methods

Materials

The two commercial formulations of rhGH Nordiflex® (Novo Nordisk®, Bagsvaerd, Denmark) and Saizen® (Serono, Rockland, Mass.), were purchased from the University of Colorado apothecary, and are hereafter referred to as Product A and Product B, respectively. Sterile water for injection (SWFI) (Hospira, Inc., Lake Forest, Ill.) and 0.9% sodium chloride for injection (Hospira, Inc., Lake Forest, Ill.) were also purchased form the University of Colorado apothecary. Histidine and mannitol were purchased from J T Baker (Phillipsburg, N.J.). Pluronic F-68 was purchased from Spectrum Chemicals (New Brunswick, N.J.). Phenol was obtained from Sigma Chemicals (St Louis, Mo.).

Sample Preparation

For samples produced from the liquid rhGH formulation Product A, 15 mg/1.5 ml vials were used for sample preparation. The rhGH was diluted to a concentration of 1 mg/ml. One of two diluents was used: (1) a solution of identical composition to the product A formulation buffer: 1.13 mg/ml histidine, 3 mg/ml pluronic F-68, 3 mg/ml phenol, 19.3 mg/ml mannitol in SWFI at pH 6.5; (2) the product A formulation without pluronic F-68: 1.13 mg/ml histidine, 3 mg/ml phenol, 19.3 mg/ml mannitol in SWFI at pH 6.5.

For samples generated from the lyophilized rhGH formulation Product B, 8.8 mg vials were used for sample preparation. The lyophilized samples were reconstituted with 3 ml of SWFI resulting in a formulation containing 2.9 mg/ml rhGH, 20.1 mg/ml sucrose and 0.68 mg/ml o-phosphoric acid at pH between 6.5 and 8.5.

To induce the formation of aggregates by agitation, 0.6 ml samples of Product A prepared with diluent 2 or Product B formulation were pipetted into 2 ml polypropylene tubes, which were placed horizontally on a Lab-line titer plate shaker and agitated at approximately 1000 rpm for 72 hours at room temperature. A total of six 2-ml polypropylene tubes containing 0.6 ml of Product A prepared with diluent 2 were pooled together to make one large batch of sample after the 72 hours of agitation. Similarly, the contents of two 2-ml polypropylene tubes containing 0.6 ml of Product B formulation were combined after 72 hours of agitation. The samples processed in this manner are referred to as "agitated Product A" and "agitated Product B."

Samples were freeze-thawed (referred to as "FT Product A" and "FT Product B") by placing 0.75 ml of Product A formulation (diluent 1) or Product B formulation into each of a total of five 2 ml polypropylenes tubes and two 2 ml polypropylenes tubes, respectively. The tubes were placed into liquid nitrogen for one minute to ensure complete freezing of the samples. To thaw the samples, the tubes were suspended in a water bath at 22° C. for ten minutes. The freeze-thaw cycle was repeated 20 times and the appropriate tubes were pooled together to form one batch of FT Product A and one batch of FT Product B.

Samples of Product A formulation and Product B formulation that were not agitated or freeze-thawed were used as controls for immunogenicity studies. These controls are simply referred to as "Product A formulation" and "Product B formulation". The samples were stored at 4° C.

Disaggregation with High-Hydrostatic Pressure

The effects of high hydrostatic pressure on rhGH solutions and solutions containing suspended or soluble rhGH aggregates (agitated, FT, and formulation samples of Product A or Product B) were examined by first placing 1.5 ml of pooled Product A samples and 0.75 ml of pooled Product B samples in Pro-VENT™ Caissons (BaroFold, Inc., Boulder, Colo.). Samples were then loaded into a Pre-EMT™ E150 (BaroFold, Inc., Boulder, Colo.) pressure vessel at room temperature and pressurized with water. Pressure was increased at a rate of 0.1 kbar/minute until a pressure of 2 kbar was achieved. At 2 kbar, the temperature of the high pressure vessel was increased to 70° C. and the samples incubated for 16 hours. High-pressure in conjunction with high-temperatures (65° C.) are necessary to overcome intermolecular hydrogen bonding for proper disaggregation and refolding to occur with human growth hormone (23). Prior to depressurization (0.1 kbar/min), the pressure vessel was cooled to room temperature. Samples of agitated Product A, FT Product A, and Product A formulation treated at high pressure are referred to as "HP agitated Product A", "HP FT Product A" and "HP Product A formulation" respectively. Similar notation is used for high-pressure treated Product B samples.

Chromatographic Analysis of rhGH

Monomer and soluble aggregate levels of rhGH were quantified using size exclusion high performance liquid chromatography (SE-HPLC). A Superdex™ 75 10/300 GL column was used for the SE-HPLC assay. A Beckman Coulter System Gold HPLC with 126 solvent module and Waters autosampler were used online with an ultraviolet detector set at a wavelength of 280 nm. The mobile phase was phosphate buffered saline (PBS) (2 mM KH2PO4, 10 mM NaH2PO4, 3 mM KCl, 140 mM NaCl, pH 7.4), and the flow rate was 0.6 ml/min. The sample injection volume was 50 μl. The samples were kept at 4° C. in the autosampler until injection. Data were collected over a period of 90 minutes. The chromatograms were then imported into GRAMS software (Thermo Electron Corp., Waltham, Mass.) and integrated to determine areas for respective peaks. Peak area percentages are calculated based on areas obtained through integrations of SE-HPLC chromatograms. Peak areas percentages were relative to monomer control peak areas by the following equation:

$$\frac{Area_{peak}}{Area_{monomercontroltotal}} \times 100 \qquad \text{Eq. 1}$$

Peak area percentages of insoluble aggregates determined through following mass balance:

$$\frac{Area_{monomercontroltotal} - Area_{preparationtotal}}{Area_{monomercontroltotal}} \times 100 \qquad \text{Eq. 2}$$

95% confidence intervals were calculated from triplicate injections of each sample on the SE-HPLC.

Analysis of Chemical Degradation Resulting From High-pressure Treatment

Anion exchange chromatography was used to determine deamidation of rhGH before and after pressurization. The method used was adapted from a previously published method (33). An Agilent 1100 HPLC system was equipped with a Tosoh TSK SuperQ-5PW column and running buffers 10 mM potassium phosphate, 10% acetonitrile pH 7.4 (A) and 250 mM potassium phosphate, 10% acetonitrile pH 7.4 (B). The Protein was eluted using a linear gradient of 0-80% B over 45 minutes. Any remaining protein was eluting with 100% B wash step followed by a 7 minute equilibration of 0% B. Absorbance at 280 nm was recorded for 55 minutes.

Matrix-assisted laser desorption ionization spectroscopy (MALDI) was performed on a Voyager System (Applied Biosystems, Foster City, Calif.). The matrix used was α-cyano-4-hydroxycinnamic acid.

SDS-PAGE

SDS-PAGE was performed on pre-cast tris-glycine polyacrylamide gels under reducing and nonreducing conditions. Samples were diluted 2× in Invitrogen Novex® tris-glycine SDS sample buffer (reducing) or Invitrogen Novex® tris-glycine Native buffer (non-reducing) and heated for 5 minutes at 75° C. A total of 4 µg of protein from each sample in a volume of 10 µl was loaded into the wells of the 1.0 mm 4-20% pre-cast Novex tris-glycine gel and allowed to run for 1 hour at lab temperature at 200 volts. The gel was stained with coomassie blue and digital photos were taken.

Particle Sizing

A Beckman Z1™ series COULTER COUNTER® (Fullerton, Calif.) was used to count particles in solutions containing insoluble aggregates. The instrument had the ability to detect particles 1.5 micron and greater. Particles in ranges 1.5-3 micron, 3-6 micron and 6-9 micron were counted five times for each sample. The counts were averaged and 95% confidence intervals were determined.

CD Spectroscopy

Circular dichroism spectra were obtained for the Product B samples (Product B formulation, FT Product B, and agitated Product B) from 190 to 250 nm at 22° C. in a 0.1 cm quartz cuvette using a Jasco J-810 spectropolarimeter. The spectra were an average of three measurements with the buffer spectrum subtracted from the protein spectra. To determine the spectrum for the aggregates in a sample, the CD spectra were corrected by subtracting the monomer spectrum multiplied by the amount of monomer present in the sample. The spectra were then converted to molar ellipticity using a mean residue molecular weight of 115. The percent of alpha helix, beta sheet, turns and random coil were determined for each sample using the SELCON program on the online server DICHROWEB (34). The structural content for triplicate samples was averaged and 95% confidence intervals were determined.

Fluorescence Spectroscopy

Fluorescence emission spectra for soluble samples were taken from 300 to 450 nm using a Horiba Jobin Yuon Fluoromax-3 fluorimeter. Triplicate preparations of Product B formulation, FT Product B and agitated Product B were prepared as described earlier. Samples were at a concentration of 0.04 mg/ml. Wavelengths of 260 nm, 280 nm and 295 nm were used for excitation and slits were set at a 1 nm. An average of 3 scans was taken for each sample and an appropriate buffer spectrum was subtracted from the protein spectrum. The emission scans for aggregate preparations were corrected for monomer signal by subtracting the monomer emission multiplied by the fraction of monomer in each sample. The center of spectral mass (CSM) was calculated for each sample using SigmaPlot® software (Systat Software Inc., San Jose, Calif.). The average CSM and 95% confidence intervals were determined for each preparation (Product B formulation, FT Product B and agitated Product B).

2D-UV Spectroscopy

UV spectra of soluble rhGH samples were taken from 200 to 500 nm in 1 nm intervals with an integration time of 25 seconds on a Hewlett Packard 8453 spectrophotometer. Each sample spectrum was blanked against a buffer spectrum. The aggregated samples were corrected for monomer content by subtracting the monomer spectrum multiplied by the fraction of monomer present in that sample. Second derivatives of spectra were calculated using HP UV-Vis Chemstation software (Hewlett Packard).

Fourier Transform Infrared (FTIR) Spectroscopy

Fourier-transform infrared (FTIR) spectra for native rhGH and insoluble aggregates of rhGH were acquired using a Bomem™ IR spectrometer (Quebec, Canada) and a dTGS (deuterized triglycine sulfate) KBr detector. The aggregates were centrifuged at 5,000 rpm for 5 minutes and the supernatant removed. The aggregates were resuspended in their appropriate buffer (Product A or Product B) at a protein concentration of 20 mg/ml. Native rhGH taken directly from the purchased Product A without dilution at a concentration of 10 mg/ml was used to obtain a FTIR spectrum. A non-diluted sample of Product A was also pressurized using the same protocol as described earlier to obtain a FTIR spectrum of high-pressure treated rhGH. Similarly, a sample of Product B was prepared by reconstitution to a higher concentration (5 mg/ml) and a sample pressurized in order to acquire FTIR spectra of the native rhGH in Product B formulation and high-pressure treated Product B formulation. A variable path length CaF2 cell was used for the measurements. The method used to obtain and analyze spectra has been described previously (35). All mathematical manipulations of spectra were performed in GRAMS software (Thermo Electron Corp., Waltham, Mass.).

Animals

Pregnant C57/BL/6 mice crossed with CH3 mice were obtained from Charles River Laboratories (Raleigh, N.C.). Adult (≥6 weeks of age) female B6C3F1 offspring were used for immunogenicity testing (see below).

To sensitize the B6C3F1 mice (described above) to rhGH for use in the neonatally-primed animal model, 10 µl injections containing 1 µg of rhGH (either Product A formulation or Product B formulation) were administered intraperitoneally in B6C3F1 neonates for 7 consecutive days with the first injection given within 24 hours of birth. These mice were caged together and labeled to separate them from the B6C3F1 naïve model animals. Adult (6 weeks old) female, primed mice were used for immunogenicity testing (see below).

The transgenic mice producing human growth hormone of the strain B6.SJL-Tg(HBB-GH1)420King/J were purchased from Jackson laboratories (Bar Harbor, Maine). The mice were acclimated for at least 7 days before use. Adult (6 weeks old) female mice were used for immunogenicity testing (see below).

Immunogenicity Testing in Animal Models

Once the naïve B6C3F1, neonatally-primed B6C3F1, or transgenic (B6.SJL-Tg(HBB-GH1)420King/J) mice were of age, blood was sampled so that each mouse could serve as its own baseline (Day 0). Once a week for five weeks (Days 0, 7, 14, 21, 28) blood was collected from the retro-orbital venous sinus using 50 µl Fisherbrand microhematocrit capillary tubes. Mice were sedated with Isofluorane inhalant gas throughout the blood collection process. After the blood was collected, each mouse was injected subcutaneously with 10 µg of human growth hormone (Product B or Product A) that had been subjected to one of the six conditions (i.e., agitated, FT, formulation, HP agitated, HP FT or HP formulation) and diluted in saline for injection (Hospira, Lake Forest, Ill., lot 49-521-DK) for a total volume of 100 µl. A total of 8 mice were used in each group. A separate sample of buffer without protein diluted to 100 µl in saline for injection (Hospira, Lake Forest, Ill., lot 49-521-DK) was given in each animal model as a negative control. Additionally, a positive control of 10 µg of ovalbumin in 100 µl of saline for injection (Hospira, Lake Forest, Ill., lot 49-521-DK) was given in the transgenic model. The mice received a total of three injections on days 0, 7 and 14 after the initial blood collection was performed. On day 28 the mice were euthanized by exsanguination and cervical dislocation.

The collected sera were tested for IgG specific antibody response using an enzyme-linked immunoassay (ELISA).

The wells of Immulon 4 High Binding Affinity plates (ISC Bioexpress, Kaysville, Utah) were incubated with 200 µl a diluted monomeric rhGH solution (16 µg/ml) prepared from the Product A or Product B formulations at lab temperature overnight with gentle agitation. The wells were then drained and washed three times with PBS. After the final wash the wells were tapped dry on a paper towel. The wells were then blocked with 200 µl of 1.1 of 1% bovine serum albumin (BSA) in PBS for 1 hour. After application of the blocking solution the wells were washed three times with a solution of PBS. Wells in rows B-H were then loaded with 100 µl of dilution buffer (40 mM HEPES, 10 mM disodium EDTA, 150 mM sodium chloride with 1% BSA and 0.1% triton ×100). The sera were then diluted 1:20 into the dilution buffer and added to the wells in row A. Each plate had two standard curves of known concentration of mouse monoclonal antibody [GH-2] to human growth hormone (Abcam ab9822, Cambridge, Mass.). Using a multichannel pipet, 100 µl of the diluted sera from row A were transferred to the wells in row B. The solution in row B was then mixed by drawing up and expelling 100 µl (5 times) into the wells before transferring 100 µl to wells in row C. The 2× dilutions were continued through row G. The plates were then sealed and allowed to incubate at lab temperature for 30 minutes. Then, the wells were washed 3 times with a solution of 40 mM HEPES, 10 mM disodium EDTA, 150 mM sodium chloride and 0.1% Triton X 100 and tapped dry on a paper towel. The wells were incubated with 100 µl of a horse radish peroxidase conjugated goat anti-mouse IgG (Chemicon, AP308A, Temecula, Calif.) diluted 1:8000 in dilution buffer. After 1 hour, the wells were washed three times with PBS and tapped dry on a paper towel, followed by the addition of 100 µl of 3,3',5,5' tetramethylbenzidine to each well. After 20 minutes, 50 µl of 0.5 M sulfuric acid were added to the wells to stop the reaction. The absorbance was recorded with a Molecular Devices (Sunnyvale, Calif.) "V max" kinetic plate reader at a wavelength of 450 nm and a reference wavelength of 595 nm. The ELISA response was reported in units of ng/ml and was calculated from the average absorbance response on a standard curve multiplied by its dilution factor. The standard curve (r2 value of 0.99) was generated from the standards on each plate using a four-parameter fit in Softmax (Sunnyvale, Calif.) with an antibody concentration range of 1250 ng/ml to 10 ng/ml.

ELISA assays were also performed using Immulon 4 plates coated high-pressure treated rhGH (16 µg/ml) to determine if any differences in immune responses were observed between pressurized and non-pressurized material. Serum was analyzed using the same protocol as described above.

The data were modeled as a general factorial design with 1 response and levels appropriate to the number of groups in each study. Each sample group had eight replicates. The software program Stat-Ease 7.2.1 (Minneapolis, Minn.) was used to conduct a linear analysis of variance (ANOVA). The probability of a [p] between means of groups was compared with a 90% confidence interval. When comparing means, probabilities of [p]<0.1 were significant based on the 90% confidence interval chosen.

Results

Stressing of rhGH Samples

The responses of the Product A and Product B formulations to the various stresses (agitation, freeze-thawing) were different. The agitated Product A samples were cloudy by the end of the 72 hours of agitation whereas the agitated Product B samples were still clear. Similarly, the FT Product A samples began to become cloudy around the 12-15th freeze-thaw cycle; however, the FT Product B never showed signs of cloudiness even after the 20th freeze-thaw cycle. The contrast in aggregates produced in the two samples is believed to be caused by the presence of phenol in formulation A. Phenolic compounds have been shown previously to induce the formation of large insoluble aggregates of rhGH.36

Characterization of Aggregates within rhGH Samples

SE-HPLC was used to determine the aggregation state of each sample type. In Product B formulation, no soluble or insoluble aggregates could be detected (FIG. 1). After application of freeze-thawing or agitation stresses, levels of soluble aggregates increased to 31% and 69% respectively. High pressure treatment of FT Product B and agitated Product B resulted in a substantial increase in monomer levels and soluble dimer aggregate compositions of 4 and 3%, respectively (FIG. 2). The product B formulation sample treated with high pressure had a soluble dimer aggregate content of 1%.

The SE-HPLC chromatograms for the Product A formulation, FT Product A and agitated Product A samples used in the naïve adult and primed naïve animal models are shown in FIG. 1. Product A formulation produced insoluble aggregates after freeze-thawing or agitation that could not be injected onto the SE-HPLC, but could be quantified by mass balance based on the starting protein concentration and that represented in the chromatograms. The Product A formulation contained 2% soluble aggregate, even before being subjected to agitation or freeze-thawing stresses (FIG. 1). From the enlarged portion of the chromatogram it appears that these aggregates are composed mostly of dimer with relatively smaller amounts of higher molecular weight oligomers. The agitated Product A sample contained 12% soluble aggregate and 42% insoluble aggregate. FT Product A had just 5% soluble aggregate and 72% insoluble aggregate. All three Product A preparations (formulation, agitation and FT) exhibited soluble aggregates in the void volume of the Superdex 75 10/300 column (~700 seconds) which indicates aggregates with molecular weights larger than 100,000. After high pressure treatment there was a significant increase in the level of monomer for both the agitated Product A and FT Product A samples, with post-pressure treatment soluble aggregate contents of 7 and 4% respectively (FIG. 2). No insoluble aggregates were detectable in the high pressure treated samples. The high pressure treated Product A formulation (HP formulation) had soluble dimer aggregate content of 2%.

Figure 3:
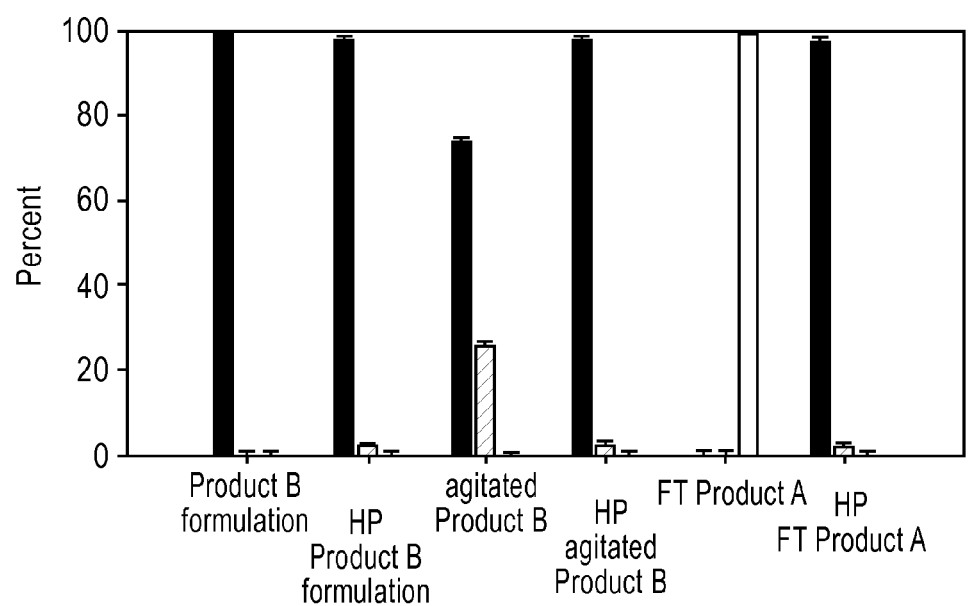
FIG. 3 shows monomer and aggregate levels for samples used in transgenic models.

Samples used in the transgenic animal model were prepared separately from those in the naïve and primed models and resulted similar aggregate types and levels for the different treatments (FIG. 3).

All preparations were analyzed by SDS-PAGE to test for the presence of covalent aggregates (data not shown). No preparation for any formulation contained detectable levels of covalently linked aggregates.

Figure 4:
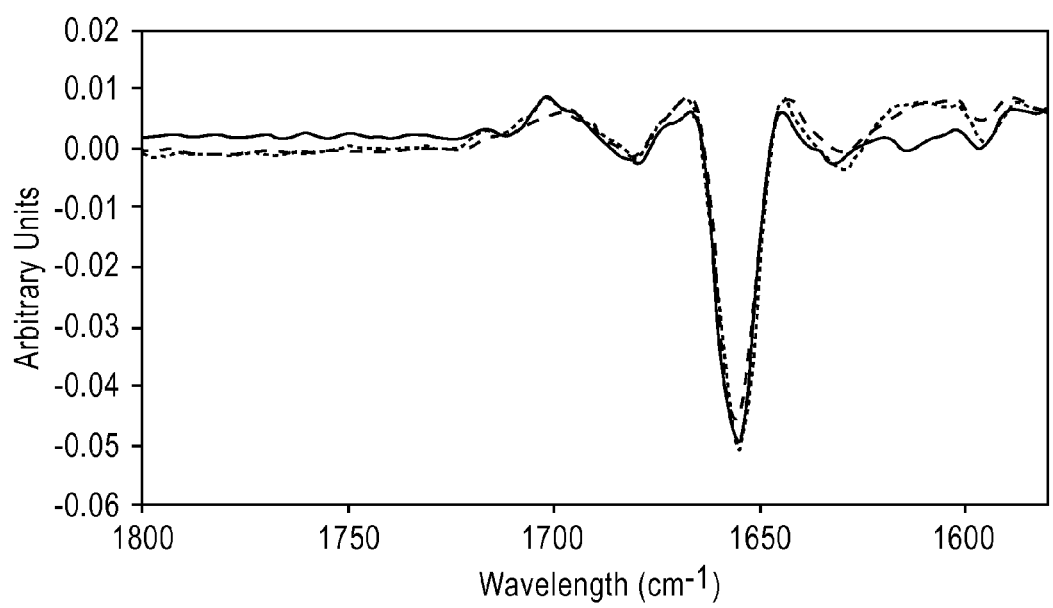
FIG. 4 shows retention of native α-helical content of aggregates produced by agitation and freeze-thawing, as determined by infrared spectroscopy.
Figure 5:
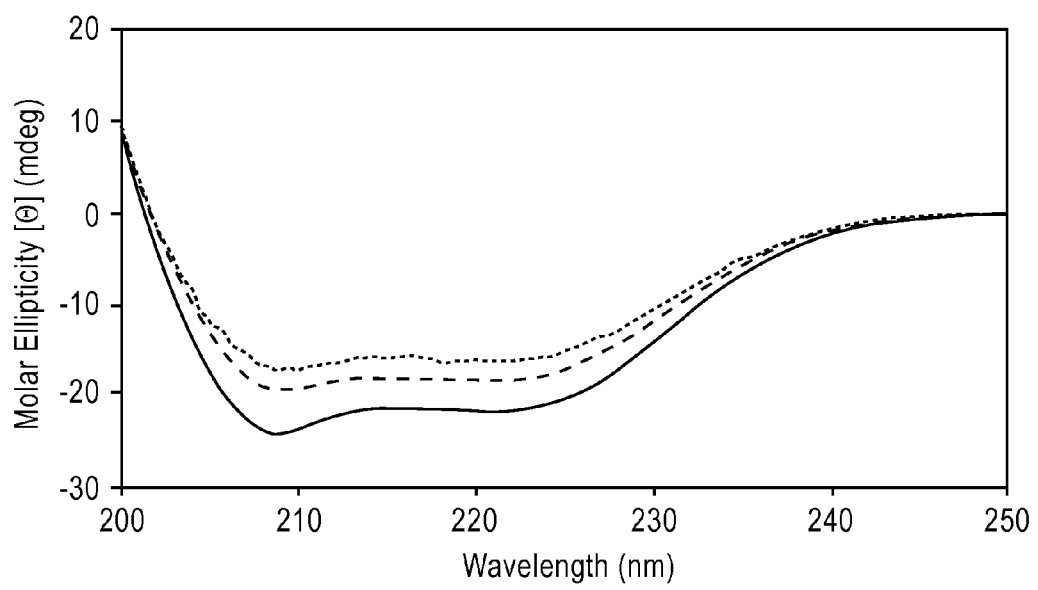
FIG. 5 shows retention of more α-helical content and β-sheet content in freeze-thaw aggregates, as compared to agitated aggregates of Product B formulations, as determined by CD spectroscopy.
Figure 6:
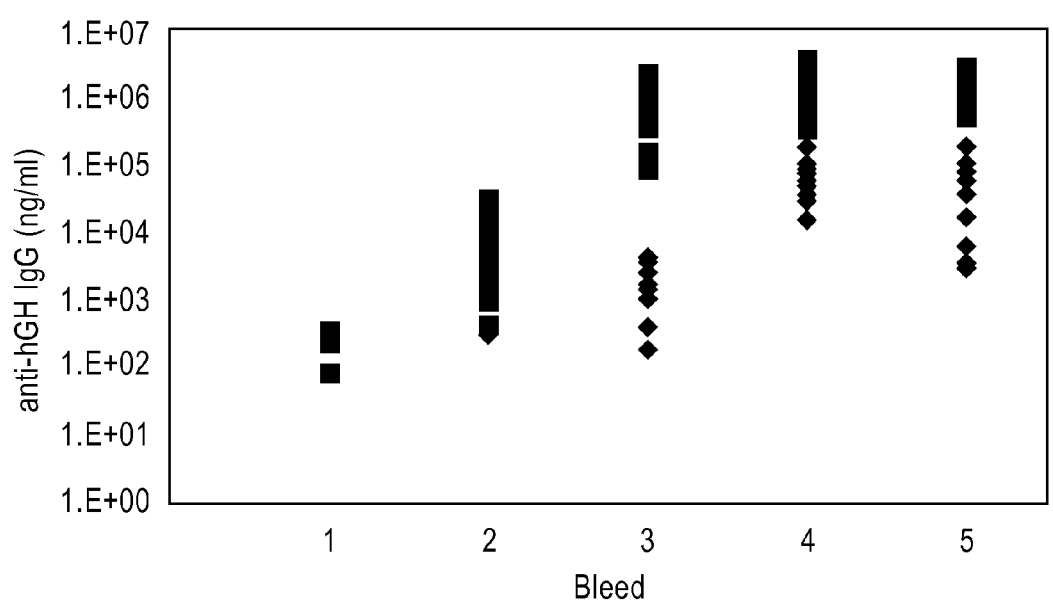
FIG. 6 shows that, in naïve and neonatally-primed mice, maximum levels of hGH antibodies were observed in serum samples collected in week 4.
Figure 7:
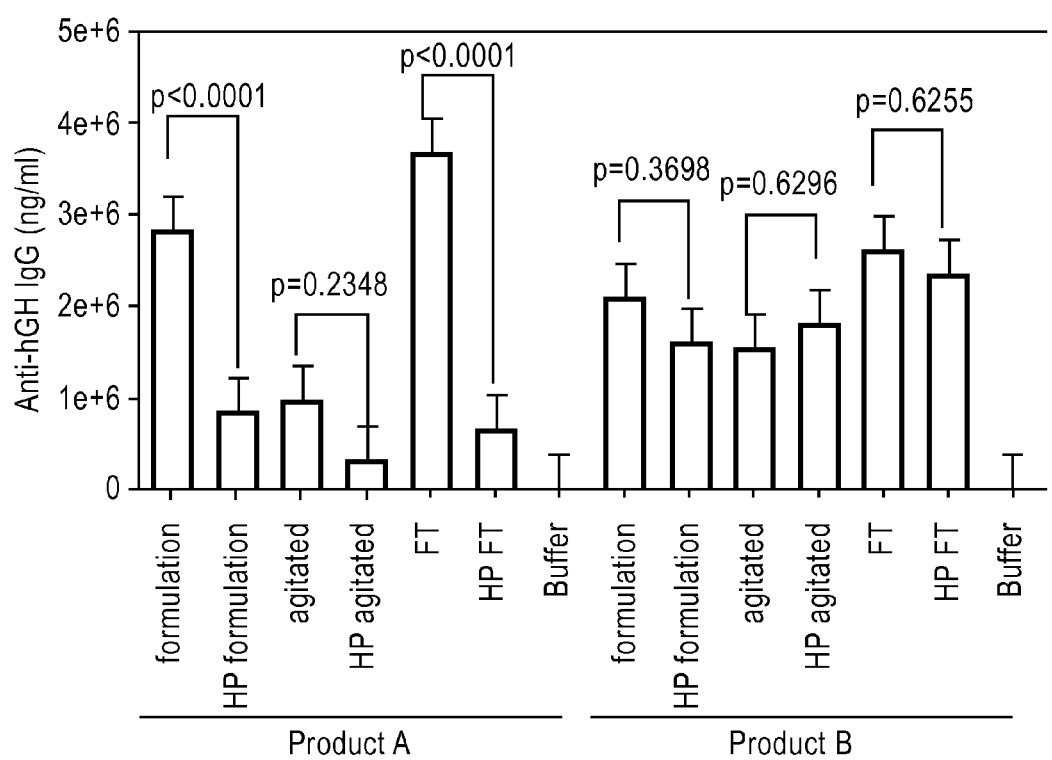
FIG. 7 shows the results of high pressure treatment on immunogenicity of Product A and Product B samples in the neonatally-primed mouse model.

The secondary structures of protein molecules in the insoluble aggregates produced in Product A formulation were determined using infrared spectroscopy. The protein in aggregates produced through agitation and freeze-thawing retain the native alpha-helical secondary structure as shown by the strong signal at 1654 cm$^{-1}$ in FIG. 4. Even though the stresses produce large insoluble aggregates, the overall secondary structure of the component rhGH molecules was minimally perturbed. The secondary structure of Product A and Product B before and after high-pressure treatment was also determined using infrared spectroscopy. No differences were observed in the secondary structures of Product A formulation and its high-pressure treated counterpart even though deamidation occurs during high-pressure treatment (Data not shown). Similarly, pressure treated Product B formulation retained native alpha-helical structure (Data not shown).

The size and number of particles produced in the aggregated preparations of Product A were determined through the use of a Beckman Coulter Counter. The lower limit of detection was 1.5 micron. The FT Product A sample had 97% of its particles in the 1.5-3 micron range and 3% in the 3-6 micron range. There were no detectable particles in the 6-9 micron range for the FT Product A sample. The agitated Product A sample had 85% 1.5-3 micron particles, 14% 3-6 micron particles and 1% 6-9 micron particles. Neither the FT Product A sample nor the agitated Product A sample had particles detectable larger than 9 micron.

Figure 8:
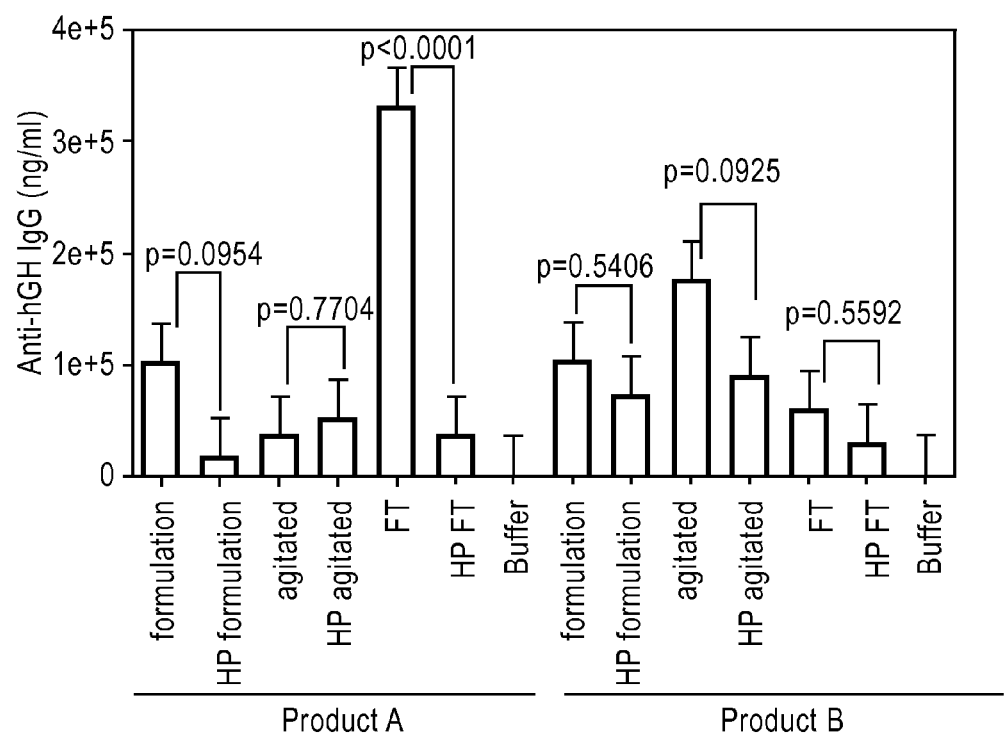
FIG. 8 shows the results of high pressure treatment on immunogenicity of Product A and Product B samples in the naïve adult mouse model.
Figure 9:
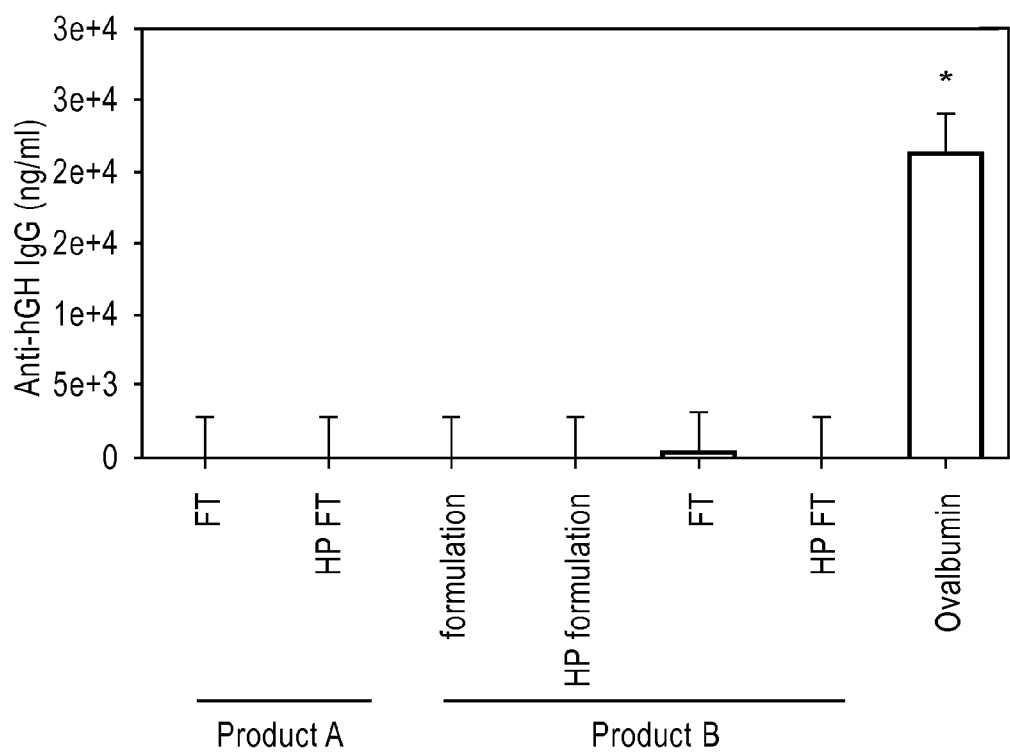
FIG. 9 shows that no immune responses were observed in the transgenic mouse model.

CD spectra were obtained for the soluble Product B preparations that were made in triplicate as a method to analyze the secondary structure of the aggregates (FIG. 5). Light scattering from insoluble aggregates prevented the use of CD spectroscopy for analysis of aggregated Product A samples. The agitated Product B preparation retains more of the alpha helical content than the FT Product B preparation, with compositions of 59% and 54% respectively. The FT Product B has more β-sheet content than the agitated Product B and Product B formulation samples. Both the FT Product B and agitated Product B samples have at least a 2% increase in random coil structures compared to the Product B formulation preparation.

UV scans of the soluble aggregate preparations were used in the characterization of tertiary structure of protein in the stressed Product B samples. Product B samples were made in triplicate and 95% confidence interval were calculated for the mean measurements. Product A samples could not be analyzed with UV due to light scattering caused by the insoluble aggregates. The peak positions in second derivative UV scans from 270-300 nm can be used to describe the tertiary structure of proteins by identifying the microenvironments around tyrosine (Tyr) and tryptophan (Trp) residues (37,38). The spectra for the protein in both the agitated Product B and FT Product B samples had red shifts in the tyrosine peaks with the most predominant shifts observed in spectrum for the FT preparation. Human growth hormone molecules contain eight tyrosine residues. It is clear from the red-shifts observed in the two aggregated samples that one or more tyrosines are more exposed to more apolar environments indicating a change in tertiary structure. The single tryptophan located in an α-helical region of the protein has little change in its microenvironment as evidenced from the constant position of the peak at 293 nm.

Fluorescence spectroscopy also can be used as a method to monitor protein tertiary structure. Different excitation wavelengths can be used to monitor the change in microenvironments of tyrosine and tryptophan residues. Due to light scattering from insoluble aggregates, Product A samples could not be analyzed with fluorescence. Emission scans of the soluble Product B formulation, FT Product B and agitated Product B were recorded at excitations wavelengths of 260, 280 and 295 nm. The wavelength at which the highest fluorescence intensity was observed (λmax) was determined for each emission scan. Each preparation was made in triplicate and 95% confidence intervals were calculated for the mean. Slight red-shifts were observed in λmax for the emission scans of agitated Product B and FT Product B samples at an excitation wavelength of 260 nm indicating slight alterations in the tertiary structure around the tryptophan residue. However, the λmax at an excitation wavelength of 295 nm is not statistically different between the three sample types. Therefore, in agreement with second derivative UV spectroscopy the λmax at an excitation of 295 nm indicates that the aggregates formed in both FT and agitated Product B formulations have minimal change in the α-helix containing the molecule's single tryptophan.

Analysis of Chemical Degradation Resulting from High-Pressure Treatment

Deamidation levels were measured before and after pressurization by anion exchange chromatography. The percentage of deamidated rhGH was found to increase upon pressurization. For Product A the amount of deamidated protein increased from 6 to 60% subsequent to high-pressure treatment. Product B experienced an increase from 2 to 92% after being subjected to high pressure. MALDI experiments detected changes in molecular weight consistent with deamidation in sample subjected to high-pressure treatment. No evidence of other chemical degradation (e.g. oxidation or fragmentation) was observed.

Immunogenicity

In naïve adult and neonatally-primed mice, maximum levels of antibodies were observed in serum samples collected at week 4 (FIG. 6). However, the three animal models generated different levels of antibody production throughout the course of the study. The neonatally-primed mice exhibited anti-hGH IgG levels of mg/ml whereas the naïve adult mice resulted in μg/ml antibody production. The transgenic mice had no detectable anti-hGH IgG antibodies present in any of the treatment groups.

Immune responses were measured using ELISA plates coated with native rhGH or high-pressure treated rhGH. No statistically significant differences of antibody titers were observed between the two types of plates (Data not shown). Therefore, the results that follow are given in titers against native rhGH that was not subjected to high-pressure treatment.

All preparations of Product A and Product B induced an immune response in the neonatally-primed mice. The increased level of anti-hGH IgG, as well as the presence of antibodies at week 1, prior to first inoculation (FIG. 6) in the primed model suggests that sensitization was achieved. The negative control of buffers alone did not induce a response. Even though all animals produced antibodies to human growth hormone, some treatment-based differences were observed. For Product A samples, neither of the stressed samples (agitated Product A, FT Product A) produced a significantly higher immune response than the Product A formulation. While the average immune response of FT Product A was higher than Product A formulation, it can not be stated as statistically different ($p=0.8577$). Product A formulation actually induced a higher immune response than the agitated Product A ($p<0.0001$). The high-pressure treated counterparts of these samples reduced the immunogenicity of the Product A formulation ($p<0.0001$) and FT Product A ($p<0.0001$); however, the agitated Product A treated with high pressure did not statistically reduce the immune response ($p=0.2348$) (FIG. 7). It can also be stated that the high-pressure treated samples of Product A (Product A formulation, agitated Product A, FT Product A) produced immune responses that are not significantly different. The immune responses to stressed Product B preparations (FT, agitated) were not significantly different than that of the Product B formulation. Additionally, when the Product B preparations were treated with high-pressure the immune response did not statistically change (FIG. 7). The immune responses produced from HP Product B formulation, agitated Product B, and FT Product B were not found to be significantly different.

The naïve adult mice produced similar results to the neonatally-primed mice. Again, the negative control of formulation buffer alone for both the Product A and Product B failed to induce an immune response. For Product A preparations, the FT Product A induced a significantly higher immune response than that of the Product A formulation (p<0.0001). The agitated Product A produced a lower average immune response than the Product A formulation, however the responses are not significantly different (p=0.1979). The immune responses for Product A formulation and FT Product A samples were significantly higher than the immune responses generated by their high-pressure treated counterparts (HP Product A formulation, HP FT Product A) (FIG. 8). The immune responses for agitated Product A and HP agitated Product A are not significantly different. Again, similar to the neonatally-primed mice the statistically similar immune responses were generated from all three high-pressure treated Product A preparations and are not significantly different. For the Product B preparations, neither the agitated Product B nor the FT Product B produced statistically different immune responses than that of the Product B formulation (p=0.1545 and 0.3870 respectively). The only high-pressure treated Product B preparation to have a lower immune response than its counterpart was the HP agitated Product B (p=0.0925). The immune responses generated from all high pressure treated Product B samples were not significantly different.

A group of 8 mice were injected with ovalbumin as a positive control and successfully induced antibodies. The positive control produced anti-ovalbumin IgG in the µg/ml levels consistent with the responses in the naïve adult mice indicating that the transgenic animals had normal immune function. However, no immune response to any of the rhGH samples was detected in any of the transgenic animals.

Discussion

Parenteral administration of aggregates of a therapeutic protein can induce immune responses to the monomeric protein. However, little is known about the characteristics of aggregates that are capable of inducing immunogenicity and the mechanism by which they provoke the response (5). B cells can be stimulated to produce antibodies in T-cell independent mechanism that requires an antigen with a repetitive structure (39). Dintzis et al. determined that in order for polymeric antigens to activate B-cells independent of T-cells, the antigens are required to have a minimum number of antigenic receptors (10-20) with a characteristic spacing, which is referred to as "immunon" (40). Dintzis et al. observed that immunons greater than 100 kDa in molecular weight with an epitope spacing of approximately 100 angstroms were successful in inducing B-cell activation (40). The antigenicity of highly ordered repeating epitopes has been confirmed in subsequent studies using virus-like particles (VLPs) with epitope spacing of 50-100 angstroms to activate B cells independent of T cells (41,42). Based on these observations, aggregates of therapeutic proteins with similar sizes, repeating epitope content and retention of near-native protein structure also might serve as antigens to induce an immune response (5,43). Thus, we anticipate that parenteral administration of aggregates that are both sufficiently large (>100 kDa) and that retain significant native structure may result in immunogenicity.

Immune responses may also be co-stimulated by administering adjuvants along with protein antigens (44). Adjuvants attract phagocytic cells such as dendritic cells and enhance their activation (45). Activated dendritic cells can in turn activate T cells into cytotoxic T cell or helper T cells (Th1 and Th2) (46). Adjuvants such as alum increase Th2 response and result in increased B cell activation and consequent antibody production (47). Likewise, large particulate aggregates contaminating a therapeutic product can influence immune responses by enhancing a Th2 responses (25). We speculate that very large insoluble protein aggregates could act in a similar, "self-adjuvanting" fashion. Not only could large insoluble aggregates attract dendritic cells, but there is potential for dendritic cells to take up the aggregate through phagocytosis and cleave the molecule into peptide fragments to be presented on MHCs. Because the aggregate is formed from multiple protein molecules, the peptide fragments presented on MHCs could be consistent with those found on the native monomeric protein, which in turn would enhance the recognition of monomeric protein molecules as antigens.

In our analysis, a commercial formulation of Product A was found to contain 2% soluble aggregates by SE-HPLC. Previous publications have also found Novo Nordisk® rhGH products to contain between 1-5% aggregates (48) and degradation byproducts related to both oxidation and deamidation (49). The Product A formulation contained higher-order oligomers that eluted near the void volume of the sizing column, indicating that the aggregates had molecular weights $\geq 100$ kDa. Previous studies have also shown that aggregates of human growth hormone that eluted in void volume fractions of a Sephadex® gel filtration column were responsible for inducing antibodies in human patients (6). It has been reported that the human growth hormone molecule has 10 epitopes on its outer surface recognizable by monoclonal antibodies (50). Taking into consideration the number of epitopes on the hGH molecule and the sizing results from SE-HPLC, the aggregates found in the Product A formulation sample meet the immunon criteria for B-cell activation. Consistent with these observations Product A induced a substantial immune response in the naïve adult and neonatally-primed mice.

FT Product A induced the highest immune responses observed in this study when administered to naïve and primed mice. This sample had large insoluble aggregates containing native-like secondary structure, as well as presence of smaller soluble aggregates eluting in the dimer and oligomer (MW>100 kDa) volumes of SE-HPLC. We speculate that the large insoluble aggregates could act as adjuvants as well as antigens, thus resulting in the observed high immune response. In the naïve adult mice, FT Product A exhibited an enhanced immune response compared to the Product A formulation (p<0.001). In the neonatally-primed mice, elevated immune responses were seen against both the FT Product A and the Product A formulations, but the differences in responses between the two were not statistically significant (p=0.86). We speculate that because the secondary response shown by neonatally-primed mice does not require adjuvant (51), the presence of large aggregates in the FT Product A formulation did not enhance the immune response in these mice.

After Product A formulation was treated with high pressure, only dimer-size soluble aggregates remained, reducing the molecular weight of aggregates below the ≈100 kDa size required for immunon activity. This sample also resulted in a significantly lower immune response than the untreated counterpart (p<0.0001) in neonatally-primed and naïve mice. Reducing the aggregates with high-pressure treatment and concomitantly the immune response documents that aggregates were responsible for the immune response to Product A formulation.

Similarly, when FT Product A was treated with high pressure the molecular weight and concentrations of aggregates were reduced. The total aggregates content was reduced from 77% to 4% and the remaining aggregation was of dimer-size. No insoluble aggregation was present after high-pressure treatment. Reduction of aggregate molecular weight below 100 kDa and elimination of insoluble aggregates would eliminate the antigenic and adjuvant-like properties that exist in the FT Product A sample. Consistent with this finding is the significantly lower immune response elicited by the HP FT Product A when compared to the immune response of the FT Product A sample ($p<0.0001$) in both the naïve adult and neonatally-primed mice.

The pressure treatment resulted in increased deamidation levels for both formulations. Deamidation levels in Product A increased from 6% to 60%, whereas deamidation levels in Product B increased from 2% to 92% after pressure treatment. The changes in deamidation levels did not correlate with immune response, and equivalent immune responses were detected using ELISA plates coated with either as-received material or pressure treated protein. Mass spectrometry did not detect chemical degradation beyond deamidation. Furthermore, infrared spectroscopy showed that secondary structure of the protein was unchanged by high-pressure treatment. Thus, it appears unlikely that pressure induced conformational or chemical changes in the bulk soluble protein fraction are responsible for the observed changes in immunogenicity before and after pressure treatment.

Agitation and freeze-thawing of Product B did not result in a statistically significant increase in the immune response in either neonatally-primed or naïve mice even though these treatments induced formation of soluble aggregates. This may be due to the lack of an adjuvanting effect because insoluble aggregates were not present. High-pressure treatment of the agitated Product B significantly reduced the amount and size of aggregates as well as the immune response in naïve mice. Again, this finding is consistent with the "immunon" hypothesis as stated previously by eliminating the larger soluble antigenic aggregates.

Some of the samples, such as FT Product B and agitated Product B contained aggregates (31 and 53%, respectively) but did not result in statistically increased immune responses compared to unstressed formulations. The soluble aggregates of the FT Product B sample, which eluted as dimers, trimers and oligomers (>100 kDa) showed a partial loss of native structure in the component protein molecules. Thus, an explanation for the lower immune response to FT Product B could be the loss of native epitopes as well as a lack of insoluble aggregates that with adjuvanting capacity. Likewise, the overall lower immune response of agitated Product A in both the naïve adult and neonatally-primed mice could indicate that the soluble oligomer aggregates present in this preparation did not expose the same native epitopes as those found in the Product A formulation and FT Product A samples. However, due to the low concentration of these aggregates in the samples, the secondary structure of protein within the aggregates could not be characterized.

In the naïve mice, antibody levels were generally in the μg/ml concentration range. In the neonatally-primed mice, however, antibodies were produced at mg/ml concentrations which is consistent with levels of antibodies produced in a secondary response. This is expected since the mice used in the neonatally-primed model had been given injections of the monomeric protein previously. The neonatally-primed mice also had a shorter lag phase in antibody production which is characteristic of a secondary response. It is important to note that previous publications describe injections at a neonatal stage as a means to induce tolerance to a foreign protein rather than sensitization (52-56). However, our protocol successfully primed the mice at a neonatal stage allowing an enhanced immune response when given booster inoculations at an adult stage. Recent studies suggest that tolerance which had previously been defined as the reduced or lack of lymph node proliferation of T-cells (57,58) does not equate to immune tolerance. This is because neonatal injections induce memory T-cells to the antigen which accumulate in the spleen rather than in lymph nodes (58,59).

Interestingly, the transgenic mice failed to produce an IgG immune response to any of the recombinant human growth hormone samples. In contrast, previous studies using interferon α2b transgenic mice showed that tolerance could be broken in response to administration of aggregated protein (21). Important differences between the current study and the previous studies may be related to the natural function and abundance of the respective proteins (5), as well as the mouse strains (60) used to generate the transgenic mice. The current study used the strain B6.SJL-Tg(HBB-GH1)420King/J, which results from the cross breeding of C57BL/6J with SJL strains, whereas the interferon α2b study was based on the strain FVB/N (61). Both the level of transgenic protein produced and the robustness of B-cell repertoire are strain-dependent. The strain used in our study produced human growth hormone ca. 195 ng/ml under control of a sheep hemoglobin betac promoter (62). The levels of human interferon α2b produced in the transgenic line used in previous studies were not published. In addition to the differences in transgenic lines created, the protein that is being produced may have an impact on the resulting immune responses. Both B-cells and T-cells have receptors generated by random chromosomal rearrangements that are specific to antigens that may or may not be encountered through an individual's lifetime (44). In some cases chromosomal rearrangements result in receptors on B-cells and T-cells that identify self molecules. In early development these lymphocytes are deleted from the repertoire in a process referred to as clonal selection (46). It is easier to break tolerance to endogenous proteins found at low levels due to possible incomplete clonal deletion of lymphocytes reactive to these proteins during clonal selection (63). Interferon α is generally expressed at low, nearly undetectable levels (<3 IU/ml) in healthy humans (64,65); whereas growth hormone is a more abundant protein, especially earlier in life with a cyclic production varying from 10-40 μg/L and decreasing to 4 μg/L as adults (66,67). In addition to strain-related differences between the current study and the earlier interferon α2b transgenic study, the different methods used to form aggregates may provide an explanation for the lack of immune response to aggregated rhGH seen in our transgenic mice. The previous study relied on relatively harsh treatments such as metal catalyzed forced oxidation, cross-linking with glutaraldehyde, extreme thermal treatments, and extreme pH to create an aggregate population. These treatments may have created additional and/or more potent epitopes in the aggregates than those of the relatively gentler freeze-thawing and agitation treatments applied in this study.

It is important to note that in this study we used accelerated aggregation techniques to produce aggregates in samples of commercial therapeutic proteins. A therapeutic protein will most likely not experience 20 freeze-thaw cycles or agitation for 72 hours; however, these techniques were necessary to produce enough aggregation to elicit immune response differences in a short time frame. The objective was simply to determine if differences in immunogenicity could be observed from aggregates produced through different stresses. We also chose to only detect immune responses against native monomeric protein. There may have been antibodies not detected that were specific to aggregates of monomeric protein. However, we were most concerned with aggregates that would induce antibodies that have sufficient crossover recognition of the native monomeric protein due to their clinical relevance. Antibodies that only detect aggregates of therapeutic protein may or may not affect the efficacy of the therapeutic product. Antibodies that recognize native monomeric protein are much more of a concern for the safety and efficacy of a therapeutic product. Aggregates with significant native-like structure would more likely produce antibodies that could be cross-reactive with native monomeric protein. Our immunogenicity data and spectroscopic data are consistent with the premise that native-like aggregates could induce cross-reactive antibodies to native monomeric protein.

Conclusions

This study has shown that the immunogenicity of protein aggregates may depend on their size and the manner and solution conditions by which they are produced. Aggregates found in existing commercial formulations were immunogenic in the naïve adult and neonatally-primed mice, as were aggregates generated by freeze-thawing- or agitation-induced stresses applied to the formulations, two types of stresses that are routinely encountered during production, handling, and storage of protein formulations. Further, the stock formulation did not contain aggregates (by SEC), but was immunogenic due to subvisible particulates. Use of high pressure to reduce aggregate levels reduced immune response consistent with the immunon hypothesis.

REFERENCES

The following references are hereby incorporated by reference in their entirety.

1. Chi E Y, Krishnan S, Randolph T W, Carpenter J F 2003. Physical stability of proteins in aqueous solution: Mechanism and driving forces in nonnative protein aggregation. Pharmaceutical Research 20(9):1325-1336.
2. Braun A, Kwee L, Labow M A, Alsenz J 1997. Protein aggregates seem to play a key role among the parameters influencing the antigenicity of interferon alpha (IFN-alpha) in normal and transgenic mice. Pharmaceutical Research 14(10):1472-1478.
3. Schellekens H 2003. The immunogenicity of biopharmaceuticals. Neurology 61(9):S11-S12.
4. Wang W, Kelner D N 2003. Correlation of rFVIII inactivation with aggregation in solution. Pharmaceutical Research 20(4):693-700.
5. Rosenberg A S 2006. Effects of protein aggregates: An immunologic perspective. Aaps Journal 8(3):E501-E507.
6. Moore W V, Leppert P 1980. Role of Aggregated Human Growth-Hormone (Hgh) in Development of Antibodies to Hgh. Journal of Clinical Endocrinology and Metabolism 51(4):691-697.
7. Ratner R E, Phillips T M, Steiner M 1990. Persistent Cutaneous Insulin Allergy Resulting from High-Molecular-Weight Insulin Aggregates. Diabetes 39(6):728-733.
8. Porter S 2001. Human immune response to recombinant human proteins. Journal of Pharmaceutical Sciences 90(1): 1-11.
9. Barandun S, Jeunet F, Kistler P, Isliker H 1962. Intravenous Administration of Human Gamma-Globulin. Vox Sanguinis 7(2):157-&.
10. Ellis E F, Henney C S 1969. Adverse Reactions Following Administration of Human Gamma Globulin. Journal of Allergy 43(1):45-&.
11. Schellekens H 2002. Bioequivalence and the immunogenicity of biopharmaceuticals. Nature Reviews Drug Discovery 1(6):457-462.
12. Gershon S K, Luksenburg H, Cote T R, Braun M M 2002. Pure red-cell aplasia and recombinant erythropoietin. N Engl J Med 346(20):1584-1585.
13. Casadevall N, Nataf J, Viron B, Kolta A, Kiladjian J, Martin-Dupont P, Michaud P, Papo T, Ugo V, Teyssandier I, Varet B, Mayeux P 2002. Pure red-cell aplasia and anti-erythropoietin antibodies in patients treated with recombinant erythropoietin. N Engl J Med 346(7):469-475.
14. Sluzky V, Tamada J A, Klibanov A M, Langer R 1991. Kinetics of Insulin Aggregation in Aqueous-Solutions Upon Agitation in the Presence of Hydrophobic Surfaces. Proceedings of the National Academy of Sciences of the United States of America 88(21):9377-9381.
15. Carpenter J F R T, Chang B S. 2004. Physical damage to proteins during freezing, drying and rehydration. Lyophilization of biopharmaceuticals, ed., New York: Springer. p 423-442.
16. Rathore N, Rajan R S 2008. Current perspectives on stability of protein drug products during formulation, fill and finish operations. Biotechnol Prog 24(3):504-514.
17. Eugene J. McNally C E L. 1999. The Importance of a Thorough Preformulation Study. In McNally E J, editor Protein Formulation and Delivery, ed., New York: Marcel Dekker, Inc. p 111-138.
18. Seefeldt M B, Crouch C, Kendrick B, Randolph T W 2007. Specific volume and adiabatic compressibility measurements of native and aggregated recombinant human interleukin-1 receptor antagonist: Density differences enable pressure-modulated refolding. Biotechnol Bioeng 98(2):476-485.
19. Purohit V S, Middaugh C R, Balasubramanian S V 2006. Influence of aggregation on immunogenicity of recombinant human factor VIII in hemophilia A mice. Journal of Pharmaceutical Sciences 95(2):358-371.
20. Hermeling S, Aranha L, Damen J M A, Slijper M, Schellekens H, Crommelin D J A, Jiskoot W 2005. Structural characterization and immunogenicity in wild-type and immune tolerant mice of degraded recombinant human interferon alpha2b. Pharmaceutical Research 22(12): 1997-2006.
21. Hermeling S, Schellekens H, Maas C, Gebbink M, Crommelin D I A, Jiskoot W 2006. Antibody response to aggregated human interferon alpha2b in wild-type and transgenic immune tolerant mice depends on type and level of aggregation. Journal of Pharmaceutical Sciences 95(5): 1084-1096.
22. St John R J, Carpenter J F, Randolph T W 1999. High pressure fosters protein refolding from aggregates at high concentrations. Proceedings of the National Academy of Sciences of the United States of America 96(23):13029-13033.
23. St John R J, Carpenter J F, Balny C, Randolph T W 2001. High pressure refolding of recombinant human growth hormone from insoluble aggregates—Structural transformations, kinetic barriers, and energetics. Journal of Biological Chemistry 276(50):46856-46863.
24. Bugelski P J, Treacy G 2004. Predictive power of preclinical studies of recombinant therapeutic proteins in animals for the immunogenicity humans. Current Opinion in Molecular Therapeutics 6(1):10-16.
25. Babiuk S, Skowronski D M, De Serres G, HayGlass K, Brunham R C, Babiuk L 2004. Aggregate content influences the Th1/Th2 immune response to influenza vaccine: Evidence from a mouse model. Journal of Medical Virology 72(1):138-142.
26. Hermeling S, Jiskoot W, Crommelin D, Bornaes C, Schellekens H 2005. Development of a transgenic mouse model immune tolerant for human interferon beta. Pharmaceutical Research 22(6):847-851.

27. Adkins B, Bu Y R, Cepero E, Perez R 2000. Exclusive Th2 primary effector function in spleens but mixed Th1/Th2 function in lymph nodes of murine neonates. Journal of Immunology 164(5):2347-2353.
28. Adkins B 1999. T-cell function in newborn mice and humans. Immunol Today 20(7):330-335.
29. Singh R R, Hahn B H, Sercarz E E 1996. Neonatal peptide exposure can prime T cells and, upon subsequent immunization, induce their immune deviation: Implications for antibody vs T cell-mediated autoimmunity. Journal of Experimental Medicine 183(4):1613-1621.
30. Petersen B, Bendtzen K, Koch-Henriksen N, Ravnborg M, Ross C, Sorensen P S 2006. Persistence of neutralizing antibodies after discontinuation of IFN beta therapy in patients with relapsing-remitting multiple sclerosis. Multiple Sclerosis 12(3):247-252.
31. Schellekens H, Casadevall N 2004. Immunogenicity of recombinant human proteins: causes and consequences. Journal of Neurology 251:4-9.
32. Polman C H, Killestein J, Schellekens H 2006. Neutralizing antibodies to interferon-beta may persist after cessation of therapy: what impact could they have? Multiple Sclerosis 12(3):245-246.
33. Cleland J L, Johnson O L, Putney S, Jones A J S 1997. Recombinant human growth hormone poly(lactic-co-glycolic acid) microsphere formulation development. Adv Drug Deliv Rev 28(1):71-84.
34. Whitmore L, Wallace B A 2004. DICHROWEB, an online server for protein secondary structure analyses from circular dichroism spectroscopic data. Nucleic Acids Res 32:W668-W673.
35. Dong A, Huang P, Caughey W S 1990. Protein Secondary Structures in Water from 2nd-Derivative Amide-I Infrared-Spectra. Biochemistry 29(13):3303-3308.
36. Maa Y F, Hsu C C 1996. Aggregation of recombinant human growth hormone induced by phenolic compounds. International Journal of Pharmaceutics 140(2):155-168.
37. Kueltzo L A, Ersoy B, Ralston J P, Middaugh C R 2003. Derivative absorbance spectroscopy and protein phase diagrams as tools for comprehensive protein characterization: A bGCSF case study. Journal of Pharmaceutical Sciences 92(9):1805-1820.
38. Mach H, Middaugh C R 1994. Simultaneous Monitoring of the Environment of Tryptophan, Tyrosine, and Phenylalanine Residues in Proteins by near-Ultraviolet 2nd-Derivative Spectroscopy. Anal Biochem 222(2):323-331.
39. Galanaud P, Crevon M C, Erard D, Wallon C, Dormont J 1976. 2 Processes for B-Cell Triggering by T-Independent Antigens as Evidenced by Effect of Azathioprine. Cell Immunol 22(1):83-92.
40. Dintzis H M, Dintzis R Z, Vogelstein B 1976. Molecular Determinants of Immunogenicity—Immunon Model of Immune-Response. Proceedings of the National Academy of Sciences of the United States of America 73(10):3671-3675.
41. Yang R C, Murillo F M, Delannoy M J, Blosser R L, Yutzy W H, Uematsu S, Takeda K, Akira S, Viscidi R P, Roden R B S 2005. B lymphocyte activation by human papillomavirus-like particles directly induces Ig class switch recombination via TLR4-MyD88. Journal of Immunology 174 (12):7912-7919.
42. Bachmann M F, Rohrer U H, Kundig T M, Burki K, Hengartner H, Zinkernagel R M 1993. The Influence of Antigen Organization on B-Cell Responsiveness. Science 262(5138):1448-1451.
43. De Groot A S, Scott D W 2007. Immunogenicity of protein therapeutics. Trends Immunol 28(11):482-490.
44. Charles A. Janeway P T, Mark Walport, Mark Schlomchik. 2005. Immunobiology: The Immune System in Health. 6 ed., New York: Garland Science Publishing. p 37-101.
45. Doan T, Melvold, R., Viselli, S., Waltenbaugh, C. 2008. Immunology. ed., Baltimore, Md.: Lippincott Williams & Wilkins.
46. Charles A. Janeway P T, Mark Walport, Mark Schlomchik. 2005. Basic Concepts in Immunology. In Lawrence E, editor Immunobiology: The Immune System in Health and Disease, 6 ed., New York: Garland Science Publishing. p 1-36.
47. Friede M, Aguado M T 2005. Need for new vaccine formulations and potential of particulate antigen and DNA delivery systems. Adv Drug Deliv Rev 57(3):325-331.
48. Bristow A F, Jespersen A M 2001. The second international standard for somatropin (recombinant DNA-derived human growth hormone): Preparation and calibration in an international collaborative study. Biologicals 29(2):97-106.
49. Hepner F, Csaszar E, Roitinger E, Pollak A, Lubec G 2006. Massspectrometrical analysis of recombinant human growth hormone Norditropin (R) reveals amino acid exchange at M14_V14 rhGH. Proteomics 6(3):775-784.
50. Strasburger C J 1990. Antigenic Epitope Mapping of the Human Growth-Hormone Molecule—a Strategy to Standardize Growth-Hormone Immunoassays. Acta Paediatrica Scandinavica:82-86.
51. Nakashima I, Kato N 1975. Adjuvant Action of Capsular Polysaccharide of *Klebsiella*-Pneumoniae on Antibody-Response .4. Roles of Antigen and Adjuvant for Induction of Primary and Secondary Antibody-Responses and for Development of Immunological Memory to Bovine Serum-Albumin. Japanese Journal of Microbiology 19(4): 277-285.
52. Gammon G M, Oki A, Shastri N, Sercarz E E 1986. Induction of Tolerance to One Determinant on a Synthetic Peptide Does Not Affect the Response to a 2nd Linked Determinant—Implications for the Mechanism of Neonatal Tolerance Induction. Journal of Experimental Medicine 164(2):667-672.
53. Clayton J P, Gammon G M, Ando D G, Kono D H, Hood L, Sercarz E E 1989. Peptide-Specific Prevention of Experimental Allergic Encephalomyelitis—Neonatal Tolerance Induced to the Dominant T-Cell Determinant of Myelin Basic-Protein. Journal of Experimental Medicine 169(5):1681-1691.
54. Billingham R E, Brent L, Medawar P B 1953. Actively Acquired Tolerance of Foreign Cells. Nature 172(4379): 603-606.
55. Gammon G, Dunn K, Shastri N, Oki A, Wilbur S, Sercarz E E 1986. Neonatal T-Cell Tolerance to Minimal Immunogenic Peptides Is Caused by Clonal Inactivation. Nature 319(6052):413-415.
56. Duclos T W, Kim B S 1977. Suppressor T Cells—Presence in Mice Rendered Tolerant by Neonatal Treatment with Anti-Receptor Antibody or Antigen. Journal of Immunology 119(5):1769-1772.
57. Maverakis E, Beech J T, Wilson S S, Quinn A, Pedersen B, Sercarz E E 2000. T cell receptor complementarity determining region 3 length analysis reveals the absence of a characteristic public T cell repertoire in neonatal tolerance: The response in the "tolerant" mouse within the residual repertoire is quantitatively similar but qualitatively different. Journal of Experimental Medicine 191(4):695-702.

58. Forsthuber T, Yip H C, Lehmann P V 1996. Induction of T(H)1 and T(H)2 immunity in neonatal mice. Science 271 (5256):1728-1730.
59. Adkins B, Bu Y R, Guevara P 2001. The generation of th memory in neonates versus adults: Prolonged primary Th2 effector function and impaired development of Th1 memory effector function in murine neonates. Journal of Immunology 166(2):918-925.
60. Klitgaard J L, Coljee V W, Andersen P S, Rasmussen L K, Nielsen L S, Haurum J S, Bregenholt S 2006. Reduced susceptibility of recombinant polyclonal antibodies to inhibitory anti-variable domain antibody responses. Journal of Immunology 177(6):3782-3790.
61. Beers M M C V. 2008. In Fradkin A, editor, ed.
62. Saban J, Schneider G B, Bolt D, King D 1996. Erythroid-specific expression of human growth hormone affects bone morphology in transgenic mice. Bone 18(1):47-52.
63. Rosenberg A S, Worobec A 2004. A risk-based approach to immunogenicity concerns of therapeutic protein products Part 1 Considering consequences of the immune response to a protein. Biopharm International 17(11):22-.
64. Thavasu P W, Longhurst S, Joel S P, Slevin M L, Balkwill F R 1992. Measuring Cytokine Levels in Blood—Importance of Anticoagulants, Processing, and Storage-Conditions. Journal of Immunological Methods 153(1-2):115-124.
65. Grunfeld C, Kotler D P, Shigenaga J K, Doerrler W, Tierney A, Wang J, Pierson R N, Feingold K R 1991. Circulating Interferon-Alpha Levels and Hypertriglyceridemia in the Acquired-Immunodeficiency-Syndrome. American Journal of Medicine 90(2):154-162.
66. Casanueva F F 1992. Physiology of Growth-Hormone Secretion and Action. Endocrinology and Metabolism Clinics of North America 21(3):483-517.
67. VanCauter E, Plat L 1996. Physiology of growth hormone secretion during sleep. Journal of Pediatrics 128(5):532-537.

Example 2

Aggregates of Recombinant Murine Growth Hormone Break Tolerance

A Model for Adverse Immunogenicity of Therapeutic Proteins

Recombinant therapeutic proteins now comprise front-line clinical treatments for many diseases and disorders. Dozens of therapeutic protein products are approved and marketed and hundreds more are in clinical trials (1). In spite of the clinical efficacy of these products, for many of them a drawback is the risk of adverse immune response (2). Patients that produce neutralizing antibodies as a result of the immune response may experience reduced efficacy of treatment and risk serious complications (3). Furthermore, in some cases the immune response also can neutralize the endogenous counterpart of the therapeutic protein, causing permanent harm or death (4,5). In addition, products of great potential benefit to patients may fail to be approved because of immunogenicity problems arising during clinical trials.

Although the mechanisms by which therapeutic proteins may induce adverse immune responses are not well understood, protein aggregates may play a role (3). Unfortunately, therapeutic proteins aggregate throughout their product life cycle, and proteins are thought to be thermodynamically unstable with respect to aggregation (6). In addition, aggregation may be accelerated by stresses such as freeze-thawing or exposure to the air-water interfaces and other surfaces which are commonly encountered during manufacturing, shipping, storage and delivery to patients (7,8). The characteristics of protein aggregates can vary depending on many factors, including the nature of the initiating stress, solution conditions, protein physicochemical properties, etc (9). For example, exposure to air-water interfaces can sometimes cause the formation of large, soluble oligomers, whereas in other cases insoluble precipitates and/or subvisible particles are formed. Also, the conformation of the protein molecules within aggregates can vary from native-like to greatly perturbed structure (10). Immunogenicity of protein aggregates may depend on the size of aggregates, the structure of protein molecules that make up aggregates and the route of administration (11-13). It has been hypothesized that aggregates may be of sufficient size and also may exhibit repetitive epitopes necessary to induce T cell-independent B cell activation, and the highly ordered, repetitive nature of some protein aggregates may cause the immune system to respond to them as if they were pathogen-associated molecular patterns (PAMPs), thereby inducing innate and adaptive immune responses (3). Furthermore, particulate protein aggregates and protein molecules adsorbed on the surface of foreign microparticles could behave as self-adjuvants (11) enhancing uptake by macrophages and inducing inflammatory co-stimulatory cytokines, leading to strong T-cell dependent immune responses. We hypothesize that aggregates formed as a result of different types of stresses may provoke different levels and types of immune responses.

Proteins also may form aggregates by adsorption to micro- and nanoscopic foreign materials that are commonly found in therapeutic protein products (14). Patients may be exposed to foreign particles that are introduced into therapeutic products during the filling of product containers such as vials or syringes and/or shed from the product containers themselves (15). For example, stainless steel particles are eroded from some types of high-speed filling pumps, and product container/closures can shed particles of glass, silicone oil, rubber and/or tungsten particles into formulations (16). In vaccine formulations, protein molecules typically are adsorbed onto foreign microparticles of materials such as aluminum salt adjuvants in order to stimulate desirable immune responses against foreign proteins (17). Our second hypothesis is that breaking of immune tolerance may result from administration of therapeutic protein molecules adsorbed onto commonly-found foreign microparticles.

Previous studies have used murine models to investigate the immunogenicity of aggregates of recombinant human therapeutic products (11, 13, 18-20). In these studies, parenteral administration of aggregates was often associated with elevated immune responses compared to that noted with the monomeric protein. Because human proteins are non-self to mice, some studies have used transgenic mice to examine breaking of tolerance, whereas others have used naïve mice in which there are innate immune responses to foreign protein and monitored the level of the response. In this study, we used recombinant murine growth hormone (21) (mGH) to test the ability of aggregates of an endogenous protein to break immune tolerance in mice. We investigated the immunogenicity of protein aggregates that were formed as a result of two pharmaceutically-relevant stresses, agitation and freeze-thawing, as well as the immune response to mGH adsorbed onto microparticles of glass or alum. To examine the effects of reduced aggregate content, we applied high hydrostatic pressure to disaggregate aggregates (22) found in untreated control mGH ("stock"), agitated, and freeze-thawed samples. Aggregates were quantified and characterized by size exclusion high performance liquid chromatography (SE-HPLC), micro-flow imaging particle counting and optical spectroscopy methods.

To gain insight into the mechanism(s) through which the aggregates provoke immune responses (e.g., T-cell dependent or T-cell independent pathways), we measured the levels of IgG isotypes produced in the mice.

Materials and Methods

Materials

The mGH was produced and purified as described earlier (21). Alum (Alhydrogel™ aluminum hydroxide made by Brenntag Biosector) was purchased from E. M. Sergeant Pulp & Chemical Co., Inc. (Clifton, N.J.). Glass microparticles were produced from ball milling of syringe barrels (Becton Dickinson, Franklin Lakes, N.J.) as described earlier (14). Saline for injection (Hospira, Inc., Lake Forest, Ill.) was purchased from the University of Colorado apothecary. Goat anti-mouse IgG1, goat anti-mouse IgG2a, goat anti-mouse IgG2b, goat anti-mouse IgG2c, goat anti-mouse IgG3, HRP conjugated rabbit anti-goat IgG, and mouse anti-ovalbumin were all purchased from Abcam (Cambridge, Mass.). 3,3',5,5' tetramethylbenzidine was purchased from KPL (Gaithersburg, Md.). All other reagents were from Fisher Scientific (Pittsburgh, Pa.).

Sample Preparation

The stock sample was stored at 4° C. and was used to prepare all samples of mGH. Aggregates of mGH were formed by freeze-thawing and agitation stresses. The freeze-thaw sample was subjected to 20 freeze-thaw cycles of freezing in liquid nitrogen for 1 minute followed by 10 minute thaw in a 25° C. water bath. The agitated sample was prepared by securing the sample horizontally to a Lab-line titer plate shaker and agitating at approximately 1000 rpm for 4 hours at room temperature. mGH was adsorbed to alum and glass particles by adding appropriate masses of particles to protein solution and subjecting them to end-over-end rotation at 8 rpm for 30 minutes. The mGH was adsorbed to alum at a 1:1 mass ratio. mGH was adsorbed to the glass at a mass ratio of 1:76. All samples were kept at 4° C.

High Pressure Treatment of Samples

The stock, agitated and freeze-thaw samples were each subjected to high hydrostatic pressure to dissociate non-covalent aggregates and refold the protein to the native monomeric state. Samples were placed in heat-sealed BD syringes and pressurized to 200 MPa over 20 minutes in a Pre-EMT150™ pressure vessel (BaroFold Inc., Boulder, Colo., USA) and held at this pressure for 4 hours at room temperature. The samples were then de-pressurized over 20 minutes to atmospheric pressure. The samples were then stored at 4° C. The high pressure treated samples are referred to as "HP stock", "HP agitated" and "HP freeze-thaw".

SE-HPLC

Experiments were conducted using a Superdex™ 75 10/300 GL column on an Agilent 1100 series HPLC system (Agilent Technologies, Inc., Santa Clara, Calif., USA). Isocratic chromatography was performed at room temperature with a flow rate of 0.8 ml/min with 100 mM Acetate 100 mM NaCl pH 4.75 as the mobile phase. UV signal at 280 nm was monitored using the Agilent UV diode array detector for 50 minutes. Samples were centrifuged at 5000 rpm for 5 minutes prior to injection. 100 µl injections of each sample were analyzed in triplicate. The chromatograms were analyzed in GRAMS software (Thermo Electron Corp., Waltham, Mass.) by integration to determine areas for respective peaks. Peak area percentages are calculated based on areas obtained through integrations of SE-HPLC chromatograms. Peak areas percentages were relative to monomer control peak areas by the following equation:

$$\frac{Area_{peak}}{Area_{monomer\ control, total}} \times 100 \quad (1)$$

Peak area percentages of insoluble aggregates determined by mass balance:

$$\frac{Area_{monomer\ control, total} - Area_{preparation, total}}{ARea_{monomer\ control, total}} \times 100 \quad (2)$$

95% confidence intervals were calculated from the triplicate injections of each sample on the SE-HPLC. SE-HPLC analysis was performed throughout the course of the study to ensure no changes in aggregate content.

Particle Analysis

Particle analysis was performed using Micro-Flow Imaging™ on a DPA 4100 (Brightwell Technologies, Inc., Ottawa, Ontario, Canada). Particle free, 0.2 micron filtered water was flushed through the system prior to sample analysis to obtain a clean baseline and optimize illumination. Three 0.5 ml samples of each preparation were analyzed at a flow rate of 0.1 ml/min through a high magnification flow cell using the "set-point 3" configuration, which allows detection of particles 1-50 µm. Prior to analysis, samples were slowly inverted 10 times to ensure suspension of particles. Negative controls of buffer were also analyzed to eliminate any buffer influence to particle detection. The data obtained were number counts per volume per 0.25 micron diameter size bins. Approximate mass of protein in particles was calculated by assuming spherical particles with a density of 1.2 g/ml, between that of protein and water. For ease of data representation, number counts were summed for sizes 1-5 micron, 5-10 micron, 10-15 micron, 15-20 micron, 20-25 micron, 25-30 micron and 30-50 micron ranges.

Infrared Spectroscopy

Infrared spectra for insoluble aggregates of mGH were acquired using a Bomem™ IR spectrometer (Quebec, Canada) and a deuterized triglycine sulfate KBr detector. A variable path length CaF2 cell was used for all the measurements. The solutions were centrifuged at 1,700 g for 5 minutes and the supernatant removed. The aggregates were resuspended in buffer to ensure analysis of aggregates only. Buffer corrections were made by subtracting spectra of buffer or buffer with protein-free particles. The method used to obtain and analyze spectra has been described previously (23). All mathematical manipulations of spectra were performed in GRAMS software (Thermo Electron Corp., Waltham, Mass.).

Front-Face Fluorescence

Front face fluorescence and fluorescence quenching spectroscopy were used jointly to analyze the tertiary structures of native, unfolded and adsorbed mGH. Triplicate samples of 3 ml of each preparation were analyzed in a 3 mm cuvette at a 53° angle from the excitation beam. An excitation wavelength of 295 nm was used in a SLM-Aminico Spectrofluorometer (SLMAminico, Urbana, Ill.). Twelve aliquots of a 7.6 M acrylamide solution were added until a final acrylamide concentration of 0.4 M was obtained. A stirrer was used to prevent settling of particles during analysis. Fluorescence intensities were recorded for 300-380 nm at a scan rate of 0.95 nm/s. All samples were temperature controlled to 25° C.

during analysis. Measured fluorescence emissions were corrected for dilution and inner filter effects when appropriate. Buffer corrections were made by subtracting the spectra of buffer or protein-free particle suspension. Stern-Volmer plots were used to analyze the data using the relationship:

$$\frac{F_0}{F} = 1 + K_{SV}[Q] \qquad (3)$$

In equation (3), $K_{sv}$ is the Stern-Volmer constant (M-1). $F_0$ and F are fluorescence intensities in the absence and presence of different concentrations of quencher Q, respectively. [Q] is the acrylamide concentration (M).

Immunogenicity Testing in Animals

All samples were tested in adult (≥6 weeks of age) CB6F1 mice for immunogenicity. At the start of the study, Day 0, blood was obtained retro-venous orbitally from the mice so that each mouse served as its own baseline. Groups of 8 mice were then given subcutaneous injections of 2 µg of mGH diluted in saline for injection five days a week for three weeks (Days 0-4, Days 7-11, Days 14-18). In addition to the mGH samples, one negative control of buffer alone and a positive control of ovalbumin were injected in groups of mice. The mice were bled again retro-venous orbitally on days 7, 21 and 35 and given 5 additional subcutaneous injections of 2 µg of mGH as a booster on days 35-39. Mice were bled on days 42 and 49 to monitor any secondary responses.

The collected sera were tested for IgG1, IgG2a, IgG2b, IgG2c and IgG3 specific antibody response using an enzyme-linked immunoassay (ELISA). The wells of Immulon 4 High Binding Affinity plates (ISC Bioexpress, Kaysville, Utah) were incubated with 100 µl of diluted stock (10 µg/ml) 100 µl of ovalbumin standard (10 µg/ml) at lab temperature overnight with gentle agitation. The wells were then drained and washed three times with PBS containing 0.05% tween 20. After the final wash the wells were tapped dry on a paper towel. The wells were then blocked with 300 µl of 2% bovine serum albumin (BSA) in PBS for 1 hour. After application of the blocking solution the wells were washed three times with a solution of PBS containing 0.05% tween 20. Wells in rows B-H were then loaded with 50 µl of dilution buffer (1% BSA in PBS). The sera were then diluted 1:20 into the dilution buffer and added to the wells in row A. Each plate had two standard curves of known concentration of mouse monoclonal antibody to ovalbumin (Abcam ab17291, Cambridge, Mass.). Using a multichannel pipet, 50 µl of the diluted sera from row A were transferred to the wells in row B. The solution in row B was then mixed by drawing up and expelling 50 µl (5 times) into the wells before transferring 50 µl to wells in row C. The 2× dilutions were continued through row G. The plates were then sealed and allowed to incubate at lab temperature for 60 minutes. Then, the wells were washed five times with a solution of 0.05% tween 20 in PBS and tapped dry on a paper towel. The wells were incubated with 50 µl of a goat polyclonal specific to mouse IgG1 (Abcam, ab9165) mouse IgG2a (Abcam ab9163), mouse IgG2b (Abcam, ab9164), mouse IgG2c (Abcam, ab9168) or mouse IgG3 (Abcam, ab9166) diluted 1:8000 in dilution buffer. After 1 hour, the wells were washed five times with 0.05% tween 20 in PBS and tapped dry on a paper towel. The wells were subsequently incubated with 50 µl of horse radish peroxidase conjugated rabbit polyclonal to goat IgG (Abcam, ab6741) diluted 1:5000 in dilution buffer for 60 minutes. The plates were then washed five times with 0.05% tween 20 in PBS and tapped dry, followed by the addition of 50 µl of 3,3',5,5' tetramethylbenzidine to each well. After 20 minutes, 50 µl of 0.5 M sulfuric acid was added to the wells to stop the reaction. The absorbance was recorded with a Molecular Devices (Sunnyvale, Calif.) "V max" kinetic plate reader at a wavelength of 450 nm and a reference wavelength of 595 nm. The ELISA response was reported in units of ng/ml and was calculated from the average absorbance response on a standard curve multiplied by its dilution factor. The standard curve (r2 value of 0.99) was generated from the standards on each plate using a four-parameter fit in Softmax (Sunnyvale, Calif.) with an antibody concentration range of 1250 ng/ml to 10 ng/ml.

Statistical Analysis of Antibody Responses

The data were analyzed for statistical differences using a one tailed t test with variances unknown and not necessarily equal. An F test was performed to determine that the variances were different among sample groups. Each group had a sample size of eight. Microsoft Excel was used to calculate p values. The probability of a [p] between means of groups was compared with a 90% confidence interval. When comparing means, probabilities of [p]<0.1 were significant based on the 90% confidence interval chosen.

Results

Figure 14:
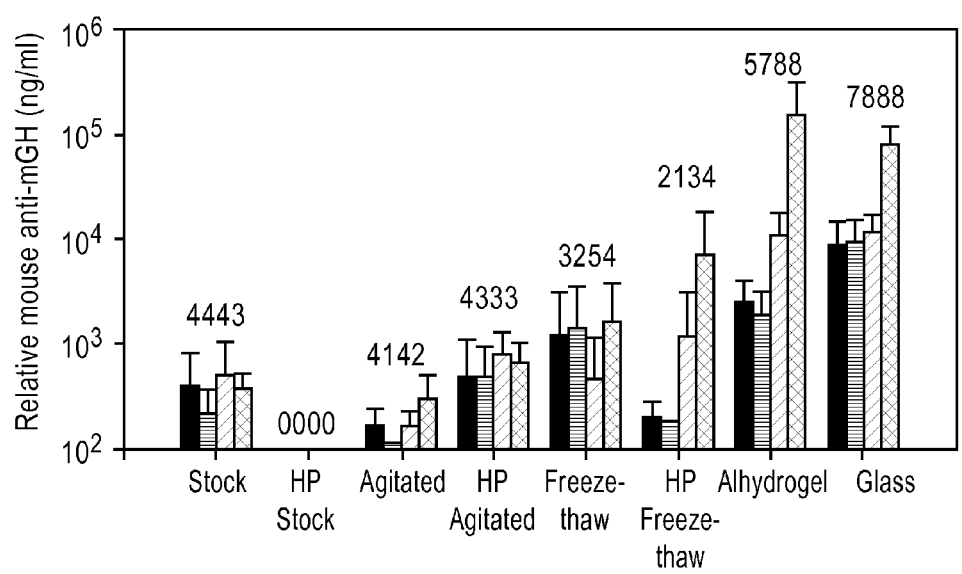
FIG. 14 shows IgG1 antibody production for each mGH preparation. Antibody responses from bleeds from days 21, 35, 42 and 49 are represented as black (■), medium grey (▨), dark grey (▩) and light grey (▤) bars respectively. Only positive mice were averaged. Error bars represent 95% confidence intervals. Numbers above bars indicate number of positive mice.

Isotype responses to mGH aggregates. IgG isotypes (IgG1, IgG2a, IgG2b, IgG2c and IgG3) were assayed by ELISA. No antibodies against untreated control mGH (stock) were detected until day 21. Aggregates of mGH most frequently provoked IgG1 isotype responses. Samples containing mGH adsorbed on glass or alum were the only samples to break tolerance in all 8 mice in their respective groups. Injections of glass- and alum-adsorbed samples caused higher IgG1 responses than all other samples. The IgG1 responses induced by glass and alum preparations were not different from one another (p=0.441). The other mGH samples were not able to break tolerance in all the animals in their group. IgG1 antibody responses provoked by stock, agitated, HP agitated, freeze-thaw, and HP freeze-thaw samples are not significantly different from one another. See FIG. 14.

Figure 15:
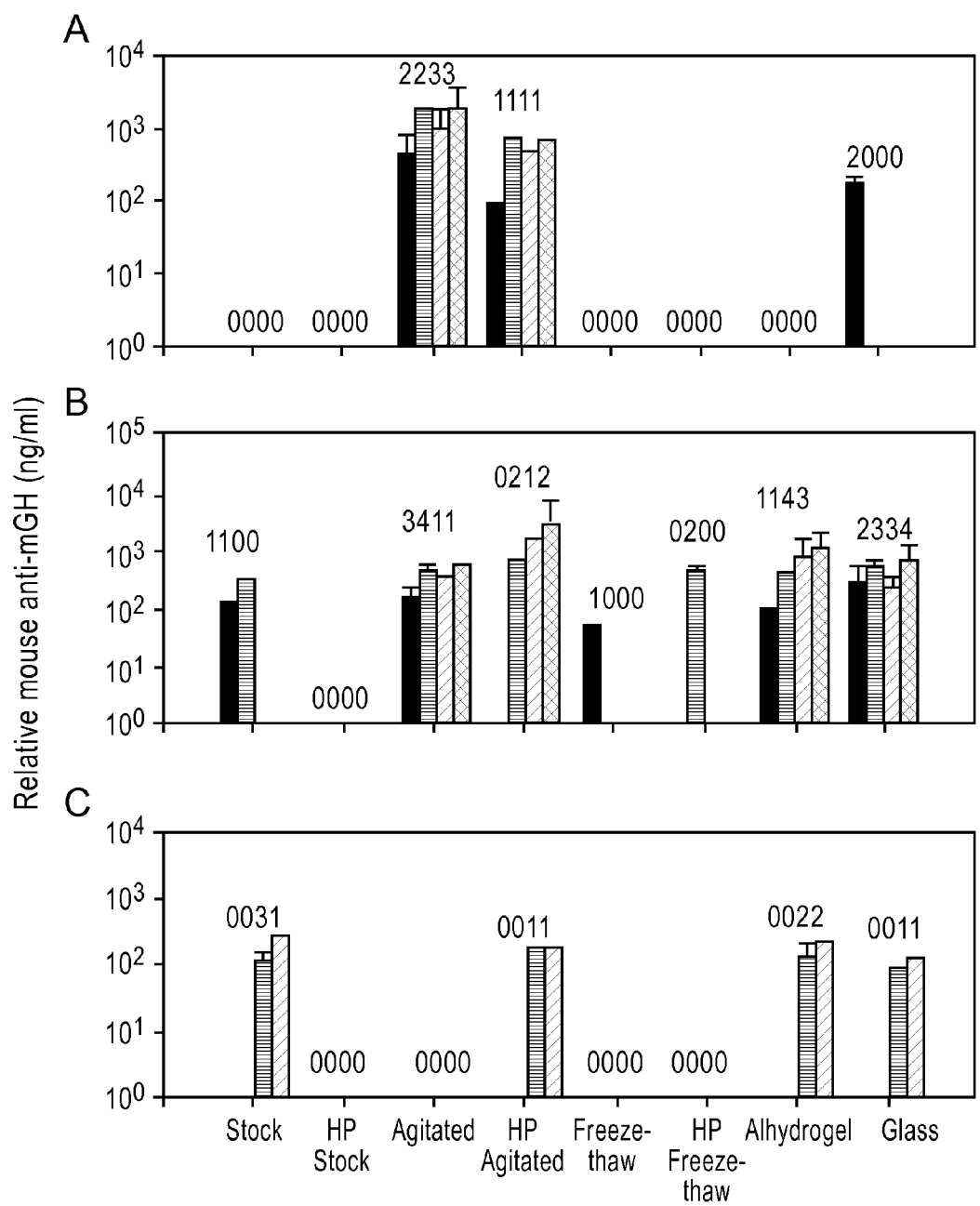
FIG. 15 shows IgG2 antibody production for each mGH preparation. Results for IgG2a, IgG2b and IgG2c are shown in graphs A, B and C respectively. Antibody responses from bleeds from days 21, 35, 42 and 49 are represented as black (■), medium grey (▨), dark grey (▩) and light grey (▤) bars respectively. Only positive mice were averaged. Error bars represent 95% confidence intervals. Numbers above bars indicate number of positive mice.
Figure 16:
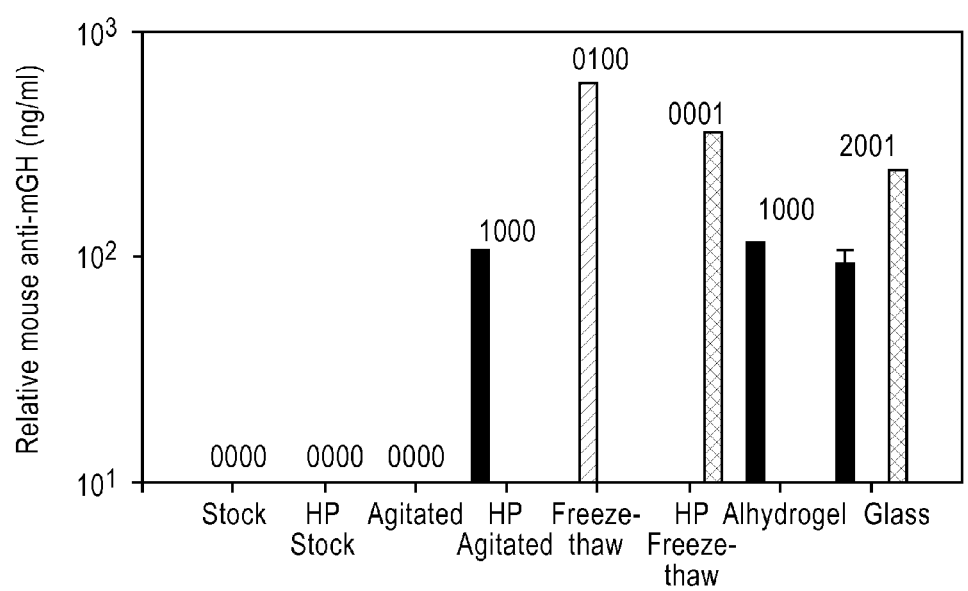
FIG. 16 shows IgG3 antibody production for each mGH preparation. Antibody responses from bleeds from days 21, 35, 42 and 49 are represented as black (■), medium grey (▨), dark grey (▩) and light grey (▤) bars respectively. Only positive mice were averaged. Error bars represent 95% confidence intervals. Numbers above bars indicate number of positive mice.

The agitated mGH sample caused a higher IgG2a response compared to all other mGH samples except its high-pressure treated counterpart. FIG. 15. For all mGH treatments, IgG2b isotype responses were observed in more mice than were IgG2a or IgG2c responses. However, mGH adsorbed to glass was the only sample to produce statistically higher IgG2b responses, and only compared to stock, HP stock, freeze-thaw and HP freeze-thaw samples. The IgG2c response caused by the stock preparation was higher than those resulting from HP stock, freeze-thaw, and HP freeze-thaw samples; however this statistical difference disappeared by the 6th bleed. The IgG2c response produced by mGH adsorbed to alum was higher than responses from HP stock, agitated, freeze-thaw and HP freeze-thaw and this difference was magnified in the responses measured in the serum from the 6th bleed (p=0.085). There were no statistical differences in IgG3 responses between any of the mGH preparations for the serum samples from bleed 5. FIG. 16.

Immune response to high-pressure treated samples. Although the stock mGH was immunogenic with 4 out of 8 mice developing IgG1 antibodies against mGH, the high-pressure treated stock sample did not break tolerance in any of the 8 mice injected. In contrast, high-pressure treatment of the freeze-thaw and agitated samples did not reduce the immune responses induced against these samples (p=0.133, p=0.378).

Secondary responses to mGH aggregates. Administration of mGH adsorbed to alum or glass microparticles induced the highest levels of IgG1 and also provoked typical secondary immune responses as evidenced by the order-of-magnitude higher levels of IgG1 in the 6th bleed compared to earlier time points. The responses to mGH adsorbed on alum measured at bleed 6 were significantly higher than those at bleed 5 and bleed 4 (p=0.042, p=0.055). Similarly, the antibody responses from bleed 6 of mice injected with mGH adsorbed to glass microparticles were higher than responses at bleed 5 and bleed 4 (p=0.011 and 0.009, respectively). In contrast, although the antibody responses in the mice injected with high-pressure treated, freeze-thawed mGH have a qualitatively similar trend to the alum and glass antibody responses, the response detected at bleed 6 was not significantly higher than responses at bleed 5 and bleed 4 (p=0.190, p=0.139). Thus, only samples adsorbed on glass or alum provoked detectable secondary immune responses.

Mouse weight gain. The average weight gain of the entire mouse population over the 7 weeks of the study was 4.5±0.5 grams. No differences in average weight gain were observed for the different treatment groups, including mice that were injected with buffer alone (negative control). Previous studies reported that the average weight gain from 6 weeks to 13 weeks for CB6F1 female mice is 3±2 grams (24). Therefore, in our study no preparation of mGH promoted excessive weight gain or weight loss.

Size-exclusion chromatographic analysis. No soluble aggregates were detectable by SE-HPLC in any of the mGH preparations. The mass loss in the monomeric peak in the chromatogram was used to determine the percentage of protein in insoluble aggregates (Tables 1 and 2). The highest levels of insoluble aggregates were in the freeze-thawed and agitated samples. After pressurization 100% of the area of the monomer peak was measured by SE-HPLC. In samples containing glass or alum microparticles, 100% of the mGH was adsorbed to the microparticles. Samples with mGH adsorbed to glass or alum were not treated with high pressure.

Figure 10:
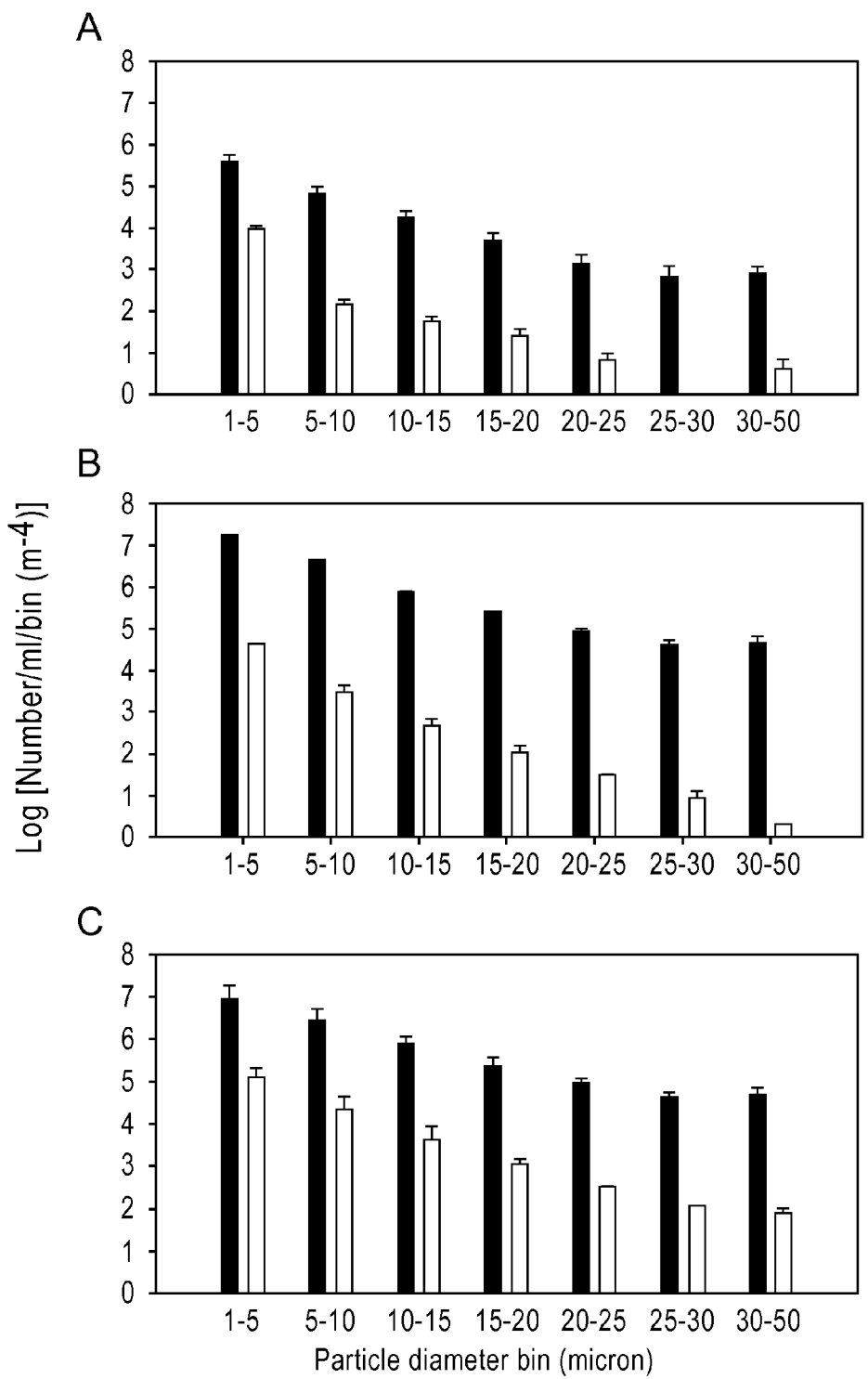
FIG. 10 shows the number counts of particles 1-50 µm in size in stock (panel a), agitated (panel b) and freeze-thaw (panel c) mGH preparations before and after high pressure treatment, represented by the black and grey bars respectively.
Figure 11:
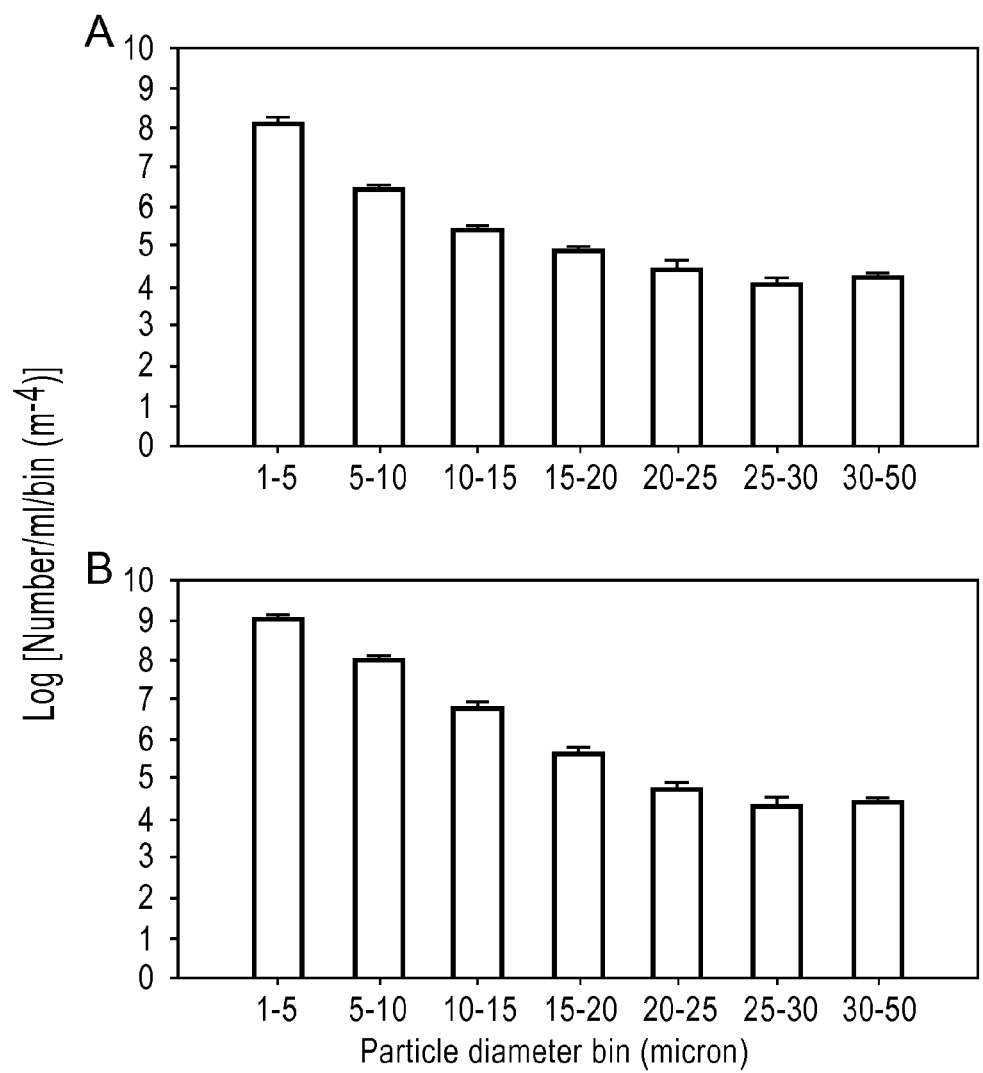
FIG. 11 shows the number of particles 1-50 µm in size for mGH adsorbed to alum (panel a) and glass (panel b).

Micro-flow Imaging analysis. The samples were analyzed for subvisible particles using a Micro-Flow Imaging™ (MFI) instrument. Large numbers of particles were detected in all samples, including those where aggregates were undetectable by SE-HPLC analysis (FIG. 10). High-pressure treatment of the stock, agitated and freeze-thawed samples decreased both the numbers of particles and the mass of protein estimated to be in the particles by approximately two orders of magnitude (Table 2). Alum and glass microparticles were predominately of the 1-1.25 micron diameter (FIG. 11).

Figure 12:
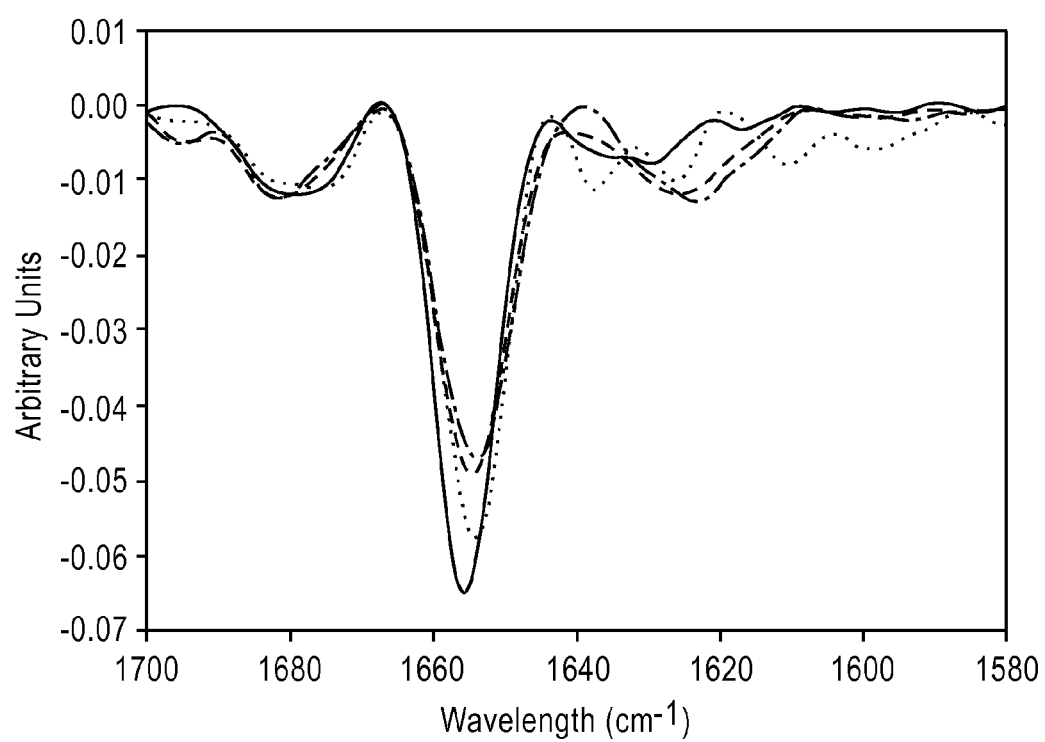
FIG. 12 shows the second derivative infrared spectroscopy of aggregated mGH preparations. The mGH adsorbed to alum and glass microparticles are represented by solid black and dotted grey lines, respectively. The mGH aggregates produced in freeze-thaw and agitation are shown as dark grey dashed and grey dotted-dashed lines, respectively.

Analysis of mGH secondary structure in aggregates and adsorbed to glass or alum. Infrared spectra were obtained for mGH in insoluble aggregates formed during freeze-thawing or agitation and for the protein adsorbed to microparticles of glass or alum. Due to the relatively low solubility (ca. 1 mg/ml) of mGH, the stock and high pressure treated samples could not be concentrated sufficiently to obtain a high quality spectrum for the monomeric, soluble protein. Previous studies reported that infrared spectra of protein adsorbed to alum show native structure (25). Therefore, we assume that mGH adsorbed to alum has native secondary structure. In previous circular dichroism analysis of the monomeric mGH we reported that the protein contained 60% α-helix (21). In the second derivative infrared spectrum, α-helix is represented by a strong negative band at 1654 cm$^{-1}$, which is consistent with the spectrum for the protein adsorbed to alum (FIG. 12). Also, this spectrum is virtually identical to that for native human growth hormone (11, 26). mGH adsorbed onto glass microparticles had only a slight reduction in α-helix, whereas the protein in insoluble aggregates induced by freeze-thawing or agitation had reduced (by ca. 10%) α-helix content.

Figure 13:
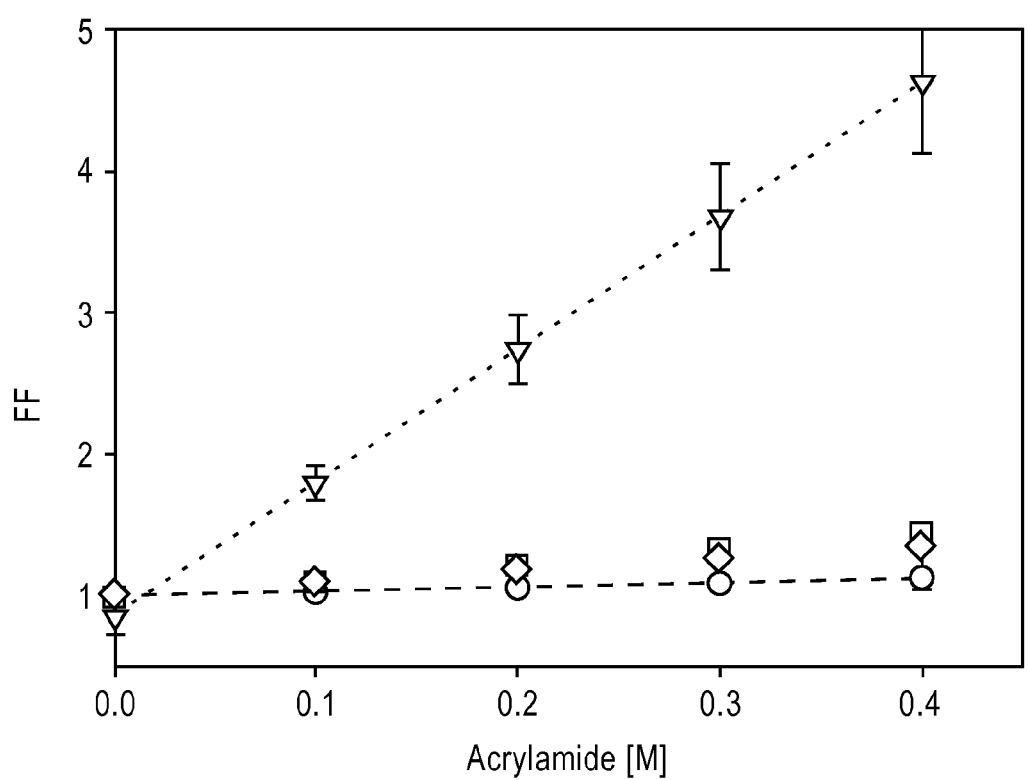
FIG. 13 Stern-Volmer plot of native, unfolded and particle adsorbed mGH. The native and unfolded protein solutions are represented by solid black circles (●) with dashed line and grey triangles (▼) with dotted grey line respectively. Protein adsorbed to Alhydrogel and glass particles are shown as grey diamonds (◆) and dark grey squares (▩) respectively. Some error bars are smaller than data point symbols.

Acrylamide quenching fluorescence spectroscopic analysis of tertiary structure in adsorbed mGH. We compared the Stern-Volmer constant for the adsorbed protein to that for native and unfolded mGH. FIG. 13. The Stern-Volmer constant of native mGH in solution was 0.31±0.17 M−1. Acrylamide has ready access to the tryptophan in unfolded mGH, as evidenced by a Stern-Volmer constant of 9.4±1.2 M−1. mGH has one tryptophan (27). Although the high resolution structure of mGH is not known, the single tryptophan residue in human GH (hGH) is buried in an α-helix bundle (28). Due to sequence similarities between mGH and hGH and our quenching results it is clear that the tryptophan residue in native mGH also has minimal solvent exposure. For the mGH adsorbed to alum or glass microparticles the Stern-Volmer constants were 0.84±0.08 and 1.1±0.2 M$^{-1}$ respectively suggesting that the tertiary structure of mGH adsorbed to glass and alum microparticles is minimally perturbed from that of native mGH.

Discussion

Subcutaneous administration of aggregates of mGH broke immune tolerance to mGH in mice. We characterized the aggregates by SE-HPLC, spectroscopic analysis and MFI. MFI analysis detected subvisible protein aggregates (1 to 50 micron) in samples that were not detectable by SE-HPLC. In addition to particle counts, we estimated the mass of protein contained in particles in stock, HP stock, agitated, HP agitated, freeze-thaw and HP freeze-thaw samples. Aggregate concentrations below 2% can be difficult to detect and quantify by chromatographic analysis (29). However, MFI analysis was able to detect aggregates at concentrations as low as 0.001%. For agitated and freeze-thaw preparations of mGH, MFI and SE-HPLC analyses reported similar percentages of insoluble protein aggregates.

Although the stock solution contained particulate aggregate levels below limits of detection by SE-HPLC, based on the MFI results it is estimated that the mass of protein in subvisible particles was equivalent to 1.6 ng aggregate/injection. This level of particulate aggregate was able to induce immune responses in a fraction of the mice. High pressure treatment reduced particle counts by two orders of magnitude to equivalent doses of 0.02 ng aggregate/injection, which did not break tolerance in any mice. These results suggest that there may be a threshold level of aggregate content within a therapeutic formulation above which immune responses may be generated. Furthermore, they suggest that subvisible particles of protein may be most potent in eliciting an immune response.

In our study, adsorbing mGH to glass or alum yielded a strong adjuvant response. Not only did the glass and alum samples induce the highest antibody production, and immune responses in the most mice, they both provoked secondary immune responses. Vaccine formulations commonly employ adjuvants to sensitize immune responses to antigen. Although there is debate about the mechanism(s) by which aluminum salts increase immune responses to adsorbed antigens, it has been suggested that aluminum salts and other particulate adjuvants can enhance uptake by macrophages as well as induce immunostimulatory cytokines that can lead to faster maturation of dendritic cells (31). Aluminum hydroxide enhances immune responses in a T-cell dependent, Th2 biased fashion, resulting in higher IgG1 than IgG2a isotype titers (32). This is consistent with our results wherein µg/ml concentrations of IgG1, but undetectable levels IgG2a, were produced in mice immunized with mGH adsorbed to alum. Interestingly, administration of mGH adsorbed to glass microparticles yielded the same result. This suggests that microscopic glass particles may also induce T-cell dependent immune responses by enhancing protein uptake by macrophages. Because microscopic glass contaminants are ubiquitous in protein solutions stored in glass containers (33), this result raises the possibility that primary containers may contribute to immunogenicity of therapeutic proteins.

Furthermore, generation of IgG1 was most frequently encountered response to all of the mGH samples tested. IgG1 responses are characteristic of T-cell dependent immune responses (34). Thus, it appears that subcutaneous injection of all of the aggregate types of mGH tested in this study induces T-cell dependent activation of B cells leading to antibody production.

The only mGH samples that produced both IgG2a and IgG2b isotypes were those containing agitation-induced aggregates. IgG2 antibodies often are generated in response to viral infections and lead to cytokine-induced Th1 responses (35-37). Th1 responses stimulate macrophage rather than B cell activation (38), which could explain why the agitation-induced aggregates also provoked the lowest IgG1 concentrations. We speculate that aggregates produced by agitation may exhibit a relatively ordered and repetitive surface structure, leading the immune system to recognize it as a virus.

Also important to note is that the strain of mice used in this study was CB6F1, which is the first generation of a cross between the C57BL/6 and BALB/c strains. The C57BL/6 strain has the Igh1-b allele which leads to the deletion of the IgG2a isotype (39). BALB/c mice are known to not produce IgG2c isotype due to the Igh1-a allele (39). By crossing the two strains we achieve production of all three IgG2 isotypes. Even though all three isotypes of IgG2 were detected, the IgG2b isotype responses were more prevalent than the IgG2a and IgG2c isotype responses.

The IgG3 isotype is an indicator of T-cell independent B-cell activation (40-42). Although there were IgG1 and IgG2 isotype responders in each group, the IgG3 isotype was not significantly produced in any of the groups of mice, consistent with a T-cell dependent mechanism for breaking tolerance.

Our results show that even at levels that are below the limit of detection of SE-HPLC, aggregates of mGH are capable of inducing potent T cell-dependent responses. These data suggest that even small fractions of protein aggregates contaminating therapeutic products can have serious implications. The particles we injected in mice were predominately of the 1-10 micron in diameter size ranges. This size range is notoriously difficult to detect, and is currently not regulated in USP-required tests. Subvisible particulate aggregates of this size range are most likely taken up by phagocytes when injected subcutaneously, which can lead to a strong T-cell dependent immune response taking place in the lymph nodes. Lymph conduits drain antigens and antigen presenting cells to lymph nodes and B follicles. These "B-cell highways", are one pathway by which T-cells and B-cells in the lymph nodes may encounter antigens (43). Antigens must be less than 70 kDa in size to successfully enter these conduits (43). Larger particulate antigens, such as those we injected in mice, are phagocytosed by macrophages or dendritic cells and do not independently enter lymph conduits. Therefore, most insoluble protein aggregates are too large to migrate to the lymph node and activate B-cells independent of T-cells.

In addition to antigen size, the route of administration can also have an influence on immunogenicity of a therapeutic protein (44, 45). Antigens delivered by different routes of administration may migrate to different organs such as lymph nodes and spleen, where they may provoke different immune responses. Studies by Dintzis et al. (46), report that antigens capable of activating B cells independent of T cells had to be at least 100 kDa in size when injected intraperitoneally. The mGH aggregates produced in our study had molecular weights greater than 100 kDa, but were injected subcutaneously. Subcutaneous injections stimulate activity in the lymph nodes (47). In contrast, the main lymphoid organ responsible for antibody production for intraperitoneal injections is the spleen (47). The peritoneum has a low population of dendritic cells compared to macrophages and peritoneal macrophages have lower antigen-presenting capacity (48, 49). Thus, intraperitoneal injections may expose B-cells to large aggregates independent of antigen presenting cells. The ability of antigen to activate B cells independent of T cells may also depend on the population of B cells in the lymphatic tissue that the immune response takes place. Lymph nodes have high populations of T cells and low populations of B cells (50, 51). In contrast, the spleen has high populations of B cells and lower concentrations of T cells (50, 51). Due to the greater population of B cells in the spleen, it is more probable for antigen to encounter B cells and thus activate them without the assistance of T-cells.

In conclusion, frequent subcutaneous administrations of even very low levels of subvisible protein aggregates have the ability to break tolerance in mice. Furthermore, administration of protein adsorbed to microparticles can induce potent T-cell dependent immune responses, much like an adjuvanted vaccine. Clearly, a need exists for new analytical detection and regulation of subvisible particles in final product formulation to minimize any potential adverse effects.

REFERENCES

The following references are hereby incorporated by reference.

1. Waites, M. J., Morgan, N. L. 2001. Industrial Microbiology: An Introduction. Blackwell Science, Inc., Malden.
2. Rosenberg, A. S., and A. Worobec. 2004. A risk-based approach to immunogenicity concerns of therapeutic protein products Part 1 Considering consequences of the immune response to a protein. Biopharm International 17:22.
3. Rosenberg, A. S. 2006. Effects of protein aggregates: An immunologic perspective. Aaps Journal 8:E501.
4. Hermeling, S., D. J. A. Crommelin, H. Schellekens, and W. Jiskoot. 2004. Structure-immunogenicity relationships of therapeutic proteins. Pharmaceutical Research 21:897.
5. Sauerborn, M., V. Brinks, W. Jiskoot, and H. Schellekens. Immunological mechanism underlying the immune response to recombinant human protein therapeutics. Trends in Pharmacological Sciences 31:53.
6. Uversky, V. N. 2009. Intrinsically Disordered Proteins and Their Environment: Effects of Strong Denaturants, Temperature, pH, Counter Ions, Membranes, Binding Partners, Osmolytes, and Macromolecular Crowding. Protein Journal 28:305.
7. Hawe, A., J. C. Kasper, W. Friess, and W. Jiskoot. 2009. Structural properties of monoclonal antibody aggregates induced by freeze-thawing and thermal stress. European Journal of Pharmaceutical Sciences 38:79.
8. Rathore, N., and R. S. Rajan. 2008. Current perspectives on stability of protein drug products during formulation, fill and finish operations. Biotechnology Progress 24:504.
9. Manning, M. C., D. K. Chou, B. M. Murphy, R. W. Payne, and D. S. Katayama. Stability of Protein Pharmaceuticals: An Update. Pharmaceutical Research 27:544.
10. Wang, W., S. Nema, and D. Teagarden. Protein aggregation-Pathways and influencing factors. International Journal of Pharmaceutics 390:89.

11. Fradkin, A. H., J. F. Carpenter, and T. W. Randolph. 2009. Immunogenicity of Aggregates of Recombinant Human Growth Hormone in Mouse Models. Journal of Pharmaceutical Sciences 98:3247.
12. Koch, C., S. S. Jensen, A. Oster, and G. Houen. 1996. A comparison of the immunogenicity of the native and denatured forms of a protein. Apmis 104:115.
13. Braun, A., L. Kwee, M. A. Labow, and J. Alsenz. 1997. Protein aggregates seem to play a key role among the parameters influencing the antigenicity of interferon alpha (IFN-alpha) in normal and transgenic mice. Pharmaceutical Research 14:1472.
14. Bee, J. S., D. Chiu, S. Sawicki, J. L. Stevenson, K. Chatterjee, E. Freund, J. F. Carpenter, and T. W. Randolph. 2009. Monoclonal Antibody Interactions With Micro- and Nanoparticles: Adsorption, Aggregation, and Accelerated Stress Studies. Journal of Pharmaceutical Sciences 98:3218.
15. Tyagi, A. K., T. W. Randolph, A. Dong, K. M. Maloney, C. Hitscherich, and J. F. Carpenter. 2009. IgG Particle Formation during Filling Pump Operation: A Case Study of Heterogeneous Nucleation on Stainless Steel Nanoparticles. Journal of Pharmaceutical Sciences 98:94.
16. Chi, E. Y., J. Weickmann, J. F. Carpenter, M. C. Manning, and T. W. Randolph. 2005. Heterogeneous nucleation-controlled particulate formation of recombinant human platelet-activating factor acetylhydrolase in pharmaceutical formulation. Journal of Pharmaceutical Sciences 94:256.
17. Lindblad, E. B. 2004. Aluminum adjuvants—in retrospect and prospect. Vaccine 22:3658.
18. Fradkin, A. H., Carpenter, J. F., Randolph, T. W. In Press. Immunogenicity of aggregates of recombinant human growth hormone in mouse models. Journal of Pharmaceutical Sciences.
19. Hermeling, S., H. Schellekens, C. Maas, M. Gebbink, D. I. A. Crommelin, and W. Jiskoot. 2006. Antibody response to aggregated human interferon alpha2b in wild-type and transgenic immune tolerant mice depends on type and level of aggregation. Journal of Pharmaceutical Sciences 95:1084.
20. Hermeling, S., L. Aranha, J. M. A. Damen, M. Slijper, H. Schellekens, D. J. A. Crommelin, and W. Jiskoot. 2005. Structural characterization and immunogenicity in wild-type and immune tolerant mice of degraded recombinant human interferon alpha2b. Pharmaceutical Research 22:1997.
21. Fradkin, A. H., C. S. Boand, S. P. Eisenberg, M. S. Rosendahl, and T. W. Randolph. 2010. Recombinant murine growth hormone from *E. coli* inclusion bodies: Expression, high-pressure solubilization and refolding, and characterization of activity and structure. Biotechnology Progress 26:743.
22. St John, R. J., J. F. Carpenter, and T. W. Randolph. 1999. High pressure fosters protein refolding from aggregates at high concentrations. Proceedings of the National Academy of Sciences of the United States of America 96:13029.
23. Dong, A., P. Huang, and W. S. Caughey. 1990. Protein Secondary Structures in Water from 2nd-Derivative Amide-I Infrared-Spectra. Biochemistry 29:3303.
24. Laboratories, C. R. 2009. CB6F1 Pricing and Literature, Vol. 2009.
25. Dong, A. C., L. S. Jones, B. A. Kerwin, S. Krishnan, and J. F. Carpenter. 2006. Secondary structures of proteins adsorbed onto aluminum hydroxide: Infrared spectroscopic analysis of proteins from low solution concentrations. Analytical Biochemistry 351:282.
26. Yang, T. H., A. C. Dong, J. Meyer, O. L. Johnson, J. L. Cleland, and J. F. Carpenter. 1999. Use of infrared spectroscopy to assess secondary structure of human growth hormone within biodegradable microspheres. Journal of Pharmaceutical Sciences 88:161.
27. Fradkin, A. H., Boand, C. S., Eisenberg, S. P., Rosendahl, M. S., Randolph, T. W. 2010. Recombinant murine growth hormone from *E. coli* inclusion bodies: Expression, high-pressure solubilization and refolding, characterization of activity and structure. Biotechnology Progress Early View.
28. Sukumar, M., S. M. Storms, and M. R. De Felippis. 2005. Non-native intermediate conformational states of human growth hormone in the presence of organic solvents. Pharmaceutical Research 22:789.
29. Carpenter, J. F., T. W. Randolph, W. Jiskoot, D. J. A. Crommelin, C. R. Middaugh, and G. Winter. 2010. Potential Inaccurate Quantitation and Sizing of Protein Aggregates by Size Exclusion Chromatography: Essential Need to Use Orthogonal Methods to Assure the Quality of Therapeutic Protein Products. Journal of Pharmaceutical Sciences 99:2200.
30. Carpenter, J. F., T. W. Randolph, W. Jiskoot, D. J. A. Crommelin, C. R. Middaugh, G. Winter, Y. X. Fan, S. Kirshner, D. Verthelyi, S. Kozlowski, K. A. Clouse, P. G. Swann, A. Rosenberg, and B. Cherney. 2009. Overlooking Subvisible Particles in Therapeutic Protein Products: Gaps That May Compromise Product Quality. Journal of Pharmaceutical Sciences 98:1201.
31. De Gregorio, E., U. D'Oro, and A. Wack. 2009. Immunology of TLR-independent vaccine adjuvants. Current Opinion in Immunology 21:339.
32. Jiang, B. M., M. K. Estes, C. Barone, V. Barniak, C. M. O'Neal, A. Ottaiano, H. P. Madore, and M. E. Conner. 1999. Heterotypic protection from rotavirus infection in mice vaccinated with virus-like particles. Vaccine 17:1005.
33. Sacha, G. A., W. Saffell-Clemmer, K. Abram, and M. J. Akers. Practical fundamentals of glass, rubber, and plastic sterile packaging systems. Pharmaceutical Development and Technology 15:6.
34. Rosenberg, Y. J. 1981. The Ability of Nonspecific T-Cell Stimulators to Induce Helper-Cell-Dependent Increases in Either Polyclonal or Isotype-Restricted Ig Production Invivo. Cellular Immunology 61:416.
35. Snapper, C. M., and W. E. Paul. 1987. Interferon-Gamma and B-Cell Stimulatory Factor-I Reciprocally Regulate Ig Isotype Production. Science 236:944.
36. Coutelier, J. P., J. T. M. Vanderlogt, F. W. A. Heessen, G. Warnier, and J. Vansnick. 1987. Igg2a Restriction of Murine Antibodies Elicited by Viral-Infections. Journal of Experimental Medicine 165:64.
37. Finkelman, F. D., I. M. Katona, T. R. Mosmann, and R. L. Coffman. 1988. Ifn-Gamma Regulates the Isotypes of Ig Secreted During Invivo Humoral Immune-Responses. Journal of Immunology 140:1022.
38. Charles A. Janeway, P. T., Mark Walport, Mark Schlomchik. 2005. Basic Concepts in Immunology. In Immunobiology: The Immune System in Health and Disease. E. Lawrence, ed. Garland Science Publishing, New York, p. 1.
39. Martin, R. M., J. L. Brady, and A. M. Lew. 1998. The need for IgG2c specific antiserum when isotyping antibodies from C57BL/6 and NOD mice. Journal of Immunological Methods 212:187.
40. Teale, J. M., and K. M. Abraham. 1987. The Regulation of Antibody Class Expression. Immunology Today 8:122.

41. Perlmutter, R. M., D. Hansburg, D. E. Briles, R. A. Nicolotti, and J. M. Davie. 1978. Subclass Restriction of Murine Anti-Carbohydrate Antibodies. Journal of Immunology 121:566.
42. Snapper, C. M., T. M. McIntyre, R. Mandler, L. M. T. Pecanha, F. D. Finkelman, A. Lees, and J. J. Mond. 1992. Induction of Igg3 Secretion by Interferon Gamma—a Model for T-Cell Independent Class Switching in Response to T-Cell Independent Type-2 Antigens. Journal of Experimental Medicine 175:1367.
43. Gonzalez, S. F., L. A. Pitcher, T. Mempel, F. Schuerpf, and M. C. Carroll. 2009. B cell acquisition of antigen in vivo. Current Opinion in Immunology 21:251.
44. Schellekens, H. 2003. Immunogenicity of therapeutic proteins. Nephrology Dialysis Transplantation 18:1257.
45. Schellekens, H., and N. Casadevall. 2004. Immunogenicity of recombinant human proteins: causes and consequences. Journal of Neurology 251:4.
46. Dintzis, H. M., R. Z. Dintzis, and B. Vogelstein. 1976. Molecular Determinants of Immunogenicity—Immunon Model of Immune-Response. Proceedings of the National Academy of Sciences of the United States of America 73:3671.
47. Tamura, S. I., and Y. Egashira. 1976. Cellular and Humoral Immune-Responses in Mice .3. Acceleration of Delayed-Hypersensitivity Response by Presensitization with Suboptimal Dose of Antigen. Immunology 30:705.
48. McCully, M. L., and J. Madrenas. 2006. Dendritic cells as arbiters of peritoneal immune responses. Peritoneal Dialysis International 26:8.
49. Betjes, M. G. H., C. W. Tuk, D. G. Struijk, R. T. Krediet, L. Arisz, and R. H. J. Beelen. 1993. Antigen-Presenting Capacity of Macrophages and Dendritic Cells in the Peritoneal-Cavity of Patients Treated with Peritoneal-Dialysis. Clinical and Experimental Immunology 94:377.
50. Raff, M. C., Owen, J. J. 1971. Thymus-derived lymphocytes: their distribution and role in the development of peripheral lymphoid tissues of the mouse. Europ. J. Immunol.:27.
51. Raff, M. C., Cantor, H. 1971. Subpopulations of thymus cells and thymus-derived lymphocytes. Progr. Immunol.: 83.

Example 3

Subvisible Particle Analysis of Betaseron

The purpose of this example was to examine the presence of subvisible particles in Betaseron, an Interferon Beta-1b formulation manufactured by Bayer.
Materials and Methods
Betaseron® (Bayer, Lot#AA8004A) was bought from the University of Colorado School of Pharmacy Apothecary. Three vials were reconstituted following the manufacturer's instruction in the provided diluent (0.54% sodium chloride) and analyzed in duplicate by MFI. One syringe of diluent solution was recovered to analyze its particle content.
Particle analysis was performed using Micro-Flow Imaging™ on a DPA 4100 (Brightwell Technologies, Inc.). 0.2 micron filtered water was flushed through the system prior to sample analysis to obtain a clean baseline. Optimize illumination was performed using Betaseron's diluent solution. Approximately 0.32 ml samples of each preparation were analyzed at a flow rate of 0.1 ml/min through a high magnification flow cell using a configuration to detection of particles 1.125-100 μm. The data obtained were number of particles per volume per size range.

Figure 17:
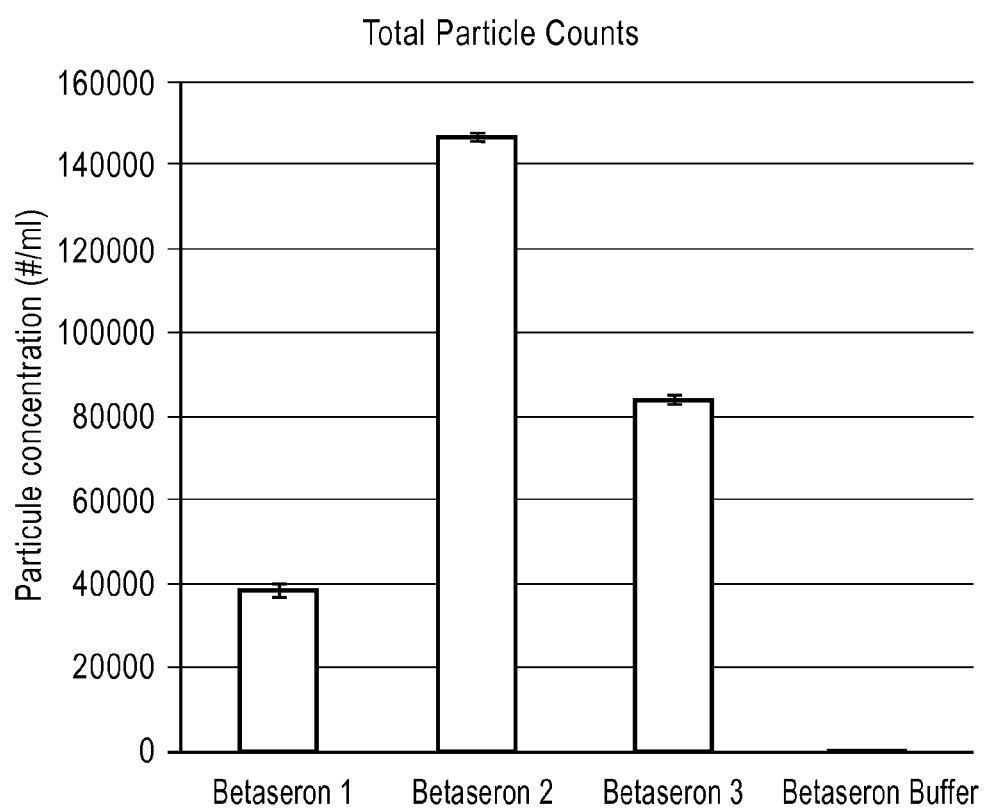
FIG. 17 shows MFI total particle analysis of Betaseron.
Figure 18:
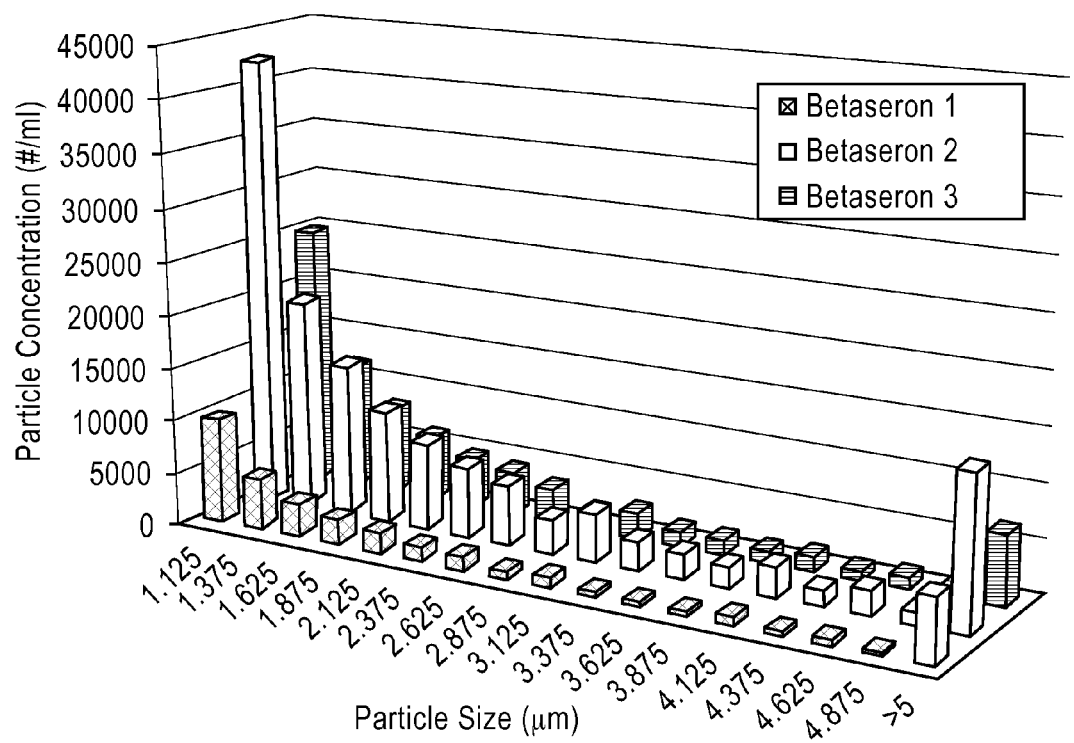
FIG. 18 shows MFI particle size distribution analysis of Betaseron. To get an approximate mass of protein in the subvisible particles present in Betaseron formulation the mass of each particle was determined by assuming a density of the spherical particles of 1.2 g/ml. An approximation of the mass percentage of total protein forming subvisible particles is 2.36%+/−0.83%.

Results
Betaseron is formulated with human albumin (HSA) thus preventing standard SEC-HPLC chromatography. Studies by Runkel et al. demonstrate that Betaseron contains approximately 60% aggregates in higher order aggregates and aggregates complexed with HSA.
Betaseron were analyzed by MFI. Three vials were reconstituted and one syringe of diluents solution was recovered to analyze its particle content. After Betaseron reconstitution, approximately 1.2 ml were recovered, enough volume to analyze each sample in duplicate. When analyzing Betaseron formulations, the particle counts ranged between 38,000 and 147,000 particles/ml (FIG. 17) showing the high variability in particle content between the three preparations; on average Betaseron had 89,800 particles/ml. Particle size distribution is shown in FIG. 18. Betaseron buffer had very low levels of particle counts indicating that the protein in the formulation is the main contributor to the particles detected by MFI. These results suggest that the particles are caused by aggregation of the protein present in the formulation.

Example 4

Transgenic Mouse Study

Immunogenicity of IFN-Beta Formulations

Figure 19:
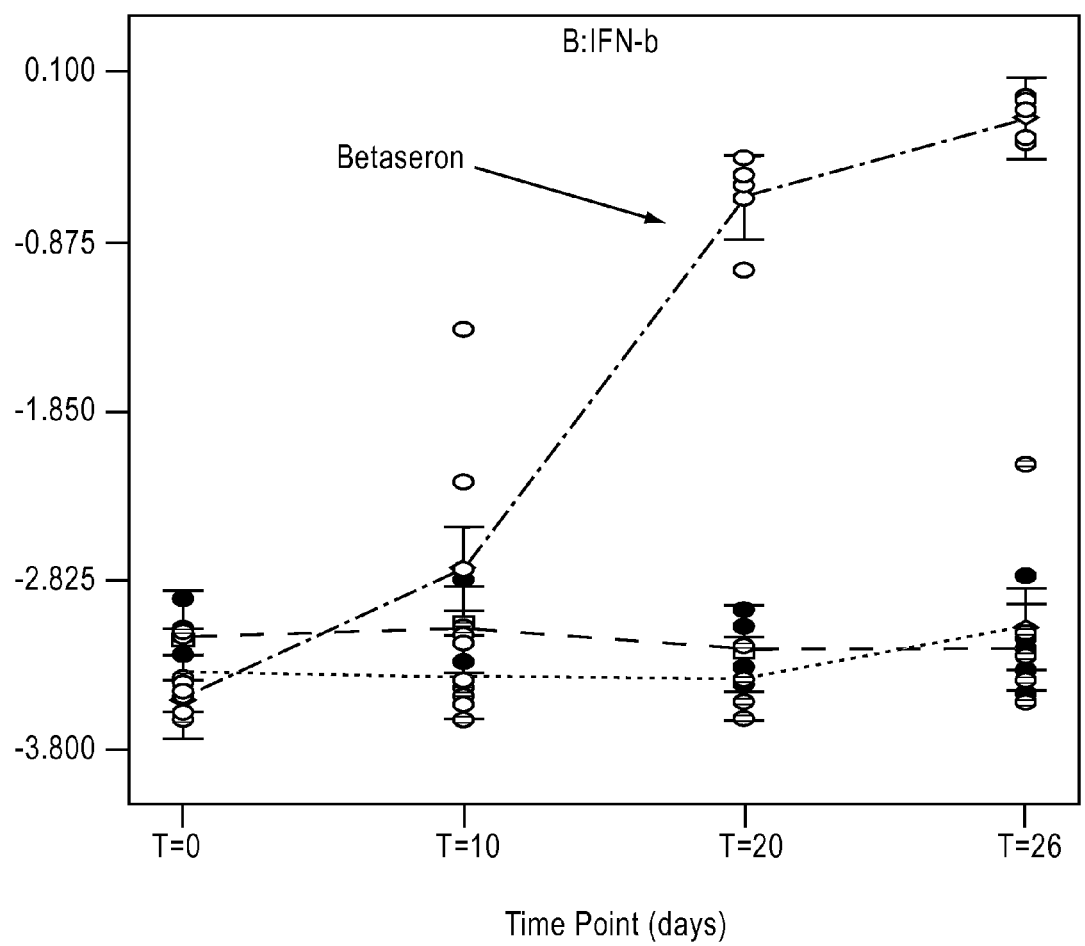
FIG. 19 shows Log 10 relative serum antibody potency of binding antibodies to BaroFeron, Avonix, and Betaseron. BaroFeron data is shown in red, Avonix in green, and Betaseron in Blue. Dosing of Betaseron resulted in a significant development of binding antibodies to monomeric Betaseron relative to baseline. Neither Avonix or BaroFeron developed a significant response.

The purpose of this Example was to confirm that aggregates and subvisible particles present in current Betaseron formulations leads to the development of binding antibodies to monomeric IFN-beta. Avonex and pressure treated IFN-beta-1b were used for comparison.
Materials and Methods
Commercial Betaseron (Lot#WA9497A) and Avonex (Lot#P32033) formulations were purchased and used as formulated. Pressure treated IFN-beta-1b was used at a protein concentration of 0.11 mg/ml, formulated 25 mM acetate (pH 4.0), 9% trehalose, 0.01% Tween 20. SEC-HPLC measurements demonstrated that this material contained less than 0.05% high molecular weight aggregate.
Dosing of the mice was performed as described in Hermelling et al. [1]. Briefly, all animals (5 per group) were dosed 5 mcg i.p. daily×5×3 wks. After five days of dosing, two days were dose free. One group was assigned to pressure treated IFN-beta-1b, Betaseron, and Avonex respectively. Blood draws were taken on time 0, 10, 20, and 26 days and analyzed for the development of binding antibodies to monomeric IFN-beta-1b by an ELISA protocol.
Results
Absorbance readings were obtained for each group and normalized to the response of a non-transgenic mouse dosed with rhIFN-beta that resulted in a high binding antibody titer. The results are shown in FIG. 19. Animals dosed with Betaseron developed a statistically significant (p<0.0001) amount of binding antibodies to monomeric IFN-beta-1b.
Conclusion
Dosing of Betaseron resulted in a significant development of binding antibodies to monomeric Betaseron relative to baseline Neither Avonex or pressure treated IFN-beta-1b developed a significant response. Long-term dosing of Avonex in humans has demonstrated low-levels of immunogenicity, however with a smaller fraction of patients developing anti-IFN-beta antibodies relative to the ~40% of patients who develop antibodies after Betaseron dosing.

The following references are hereby incorporated by reference.

REFERENCES (1) Hermeling, Suzanne. 2005. Structural aspects of the immunogenicity of therapeutic proteins: transgenic animals as predictors for breaking immune tolerance/Suzanne Hermeling—[S.I.]:[s.n.], Tekst.—Proefschrift Universiteit Utrecht.
(2) Hermeling, Suzanne, W. Jiskoot, D. Crommelin, C. Boman and H. Schellekens. 2005. Development of a Transgenic Mouse Model Immune Tolerant for Human Interferon Beta. Pharmaceutical Research Vol. 22(6).
(3) Hermeling S, Schellekens H, Maas C, Gebbink M F B G, Crommelin D J A, Jiskoot W. (2006) Antibody response to aggregated human interferon alpha2b in wildtype and transgenic immune tolerant mice depends on type and level of aggregation. J Pharm Sci 95: 1084-96.

Example 5

The use of High Pressure for the Removal of Subvisible Particles from Etanercept Formulations Materials and Methods Etanercept (50 mg in a SureClick Autoinjector) was diluted to 10 mg/ml in formulation buffer (25 mM sodium phosphate, 25 mM L-arginine hydrochloride, 100 mM NaCl, 1% sucrose, pH 6.3) and analyzed by SEC-HPLC, SDS-PAGE and Micro-Flow Imaging (MFI) before and after high hydrostatic pressure treatment.

High Hydrostatic Pressure Treatment was conducted as follows.

Experiment 1: Diluted etanercept and formulation buffer were loaded into sealed syringes prepared to accommodate high pressure treatment and subject to different high pressures (1000, 1500, 2000, 2500 and 3000 bar) in a PreEMT150™ pressure vessel or left at atmospheric pressure for 16 hr at 25° C. All experiments were done in singlet. High pressure treated samples were then depressurized stepwise at a rate of 250 bar/5 min, sealed luer tips were cut open and samples placed in labeled tubes for further analysis. Pressure treatment was generated using custom-built, high pressure vessels as described previously.

Experiment 2: Diluted etanercept and formulation buffer were prepared as in experiment 1 in quadruple and subject to 2000 bar or left at atmospheric pressure for 16 hr at 25° C.

For Size Exclusion Chromatography (SEC-HPLC), initial and high pressure treated etanercept (10 mg/ml) were analyzed on a Tosoh G3000 SWXL using the Agilent 1100 HPLC system in 100 mM NaCl, 100 mM phosphate pH 6.8, at a flow rate of 0.6 ml/min for 35 min and detected at 280 nm.

For Micro-Flow Imaging Analysis (MFI), particle analysis was performed using Micro-Flow Imaging™ on a DPA 4100 (Brightwell Technologies, Inc.). 0.2 micron filtered water was flushed through the system prior to sample analysis to obtain a clean baseline. Optimize illumination was performed using formulation buffer. 0.45 ml samples of each preparation were analyzed at a flow rate of 0.1 ml/min through a high magnification flow cell using a configuration to detection of particles 1.125-50. The data obtained were number counts per volume per size range.

Results

The purpose of this example was to examine the presence of subvisible particles in etanercept formulations and determine if high pressure treatment could be used to decrease subvisible particle content. Etanercept, a dimeric fusion protein made up of 2 extracellular domains of the human TNFRII receptor linked to the Fc portion of a type 1 human immunoglobulin has been shown to cause 2-6% of RA patients to develop anti-entanercept antibodies. Bressler et al., *Optimizing use of tumor necrosis factor inhibitors in the management of immune-mediated inflammatory diseases, J. Rheumatol. Suppl.* 85:40-52 (2010).

Figure 20A:
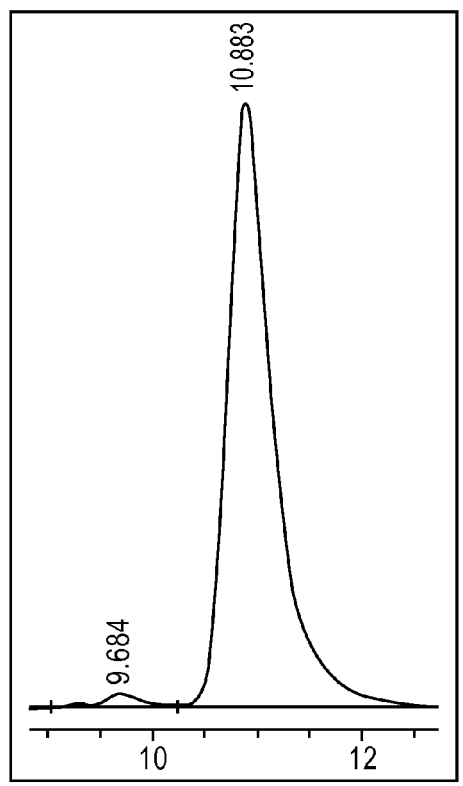
FIG. 20 shows that Etanercept has aggregates in its final formulation. Etanercept was diluted 5× in formulation buffer and analyzed by SEC-HPLC (A) and MFI (B).
Figure 20B:
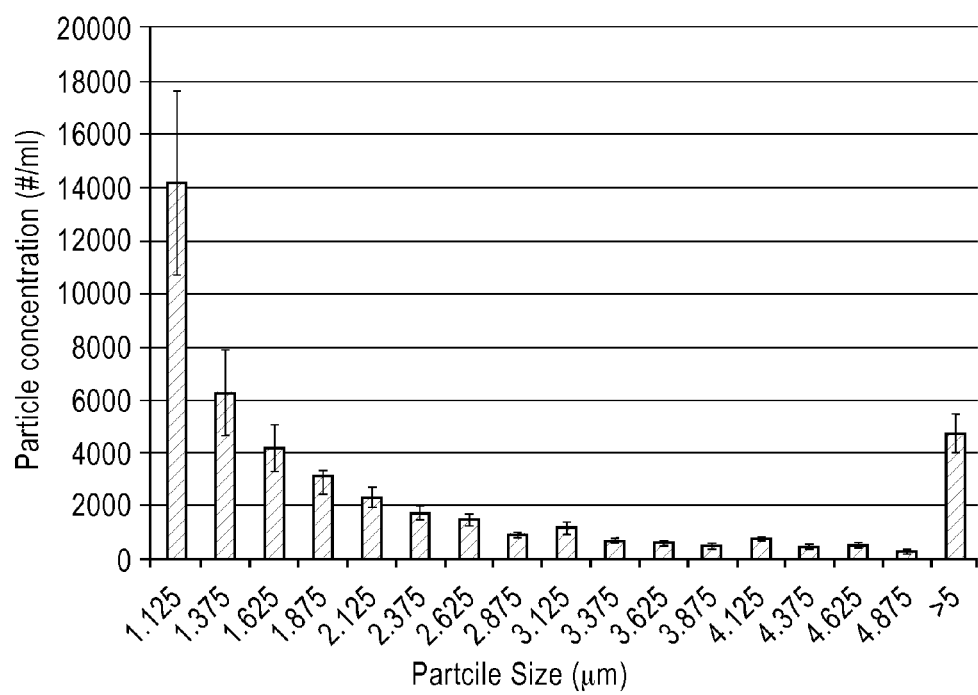

Commercial prefilled syringes of etanercept formulations were purchased, diluted to 10 mg/ml using sterile, particle controlled formulation buffer, and analyzed for aggregate content using SEC chromatography and micro-flow imaging (FIG. 20). Results show that etanercept has a 2.2% of aggregate content in its final formulation as analyzed by SEC-HPLC. When etanercept was analyzed by MFI, an average of 224,000 particles/ml were detected and the majority of the particles were in the range of 1-5 μm in size. SEC is a technique that can only detect particles smaller than 100 nm thus anything larger is undetected. MFI, can detect subvisible particles in the size range of 1-100 μm and these results indicate that etanercept has an aggregate content higher than was described before by other techniques.

Figure 21:
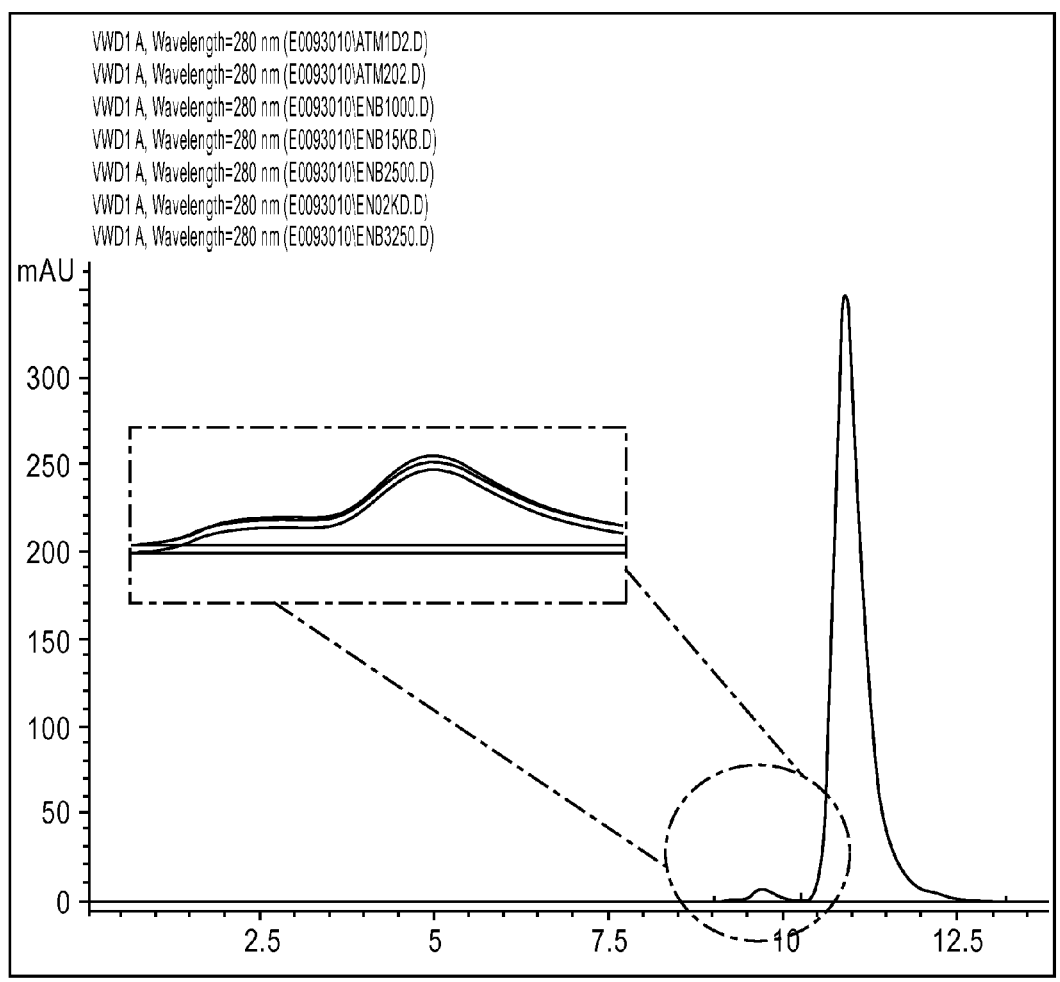
FIG. 21 shows Etanercept diluted to 10 mg/ml, pressure treated, and analyzed by SEC-HPLC. No difference between atmospheric and pressure treated samples can be detected with this analytical method.
Figure 22:
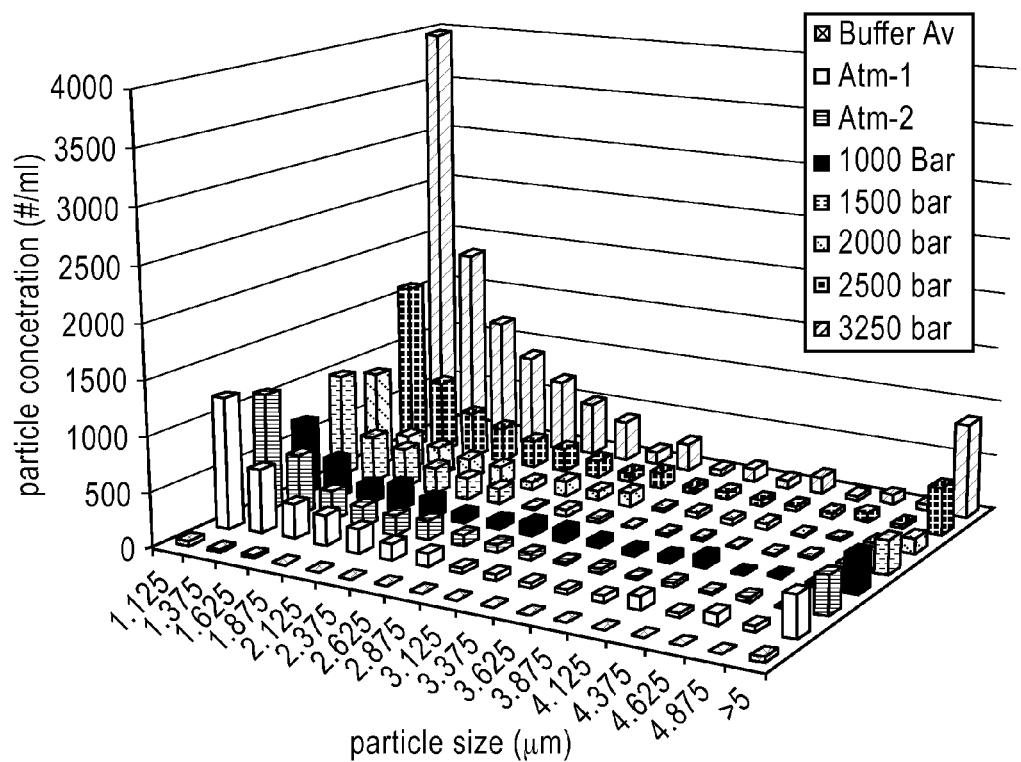
FIG. 22 shows that pressure decreases particles by >25% in the range of 1000-2000 bar. Etanercept was diluted to 10 mg/ml, pressure treated and analyzed by MFI.
Figure 23A:
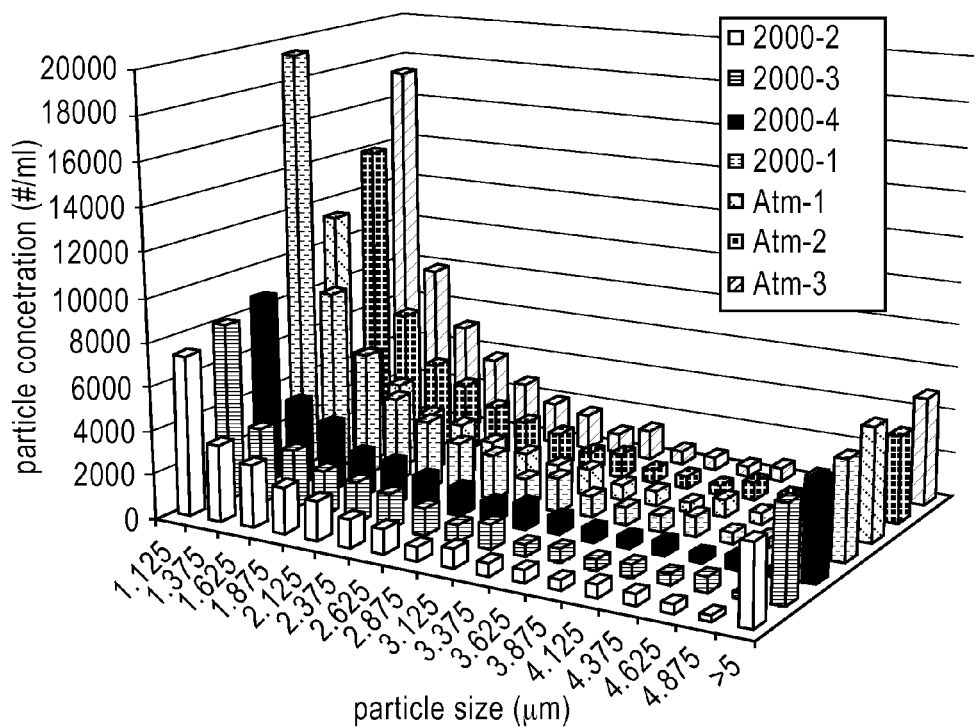
FIG. 23 pressure of 2000 bar decreases subvisible particles by >30% in Etanercept formulations. Etanercept was treated in quadruple at 2000 bar and analyzed by MFI. Panel A shows data for all samples and panel B for the average of treatment at 2000 bar and atmospheric.
Figure 23B:
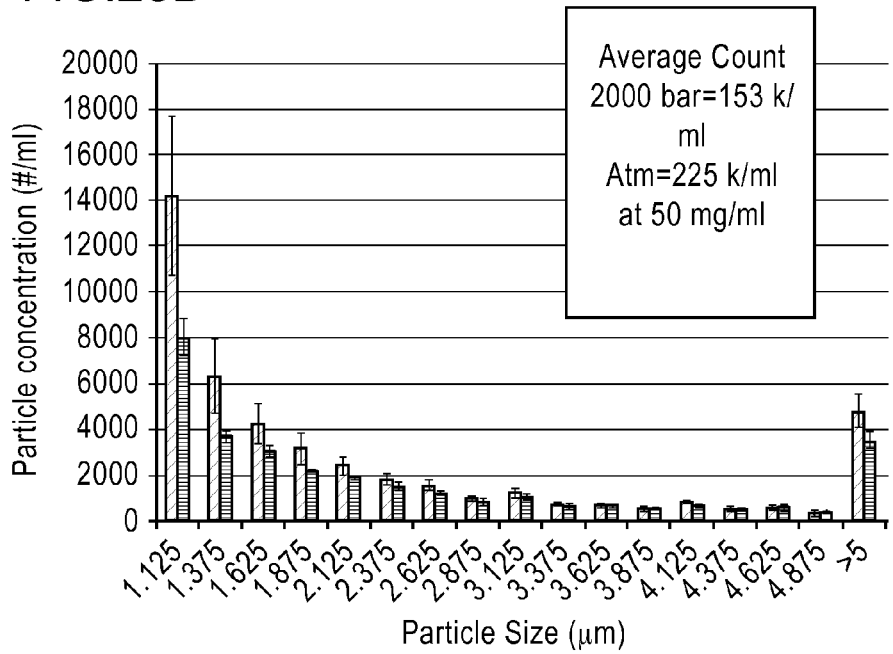

In a preliminary high pressure treatment experiment, diluted etanercept was pressure treated at 1000, 1500, 2000, 2500, and 3000 bar, 25° C., for 16 hours and reassessed for aggregate content. FIG. 21 shows no difference between atmospheric and pressure treated samples as analyzed by SEC-HPLC indicating that pressure treatment did not alter the content of soluble aggregates (dimer and larger). When analyzing samples by MFI, the amount of subvisible particles in etanercept formulations decreased by approximately 25% at pressures ranging 1000-2000 bar (FIG. 22). At high pressures (3250 bar) the amount of subvisible particles increased to ~290,000 particles/ml. These results show that the decrease in aggregate content was dependent on pressure treatment, being most effective at about 2000 bar. Additionally, the increase of subvisible particle content observed after application at high pressures of 3000 bar demonstrate the dependence of the pressure window and that pressure-induced aggregation can occur for some proteins. In a second experiment, etanercept diluted formulations (10 mg/ml) were pressure treated at 2000 bar in quadruple and analyzed by MFI (FIG. 23). Results show that pressure treatment reduced the amount of subvisible particles by >30%.

The invention claimed is:
1. A method for reducing immunogenicity of a therapeutic protein, comprising:
providing a therapeutic protein preparation having at least 90% monomeric protein and greater than 2 ng/ml of subvisible particulates in the range of about 0.1 to about 10 microns in size;
determining high pressure conditions that reduce the subvisible particulates by at least 25% while favoring monomeric protein;
treating the therapeutic protein preparation with high pressure under said high pressure conditions, wherein a reduced level of said subvisible particulates is indicative of reduced immunogenicity.
2. The method of claim 1, wherein the high pressure treatment is configured to reduce the amount of the subvisible particulates, as well as the amount of aggregates of greater than 10 microns in size, and/or the amount of aggregates of less than about 0.1 microns in size.
3. The method of claim 1, wherein the subvisible particulates are reduced to below an immunogenic concentration.

4. The method of any claim 1, wherein the subvisible particulates are quantified by micro-flow imaging, laser diffraction, or coulter counter.

5. The method of claim 4, further comprising, formulating the therapeutic protein for subcutaneous, intramuscular, or intravenous administration.

6. The method of claim 1, wherein the therapeutic protein comprises a monoclonal antibody, an antigen binding domain or single chain antibody, Fc-domain containing protein, an interleukin, interferon, protein hormone, peptide hormone, growth factor, clotting factor, or enzyme for replacement therapy.

7. The method of claim 1, wherein the therapeutic protein preparation prior to high pressure treatment is greater than 90% monomeric material as determined by size exclusion chromatography (SEC).

8. The method of claim 7, wherein the therapeutic protein preparation prior to high pressure treatment is substantially chromatographically pure as determined by SEC.

9. A pharmaceutical composition comprising a therapeutic protein prepared by the process of claim 1.

10. The method of claim 1, wherein the subvisible particulate content is quantified by micro-flow imaging.

11. The method of claim 1, wherein the therapeutic protein preparation n and the conditions include high pressure in the range of about 1000 bar to about 2500 bar.

12. The method of claim 11, wherein the etanercept preparation is substantially chromatographically pure as determined by SEC.

13. The method of claim 11, wherein the subvisible particulates are quantified by micro-flow imaging, laser diffraction, or coulter counter.

14. The method of claim 11, further comprising, formulating the therapeutic protein for subcutaneous, intramuscular, or intravenous administration.

15. The method of claim 1, wherein the therapeutic protein preparation comprises at least 50 ng/ml of said subvisible particulates.

16. The method of claim 1, wherein the therapeutic protein preparation comprises at least 100 ng/ml of said subvisible particulates.

17. The method of claim 1, wherein the subvisible particulates are reduced at least 2-fold by the high pressure treatment.

* * * * *